US007544477B2

(12) United States Patent
Balint et al.

(10) Patent No.: US 7,544,477 B2
(45) Date of Patent: Jun. 9, 2009

(54) CIRCULARLY PERMUTATED, INTERACTION-ACTIVATED PROTEINS

(75) Inventors: Robert F. Balint, Palo Alto, CA (US); Jeng-Horng Her, San Jose, CA (US)

(73) Assignee: KaloBios, Inc., South San Francisco, CA (US)

( * ) Notice: Subject to any disclaimer, the term of this patent is extended or adjusted under 35 U.S.C. 154(b) by 49 days.

(21) Appl. No.: 09/764,163

(22) Filed: Jan. 16, 2001

(65) Prior Publication Data
US 2003/0165825 A1   Sep. 4, 2003

Related U.S. Application Data

(63) Continuation-in-part of application No. 09/526,106, filed on Mar. 15, 2000, now abandoned.

(60) Provisional application No. 60/175,968, filed on Jan. 13, 2000.

(51) Int. Cl.
*C40B 30/08* (2006.01)
*C40B 30/04* (2006.01)

(52) U.S. Cl. .............................. 435/7.1; 435/4; 506/9; 424/134.1

(58) Field of Classification Search ................ 530/350; 435/69.1, 69.7, 183, 966
See application file for complete search history.

(56) References Cited

U.S. PATENT DOCUMENTS 6,270,964 B1 * 8/2001 Michnick et al. ............... 435/6
6,294,330 B1   9/2001 Michnick et al.

FOREIGN PATENT DOCUMENTS

WO   WO 95 29195   11/1995
WO   WO 96 30540   10/1996

(Continued)

OTHER PUBLICATIONS

Pieper et al (Biochemistry, 1997, 36, 8767-8774).*

(Continued)

*Primary Examiner*—Christopher S F Low
*Assistant Examiner*—Christopher M Gross
(74) *Attorney, Agent, or Firm*—Townsend and Townsend and Crew LLP

(57) ABSTRACT

Interaction-activated circularly permutated proteins are disclosed that depend for their functional reassembly into the parent protein on the interaction of heterologous polypeptides or other molecules which have been genetically or chemically conjugated to the break-point termini of engineered enzymes. In addition, methods are provided for identifying circularly permutated marker proteins that will optimally reassemble into a functional parent protein, and which are dependent on the association of heterologous interactor domains. The invention is exemplified by circular permutations of a Class A β-lactamase (TEM-1 of *E. coli*). Circularly permutated marker proteins that comprise molecular interaction-dependent enzymes particularly find use in (1) cell-based sensors for activation or inhibition of metabolic or signal transduction pathways for high-efficiency, (2) high-throughput screening for agonists/antagonists of the target pathway and in high-throughput mapping of pair-wise protein-protein interactions within and between the proteomes of cells, tissues, and pathogenic organisms, and in (3) cell-based screens for high-throughput selection of inhibitors of any protein-protein interaction.

7 Claims, 13 Drawing Sheets

FOREIGN PATENT DOCUMENTS

| | | |
|---|---|---|
| WO | WO 98 34120 | 8/1998 |
| WO | WO 98 44350 | 10/1998 |
| WO | WO 99 28746 | 6/1999 |
| WO | WO 00 07038 | 2/2000 |

OTHER PUBLICATIONS

Remy et al (Proc. Natl. Acad. Sci. USA, vol. 96, pp. 5394-5399, May 1999).*
PDB entry for beta lactamase downloaded Jul. 17, 2007—This citation replaces the citation for item U on the 892 dated Jul. 17, 2007.*
Ostermeier, et al, A combinatorial approach to hybrid enzymes independent of DNA homology, Nature Biotechnology, vol. 17, No. 12, pp. 1205-1209, Dec. 1999.
Ostermeier et al., Combinatorial protein engineering by incremental truncation, Proc. Natl. Acad. Sci., vol. 96, pp. 3562-3567, Mar. 1999.
Blackwood and Eisenman, *Science* (1991) 251:1211.
Defeo-Jones et al., *Nature* (1991) 352:251.
Fields and Song, *Nature* (1989) 340:245.
Chien et al., *Proc. Natl. Acad. Sci.* (1991) 88:9578.
Zervos et al., *Cell* (1993) 72:223.
Vojtek et al., *Cell* (1993) 74:205.
Luban et al., *Cell* (1993) 73:1067.
Bartel et al., *Nature Genetics* (1996) 2:72.
Fromont-Racine et al., *Nature Genetics* (1997) 3:277.
Xu et al., *Proc. Natl. Acad. Sci* (1997) 94:12473.
Bartel et al., *Biotechniques* (1993) 14:920.
Krebber et al., *J. Mol. Biol.* (1997) 268:607.
Cubitt et al., *Trends Biochem* (1995) 20:448.
Rossi et al., *Proc. Natl. Acad. Sci* (1997) 94:8405.
Pelletier et al., *Proc. Natl. Acad. Sci.* (1998) 95:12141.
Karimova et al., *Proc. Natl. Acad. Sci.* (1998) 95:5752.
Pieper et al. *Biochemistry*, (1997) 36: 8767-8774.
U.S. Appl. No. 09/526,106, filed Mar. 15, 2000, Balint, B.F., et al.
Pelletier, et al, Protein Engineering. (1997), 10:89.
Johnson, et al, Proc Natl Acad Sci. (1994) 91:10340-10344.
Voet, D. and Voet, J.G., *Biochemistry*, Second Edition, New York: John Wiley and Sons, 1995, pp. 123-128 (Section 6-3A) and p. 230, column 2, first paragraph.
Wehrman, T., et al., "Protein-protein interactions monitored in mammalian cells via complementation of b-lactamase enzyme fragments," PNAS, Mar. 19, 2002, 99(6):3469-3474.
Lu, Zhijian et al.; "Expression of Thioredoxin Random Peptide Libraries on the *Escherichia coli* Cell Surface as Functional Fusions to Flagellin: A System Designed for Exploring Protein-Protein Interactions"; 1995, *Biotechnology*, vol. 13, pp. 366-372.

* cited by examiner

```
76   cac cca gaa acg ctg gtg aaa gta aaa gat gct gaa gat cag ttg ggt
26    H   P   E   T   L   V   K   V   K   D   A   E   D   Q   L   G 124  gca cga gtg ggt tac atc gaa ctg gat ctc aac agc ggt aag atc ctt
42    A   R   V   G   Y   I   E   L   D   L   N | S   G   K   I   L 172  gag agt ttt cgc ccc gaa gaa cgt ttt cca atg atg agc act ttt aaa
58    E   S   F   R   P   E | E   R   F   P   M   M   S   T   F   K 220  gtt ctg cta tgt ggc gcg gta tta tcc cgt att gac gcc ggg caa gag
74    V   L   L   C   G   A   V   L   S   R   I   D   A   G   Q   E 268  caa ctc ggt cgc cgc ata cac tat tct cag aat gac ttg gtt gag tac
90    Q   L   G   R   R   I   H   Y   S   Q | N   D   L   V   E   Y 316  tca cca gtc aca gaa aag cat ctt acg gat ggc atg aca gta aga gaa
106   S   P   V   T   E   K   H   L   T   D   G   M   T   V   R   E 364  tta tgc agt gct gcc ata acc atg agt gat aac act gcg gcc aac tta
122   L   C   S   A   A   I   T   M   S   D   N   T   A   A   N   L 412  ctt ctg aca acg atc gga gga ccg aag gag cta acc gct ttt ttg cac
138   L   L   T   T   I   G   G   P   K   E   L   T   A   F   L   H 460  aac atg ggg gat cat gta act cgc ctt gat cgt tgg gaa ccg gag ctg
154   N   M   G   D   H   V   T   R   L   D   R   W   E   P   E   L 508  aat gaa gcc ata cca aac gac gag cgt gac acc acg atg cct gta gca
170   N   E   A   I   P | N   D   E   R   D   T   T   M   P   V   A 556  atg gca aca acg ttg cgc aaa cta tta act ggc gaa cta ctt act cta
186   M   A   T   T   L   R   K   L   L   T   G   E | L   L   T   L 604  gct tcc cgg caa caa tta ata gac tgg atg gag gcg gat aaa gtt gca
202   A   S   R   Q   Q   L   I   D   W   M   E   A   D   K | V   A 652  gga cca ctt ctg cgc tcg gcc ctt ccg gct ggc tgg ttt att gct gat
218   G   P   L   L   R   S   A   L   P   A | G   W   F   I   A   D 700  aaa tct gga gcc ggt gag cgt ggg tct cgc ggt atc att gca gca ctg
234   K   S   G   A   G   E   R   G   S   R   G   I   I   A   A   L 748  ggg cca gat ggt aag ccc tcc cgt atc gta gtt atc tac acg acg ggg
250   G   P   D   G | K   P   S   R   I   V   V   I   Y   T   T   G 796  agt cag gca act atg gat gaa cga aat aga cag atc gct gag ata ggt
266   S   Q   A   T   M   D   E   R   N   R   Q   I   A   E   I   G 844  gcc tca ctg att aag cat tgg
282   A   S   L   I   K   H   W
```

Figure 2

| | Interactor 1 | Interactor 2 | Ligand | Max. amp$^r$ | S/N (amp25) |
|---|---|---|---|---|---|
| 1. | scFv | jun helix | CD40-fos helix | 50 μg/ml | >1000 |
| 2. | scFv | jun helix | fos helix-CD40 | 50 μg/ml | >1000 |
| 3. | CD40 | jun helix | scFv-fos helix | 50 μg/ml | >1000 |
| 4. | fos helix | CD40 | scFv-jun helix | 100 μg/ml | >1000 |

```
                          ....,....1....,....2....,....3....,....4....,....5....,....6
              AA         |MGSAIEQDGLHAGSPAAWVERLFGYDWAQQTIGCSDAAVFRLSAQGRPVLFVKTDLSGAL|
              PHD sec    |         HHHHHHH    EEEE     HHHEEE      EEEEE             |
subset:       SUB sec    |LLL....LLLLLLL..HHHHHHH.LL......LLLLL.H......LLL.EEEEE.LLLLL.|
              Rel sec    |98713346566989479999981552322212577754633422499937898517777773|
access:       P_3 acc    |eeebbeeeeeeee eeebbeebee ebbeeeebebbbbbbebeeeeeebbbebeeeeee|
1Ost:         PHD acc    |99700677777875797007606736007677706000000606979676000606777771|

....,....7....,....8....,....9....,...10....,...11....,...12
              AA         |NELQDEAARLSWLATTGVPCAAVLDVVTEAGRDWLLLGEVPGQDLLSSHLAPAEKVSIMA|
              PHD sec    | HHHHHHHHHHHHHH       HHHHHHH    EEEEE        HHHHHHHH|
subset:       SUB sec    |..HHHHHHHHHHHHLLLLL.............E.....LLLLL...LL.HHHHHHHH|
              Rel sec    |327799999999965998723223321223223543102787654245535999999991|
access:       P_3 acc    |eebeeebe bbbbbeeebebbebbebbeeeeebbbbbebbebeebee eeeeebbebbb|
1Ost:         PHD acc    |77077606500000077060060060067776000000700607707775777770060001|

....,...13....,...14....,...15....,...16....,...17....,...18
              AA         |DAMRRLHTLDPATCPFDHQAKHRIERARTRMEAGLVDQDDLDEEHQGLAPAELFARLKAR|
              PHD sec    |HHHHHH          HHHHHHHHHHHHHH       HHH    HHHHHHHHHH |
subset:       SUB sec    |HHHHHH.LLLL.LLLLL...HHHHHHHHHHHH.LLLLLLL.....LLLLHHHHHHHHHH.|
              Rel sec    |9999983886646888733289999999999971555588742213686789999999961|
access:       P_3 acc    |ebbbebbebebeeebbeeebeeebeebeeebeebbb beebeeeeeeebeebbeebeee|
1Ost:         PHD acc    |70006007060770070707706770676077005076077677776076007607771|

....,...19....,...20....,...21....,...22....,...23....,...24
              AA         |MPDGEDLVVTHGDACLPNIMVENGRFSGFIDCGRLGVADRYQDIALATRDIAEELGGEWA|
              PHD sec    |    EEEE      EEE   EEEEEE        HHHHHHHHHHHHHHHHHHH HHHH|
subset:       SUB sec    |LLLLLLEEEE.LLLLLL..E..LL.EEEEE.........HHHHHHHHHHHHHHH.L.HHH|
              Rel sec    |8989966886267886631531883578881431123447899999999999975284999|
access:       P_3 acc    |eeeeeebbbbbbebbbbbbbbeebebbbbbbbbb bbbbb bbbbbbbbeebeeebee e|
1Ost:         PHD acc    |6777770000000600000000670600000000040000500000006606770777361|

....,...25....,...26....,...27....,...28....,...29....,...30
              AA         |DRFLVLYGIAAPDSQRIAFYRLLDEFF|
              PHD sec    |HHHHHHH      HHHHHHHHHHH  |
subset:       SUB sec    |HHHHHHH.LLLLL..HHHHHHHHH.LL|
              Rel sec    |999999737998834667579998359|
access:       P_3 acc    |e bbeebbbee eeeebebbbbbeebb|
1Ost:         PHD acc    |75006600076577760600006600|
```

Figure 12

CIRCULARLY PERMUTATED, INTERACTION-ACTIVATED PROTEINS

CROSS REFERENCE TO RELATED APPLICATIONS

This application claims the benefit of U.S. Provisional Application No. 60/175,968, filed Jan. 13, 2000, and is a continuation-in-part of U.S. Ser. No. 09/526,106, filed Mar. 15, 2000, now abandoned which disclosures are hereby incorporated by reference.

GOVERNMENT LICENSE RIGHTS

This invention was made with government support under 1R43AI45281-01A1and 1R43GM60101-01 awarded by the National Institute of Health. The government has certain rights in the invention.

INTRODUCTION

1. Technical Field

The present invention is concerned with detecting interactions between intracellular as well as extracellular proteins by expressing them as part of a fusion sequence that encodes for a circularly permutated marker protein that reassembles into a directly detectable protein. The interaction-dependent enzyme activation (IdEA) systems of the present invention are exemplified by the use of TEM-1 β-lactamase circular permutations, including ligand-activated circular permutations.

2. Background

Most physiological processes depend on complex networks of cells interacting with one another and their environments, primarily through specific recognition between proteins—from the ligand-mediated assembly of multi-protein complexes at the cell surface, through the labyrinth of intracellular signal transduction cascades, to the assembly of transcription-modulating complexes on the promoters of specific genes. Thus, for most pathological conditions, protein-protein interactions are instrumental and provide a wealth of targets for diagnostic and therapeutic intervention. As a result, new and improved methods are in constant demand for (1) identifying natural ligands of key participants to study their roles in disease, and (2) developing surrogate ligands for therapeutic intervention and diagnosis. A number of methods have been developed over the years to address each of these goals. The most widely used current methods for identifying natural proteins which interact with a protein-of-interest generally involve screening libraries of expressed cDNAs. A few genes for ligands of proteins-of-interest have been isolated by direct screening of cDNA expression libraries on filters for binding to labeled versions of the protein-of-interest, as in antibody probing (Blackwood and Eisenman, Science (1991) 251:1211; Defeo-Jones et al., Nature (1991) 352:251). However, a great many important protein interactions are not robust enough for the harshness of such methods, where conditions of interaction are usually far from native. Also, the false positive frequencies of these methods is high, due to the presence of denatured protein in cells which have been fixed to make the target proteins accessible to probes.

A major advance in cDNA screening methodology came with the development of systems in which screenable or selectable cellular phenotypes can be engineered to depend on desired protein interactions within living cells (Fields and Song Nature (1989) 340:245; Chien et al., Proc Natl Acad Sci (1991) 88:9578; Zervos et al., Cell (1993) 72:223; Vojtek et al., Cell (1993) 74:205; and Luban et al., Cell (1993) 73:1067). The most widely used of these is the yeast "two hybrid" system of Fields and Song (1989, supra). This system takes advantage of the "modularity" of many functional domains in proteins which allows the linking of functions to be manipulated. This is particularly true for transcriptional activators, in which an activation domain which interacts with the core transcription complex is "homed" to specific genes by a sequence-specific DNA-binding domain. For many transcriptional activators these domains can function independently, and in fact are often in separate, interacting subunits. In the yeast two-hybrid system, the "bait" protein is expressed as a fusion with a cis-element sequence-specific DNA-binding domain, and cDNAs are expressed as fusions with a transactivation domain. When, and only when, these two domains are brought together by interaction of a cDNA product with the "bait" protein, can the reporter gene be expressed, since its transcription is dependent on transactivation from the cis-element. Reporters can be either screenable (e.g., β-galactosidase for color) or selectable (e.g., HIS3 for growth in the absence of histidine).

Variations of this system have been successfully employed to identify a number of important protein-protein interactions (Chien et al., 1991, supra; Zervos et al., 1993, supra; Vojtek et al., 1993, supra; and Luban et al., 1993, supra; Bartel et al., Nature Genetics (1996) 2:72; Fromont-Racine et al., Nature Genetics (1997) 3:277; Xu et al., Proc Natl Acad Sci (1997) 94:12473). In spite of its success, however, the original yeast two-hybrid system has serious drawbacks for the high-throughput applications required to accelerate pharmaceutical target discovery from genomics. The fundamental limitation with this system is that many steps are required between the test interaction and the generation of a selectable phenotype. Each such step presents an opportunity for non-specific interaction to raise the false positive background, and for dissociation to allow bona fide interactors to be missed. The false positive problem is exacerbated by the highly combinatorial nature of the transcription machinery and the abundance of protein domains encoded in cDNA libraries which can interact with one or more components of the transcription initiation complex, including transactivator-bound promoter DNA (Bartel et al., BioTechniques (1993) 14:920). Another limitation of the original two-hybrid system is that it generally cannot accommodate secreted or membrane proteins and cytoplasmic proteins must be stable in the yeast nucleus.

Recently the two-hybrid concept has been expanded to include other types of protein functionalities for use as protein-protein interaction reporting systems. For example, in the Selective Infective Phage (SIP) system a protein which confers infectivity on filamentous bacteriophage has been fragmented in such a way that it is functional only when the fragments are fused to heterologous interactors (Krebber et al., J Mol Biol (1997) 268:607). The interaction is then monitored by its ability to allow phage encoding the interactors to transfer a selectable phenotype to susceptible cells by infection. However, this method also suffers from requiring many low-efficiency steps between the target interaction and the expression of the selectable phenotype by the recipient cell. Also like the two-hybrid system, the efficiency of this system suffers from the fact that most natural protein-protein interactions have affinities in the micromolar range, with half-lifes on the order of seconds. When the time delay between interaction and signal generation exceeds this half-life, which it does in these systems, the efficiency of interaction detection declines sharply.

More recently still, the two-hybrid concept has been adapted to proteins which can confer selectable phenotypes directly from protein-protein interactions, with few or no intervening steps between the target interaction and signal generation. For example, interactors can be fused to variants of the Green Fluorescent Protein of *Aequorea victoria* (GFP), which are capable of detectable fluorescence resonance energy transfer (FRET) when brought into close proximity by the interactors (Cubitt et al., *Trends Biochem* (1995) 20:448). Some enzymes which confer selectable or screenable phenotypes on cells can also be adapted for two-hybrid type protein-protein interaction detection (Rossi et al., *Proc Natl Acad Sci* (1997) 94:8405; Pelletier et al., *Proc Natl Acad Sci* (1998) 95:12141). In this variation, protein interactors are fused to enzyme fragments, which by themselves are inactive. However, when the enzyme fragments are brought together by the interaction of the protein domains to which they are fused, the fragments are able to associate to reconstitute the selectable activity of the enzyme. This is an example of interaction-dependent enzyme activation (IdEA), and it is illustrated in FIG. 1. Both IdEA and GFP FRET systems present advantages over previous versions of the two-hybrid concept. For instance, the selectable signal is produced directly from the desired interaction, without any intervening steps which are the main sources of inefficiency in the earlier systems. Such improvements in efficiency and background should make these methods more amenable to high-throughput applications. However, although both IdEA and GFP FRET systems in theory can be set up in both prokaryotic and eukaryotic cells, and either in the cytoplasm or in a secretory pathway to allow interactions to be monitored in natural milieus, they have not. All IdEA systems reported to date have only utilized cytoplasmic enzymes and have only been shown to be operative in that compartment (Rossi et al., 1997, supra; Pelletier et al., 1998, supra; Karimova et al., *Proc Natl Acad Sci* (1998) 95:5752). Indeed, because of their design, these reported systems are not expected to function in the secretory pathway or in the bacterial periplasm. Thus, they are not considered useful for monitoring the interactions of secreted proteins.

The most widely used current systems for the detection of extra-cellular protein-protein interactions, namely viral or cellular display systems, are essentially in vitro methods with high stringencies of selection and/or high backgrounds. Thus, they are not well suited for high-throughput applications. These systems also usually require the use of a purified known heterologous interactor domain or "bait protein", and are therefore not suitable for multiplex applications where neither heterologous interactor domain of a protein binding pair is known a priori, i.e., the combinatorial interaction of two protein libraries with one another for simultaneous identification of all protein binding pair interactions. One system which does not require bait purification for identification of extra-cellular interactions is the *E coli* Dimer Detection System (EDDS; Small Molecule Therapeutics, Inc., Monmouth Junction, N.J.). Bait proteins for this system are restricted to type I membrane receptors which have single transmembrane domains and require simple dimerization for signaling. The ecto-domain of the bait receptor is fused to the transmembrane domain and endo-domain of an *E. Coli* receptor. When this fusion protein is co-expressed with an expression library in the bacterial periplasm, ligands for the receptor can be identified by their ability to dimerize the receptor and induce expression of a selectable phenotype. However, this system suffers from the same limitation as the yeast two-hybrid and SIP systems, namely, that multiple steps between interaction and phenotype cause severe loss of efficiency due to high false positive and false negative rates.

It is therefore of interest to develop IdEA systems capable of simultaneous detection of multiple interactions between extra-cellular as well as intracellular proteins in a high throughput format.

Relevant Literature

Pieper, et al (1997) discloses a constitutively active circular permutation of a Class A β-lactamase.

SUMMARY

Compositions and methods are provided for identifying interactions between two or three polypeptides using interaction-dependent enzyme association systems (IdEAs). The systems are characterized by fusion proteins constructed from the N-terminal and C-terminal segments of a marker protein that functionally reassemble into the marker protein producing a directly detectable signal, such as a visible phenotypic change or antibiotic resistance. A first interaction-dependent enzyme association system described herein involves co-expression in a host cell of a first and a second oligopeptide, where each is an individual fusion protein separated by a flexible polypeptide linker with a member of a marker protein fragment pair. In a second interaction-dependent enzyme association system described herein, first and second oligopeptides are expressed from a nucleotide sequence as a single fusion protein through the first and second break-point termini of a circularly permuted marker protein. In both IdEAs described herein, binding of the first oligopeptide to the second oligopeptide results in the functional reconstitution of the marker protein, and the interacting first and second oligopeptides are identified by isolating and sequencing plasmids from a host cell that displays a directly detectable signal indicative of a functional marker protein. Alternatively, simultaneous binding of the first oligopeptide and the second oligopeptide to a third oligopeptide (i.e., a ligand) results in the functional reconstitution of the marker protein. Therefore, the IdEAs of the present invention are particularly useful for methods of identifying a second oligopeptide to which a first oligopeptide binds, or a third oligopeptide to which a first and second oligopeptide simultaneously bind. The invention is concerned with the above-described fusion proteins for the marker protein fragment pair and circular permutation IdEA systems, and also with DNA sequences, expression cassettes and plasmids comprising nucleic acids encoding the fusion proteins. A circularly permutated interaction dependent marker protein can be expressed from a single expression cassette comprised of in the direction of transcription nucleic acid sequences encoding for a first polypeptide interactor domain, a circularly permutated marker protein, and a second polypeptide interactor domain. The IdEA systems of the present invention are amenable for polypeptide identification in in vitro assays and in vivo in prokaryotic and eukaryotic cells, and is concerned with host cells that contain DNA sequences, expression cassettes, and plasmids that encode marker protein interaction dependent fragment pairs or circular permutations.

The invention also provides for efficient methods of finding functional fragment pairs of a marker protein that involve identifying functional break-points within flexible loops using tertiary or secondary structural information. The interaction-dependent enzyme activation systems of the present invention find particular use in identifying immunoglobulin epitopes, polypeptide sequences that bind to extracellular proteins, and in the high-throughput identification of inhibitors of phophorylation-regulated signal transducer proteins. By tethering first and second interactor domains to the same linear polypeptide, circularly permutated interaction-dependent enzyme activation systems can reduce reaction kinetics by one order of magnitude, which is particularly relevant for assays carried out in the intracellular milieu, and therefore represent a favored system for use as an intracellular signal transduction biosensor. The systems find use as intracellular signal transduction biosensors, not only to identify compounds that modulate phosphorylation-regulated signal transducer proteins, but also for identifying interactions between intracellular proteins involved in signal transduction. The systems also find use in allowing single antibiotic selection of cells transformed to express genes for multiple traits and for targeted and localized activation of derivitized anti-tumor prodrugs.

The present invention describes the first interaction-dependent enzyme activation (IdEA) systems capable of simultaneous detection of multiple interactions between extra-cellular as well as intra-cellular proteins. For instance, polypeptide interactions can be identified in different cellular compartments of a cell depending on the signal peptide chosen, including but not limited to the cytoplasm, the endoplasmic reticulum and associated secretion pathway compartments, the nucleus, and within or on either side of the extracellular membrane.

The IdEA systems described herein are exemplified by the bacterial β-lactamases, a large group of structurally-related enzymes which segregate into several groups on the basis of structural homologies and substrate specificities. For the TEM-1 β-lactamase of $E.$ $coli$, the type member of the Class A penicillinases, circular permutations (CP) have been identified which can be activated when and only when the "break-point" termini of the CPs are fused to proteins or other molecules which interact with each other directly or through a second molecule. Furthermore, methods are outlined whereby activatable circular permutations can be identified and modified specifically to confer dependence of their activity on the interaction of heterologous domains fused to the break-point termini. Ligand-activated or interaction-activated CPs are advantageously used over interaction-dependent fragment complementation systems for certain assays, in that they exhibit lower order kinetics of activation, i.e., uni-molecular instead of bi-molecular for two-component interactions and bi-molecular instead of tri-molecular for three-component interactions. This allows for more efficient detection of ligand and results in significantly greater sensitivities for many applications.

Ligand-activated β-lactamase CPs can be activated in multiple locations, including but not limited to the bacterial periplasm, bacterial cytoplasm, eukaryotic cell cytoplasm, or in vitro. They are highly active against a wide variety of substrates, including antibiotics, chromogens, and fluorogens, as well as β-lactam pro-drugs, pro-antibiotics, and pro-nutrients, which can thus be used for both positive and negative viability selection and color selection. The utility of interaction-activated β-lactamase circular permutations has been demonstrated for monitoring interactions between and among cell-surface receptors, antibodies, and random peptide libraries displayed on the surface of a natural protein.

BRIEF DESCRIPTION OF THE DRAWINGS

FIG. 1 shows two mechanisms for Interaction-dependent Enzyme Activation (IdEA).

FIG. 2 shows the nucleotide coding sequence (SEQ ID NO:1) for the mature form of TEM-1 β-lactamase and the encoded amino acid sequence (SEQ ID NO:2) (Sutcliffe, $Proc$ $Natl$ $Acad$ $Sci$ (1978) 75:3737). From the sequence for plasmid pBR322 (SYNPBR322), Genbank accession no. J01749. The break-points between the α and ω fragments at residues Asn52/Ser53, Glu63/Glu64, Gln99/Asn100, Pro174/Asn175, Glu197/Leu198, Lys215/Val216, Ala227/Gly228 and Gly253/Lys254 are indicated.

- FIG. 7 shows TEM-1 β-lactamase fragment complementation by interaction between representative single-chain antibody Fv fragment (scFv) and thioredoxin-scaffolded peptide (Trx). The N-terminal β-lactamase fragment, α197 (α), is horizontally hatched. The C-terminal fragment, ω198 (ω), is filled with dots. TEM-1, thioredoxin, and the scFv were rendered from published structures. The peptide and the linkers were drawn in.

FIG. 8 shows TEM-1 β-lactamase fragment complementation by interaction between the CD40 extra-cellular domain (CD40) and a thioredoxin-scaffolded peptide (Trx). The N-terminal β-lactamase fragment, α197 (α), is horizontally hatched. The C-terminal fragment, ω198 (ω), is filled with dots. TEM-1, thioredoxin, and the scFv were rendered from published structures. The peptide and the linkers were drawn in.

FIG. 12 shows abbreviated output of the PredictProtein Program for prediction of secondary structure and solvent exposure for NPTII (Rost and Sander, 1993, 1994). The top line shows the amino acid sequence in single letter code (SEQ ID NO:7). The second and third lines show secondary structure prediction. H, helix; E, strand; L, loop. The fourth line shows a measure of reliability on a scale from 1 to 10, with 10 being highest. The fifth line shows solvent accessibility—e, exposed; b, buried. The bottom line shows a measure of reliability for solvent accessibility on a scale of 1 to 10, with 10 being highest. Ten regions of the sequence predicted to have little secondary structure and to be exposed to solvent are indicated by underlining as potential sites for productive fragmentation.

BRIEF DESCRIPTION OF THE SPECIFIC EMBODIMENTS

Figure 1A:
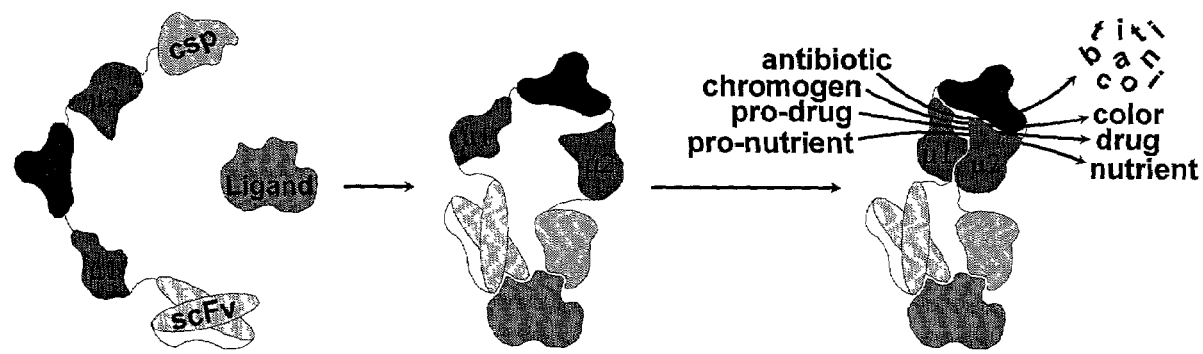
FIG. 1A. Ligand-dependent circular permutations of an enzyme are formed by linking the native termini, and severing the polypeptide chain in a solvent exposed loop to generate new carboxy and amino termini. The circularly permutated enzyme can refold to form an active enzyme when and only when the new termini are brought together by an interaction of heterologous domains fused to the new termini. The interaction can be direct or mediated by a second molecule (the ligand). The ligand-binding domains can include but are not limited to single-chain antibody fragments (scFv) and constrained peptides scaffolded on a carrier protein (csp). Versatile hydrolytic enzymes such as β-lactamases can be used to confer multiple selectable phenotypes including antibiotic resistance, color, death (prodrug, for inhibitor screens), and auxotrophic growth.
Figure 1B:
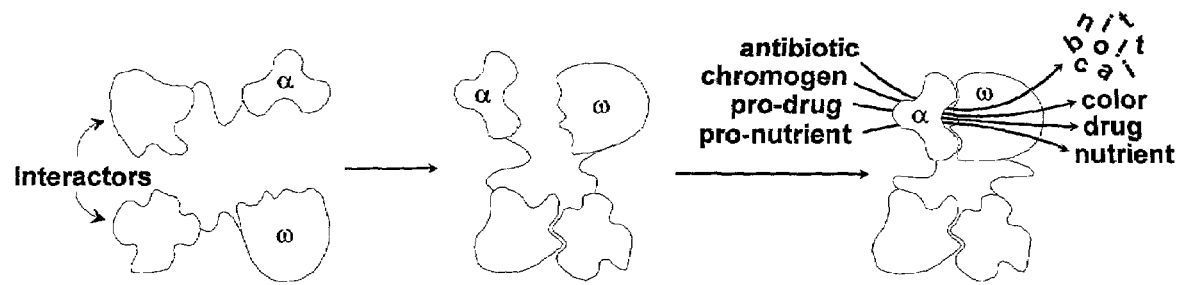
FIG. 1B. Interaction-dependent fragment complementation requires enzyme α and ω fragments which can refold to form active enzyme when and only when they are brought together by an interaction of heterologous domains fused to their termini.

Methods and compositions are provided for interaction-dependent enzyme activation systems useful in detecting an interaction between a first protein and a second target protein or between a first and second protein and a third protein. The methods detect the interaction of a first known or unknown interactor domain with a second unknown interactor domain, or a first and second interactor domain and a third known or unknown interactor domain, by bringing into close proximity members of a fragment pair of a marker protein or a circular permutation of a marker protein, such that the parent marker protein is reassembled to its original functionality, and such that reassembly requires the prior interaction of the heterologous interactor domains. A first interaction-dependent enzyme activation system described herein is characterized by N-terminal and C-terminal fragment members that comprise fragment pairs which are derived from, and can functionally reassemble into a marker protein that provides for a directly detectable signal that does not involve downstream steps necessary for recognition. For example, a marker protein of interest for the instant invention functions of itself to produce a selectable signal such as a visible phenotypic change or antibiotic resistance in a host cell. A second interaction-dependent enzyme activation system is characterized by a circularly permutated marker protein that provides for a directly detectable signal. As used herein, a circularly permutated protein or a circular permutation of a protein refers to a protein where the amino and carboxyl terminal segments are interchanged and rejoined with a short spacer connecting the original N- and C-termini. Heterologous interactor domains are then fused in frame to the N- and C-terminal break-point termini.

In a first interaction-dependent enzyme activation system described herein, the fragment pairs are used in methods that involve the co-expression of a first and a second oligopeptide sequence, in which the first oligopeptide sequence is a fusion protein comprised of in the direction of translation, an N-terminal fragment fused through a break-point terminus to a flexible polypeptide linker and a first interactor domain, and the second oligopeptide sequence is a fusion protein comprised of in the direction of translation, a second interactor domain and a flexible polypeptide linker fused through a break-point terminus to a C-terminal fragment. Where the marker protein is circularly permutated, the first and second oligopeptide interactor domains are fused in frame through a flexible polypeptide linker to the amino and carboxy break-point termini of the circularly permutated marker protein. A circular permutation interaction-dependent enzyme activation system involves the expression of a single fusion polypeptide that comprises in the direction of translation, a first interactor domain that is in frame with a circularly permutated marker protein that is in frame with a second interactor domain. The first and second interactor domains can associate with each other allowing for a unimolecular bipartite molecular interaction, or can both simultaneously associate with a common ligand, allowing for a bimolecular tripartite molecular interaction.

In the interaction-dependent enzyme activation systems presented herein, a flexible polypeptide linker can separate the fragment domain from the interactor domain and allow for their independent folding. The flexible linker is optimally 15 amino acids or 60 Å in length (~4 Å per residue) but can be as long as 30 amino acids but preferably not more than 20 amino acids in length. It can be as short as 3 amino acids in length, but more preferably is at least 6 amino acids in length. Where the interaction-dependent protein system uses a circularly permutated marker protein, the short spacer linking the fragment pair allows for the functional folding of the N- and C-terminal segments into the marker protein of interest. The length of the short spacer is determined by the separation of the N- and C-termini in the natively folded parent marker protein. To ensure flexibility and to avoid introducing steric hindrance that can interfere with the independent folding of the fragment domain and the interactor domain, the linker or spacer should be comprised of small, preferably neutral residues such as Gly, Ala and Val, but also can include polar residues that have heteroatoms such as Ser and Met, and can also contain charged residues.

The first interactor domain is a known or unknown protein or protein fragment that binds directly or indirectly through a third oligopeptide to a second target interactor domain that is an unknown protein or protein fragment and either or both the first and second interactor domain can be a member of a library. The interactor domain libraries are preferably constructed from cDNA, but can also be constructed from, for example, synthetic DNA, RNA and genomic DNA. The libraries can encode any representative synthetic or naturally occuring polypeptide population of interest. For example, a library can represent the entire proteome of a cell of interest, or a natural or synthetic antibody repertoire such as a single chain variable region library or a light chain variable region library, or a randomly generated peptide library presented in the context of thioredoxin. For the interaction-dependent enzyme activation systems presented herein, the reconstitution of the N-terminal and C-terminal segments into the marker protein preferably requires the prior interaction of the first and second interactor domains, or the first and second interactor domains with a third interactor or ligand. Bound interactor domains are identified by expressing a functionally reconstituted marker protein, and then the nucleotide sequences encoding for bound interactor domains or the bound interactor domains themselves are characterized by methods including electrophoresis, polymerase chain reaction (PCR), nucleotide and amino acid sequencing and the like.

Advantages of the present invention over previously disclosed interaction-dependent enzyme activation systems include a reporter protein that provides for a directly detectable signal upon reassembly, and background levels of 1 in $10^6$ or less. The specificity of the IdEA systems of the present invention are presented herein as activity or plating efficiency, activation index, or signal-to-noise ratio. The present IdEA systems demonstrate plating efficiencies of between 0.01-1.0 colonies per cell, activation indexes between $10^3$-$10^7$, and signal-to-noise ratios in the range of 100:1 to $10^6$:1. Activity and activation index are independent parameters, where a high activation index is desirable for intracellular assays and maximum activity is desirable for in vitro purposes. For identifying the interaction of intracellular polypeptides, an activation index of at least $10^3$, preferably at least $10^4$, more preferably at least $10^5$, and most preferably at least $10^6$ is desirable. An activation index as high as $10^7$ has been demonstrated with the IdEA systems described herein. For in vitro applications, an activity or plating efficiency of at least 0.01, preferably at least 0.1, more preferably at least 0.3, and most preferably at least 0.9 colonies per cell is desirable. A maximum plating efficiency of 1.0 colonies per cell can be achieved.

Additionally, the invention provides for rationally incorporated enhancement modifications to the fusion oligopeptides that increase the functional activity of the reconstituted protein to wild-type levels by improving folding and reassembly of the fragments into the parent protein, while at the same time maintaining dependence on the interactor domains for reassembly. The reassembled marker protein can provide as much as 60%, preferably at least 70%, more preferably at least 80% and most preferably at least 90% of the activity provided by the wild-type parent marker protein. The subject invention provides for enhancing the performance of the reassembled parent protein in the interaction-dependent enzyme activation systems presented by introducing at least one of the following modifications, including: i) a randomly-encoded peptide of 3-12 amino acids between the break-point terminus of each fragment and the flexible polypeptide linker, ii) a randomly-encoded peptide of 3-12 amino acids expressed separately as a fusion to the N-terminus of a thioredoxin with an intervening flexible linker, iii) a cysteine residue encoded at or within 5 amino acid positions of the break-point and between the break-point terminus of each fragment and the flexible polypeptide linker so that a disulfide bond can form between the members of a fragment pair, and iv) 1-3 codon changes within a member of a fragment pair introduced, for example, by PCR amplification of a nucleotide sequence encoding for a member of a fragment pair under error-prone conditions, to enhance the folding stability of a functionally reconstituted marker protein. Enhancement modifications such as a cysteine or a randomly encoded peptide of from 3-12 amino acids are preferably added within 10 amino acid residues, more preferably within 5 amino acid residues, and most preferably within 3 amino acid residues of the break-point termini. These performance enhancing modifications can be used for interaction-dependent enzyme activation systems that employ separately expressed marker protein fragment pair-interactor domain fusion proteins, and for circularly permutated marker proteins fused through each break-point termini to an interactor domain.

It is a unique advantage of the interaction-dependent enzyme activation systems of the present invention that they have been demonstrated to detect protein-protein interactions in cellular compartments in addition to the cytoplasm, such as the bacterial periplasm. Within a eukaryotic system, the inclusion of an appropriate N-terminal signal peptide can direct marker protein fragment pairs or interaction dependent circular permutations to the nucleus, endoplasmic reticulum and associated secretory compartments such as the Golgi, and to the extracellular membrane. The interaction-dependent enzyme activation systems of the subject invention also can be used to detect in vitro protein interactions, such as in cell lysates, or the interactions of intracellular or extracellular proteins of a host cell. For evaluating interactions between extracellular proteins, the first and second fusion oligopeptides can be expressed with an appropriate N-terminal signal peptide. In bacterial host cells, for example, an N-terminal signal peptide can provide for translocation of the fusion oligopeptides to the periplasm. It is preferred that the marker proteins of the present invention reassemble to form a monomeric enzyme, wherein the combined lengths of the N-terminal segment and the C-terminal segment can be discontinuous with residues around the break-point deleted, contiguous, or overlapping with residues around the break-point repeated, thereby comprising from 90% to 110% of the total length of the parent protein. Break-point termini are herein defined as the C-terminus of the N-terminal fragment and the N-terminus of the C-terminal fragment.

The invention is also directed to plasmids containing expression cassettes constructed to express fusion oligopeptides comprised of a fragment domain and an interactor domain. In a interaction-dependent enzyme activation system that utilizes marker protein fragment pair members on separate polypeptides, the expression cassettes for the N-terminal and C-terminal fragment pair members are designed with their components in different sequential orders. For the C-terminal fragment pair member, the expression cassette will comprise as operably linked components in the direction of transcription nucleotide sequences encoding for (i) a promoter functional in a host cell, (ii) a polypeptide interactor domain, (iii) a flexible polypeptide linker and (iv) a C-terminal fragment of a marker protein that provides for a directly selectable phenotype. The expression cassette for the N-terminal fragment pair member comprises as operably linked components in the direction of transcription nucleotide sequences encoding for (i) a promoter functional in a host cell, (ii) an N-terminal fragment of a marker protein that provides for a directly selectable phenotype, (iii) a flexible polypeptide linker and (iv) a polypeptide interactor domain. In a circularly permutated interaction-dependent enzyme activation system, both interactor domains are expressed as a single fusion protein from one expression cassette that comprises as operably linked components in the direction of transcription nucleotide sequences encoding for (i) a first interactor domain, (ii) a circularly permutated marker protein and (iii) a second interactor domain. The invention is also concerned with host cells that contain plasmids having the nucleotide sequences of the above-described expression cassettes.

Appropriate host cells for application of the subject invention include both eukaryotic cells, such as mammalian, yeast and plant cells, and prokaryotic cells, such as bacterial cells. A variety of prokaryotic expression systems can be used to express the fusion oligopeptides of the subject invention. Expression vectors can be constructed which contain a promoter to direct transcription, a ribosome binding site, and a transcriptional terminator. Examples of regulatory regions suitable for this purpose in *E. coli* are the promoter and operator region of the *E. coli* tryptophan biosynthetic pathway as described by Yanofsky (1984) *J. Bacteriol.*, 158:1018-1024 and the leftward promoter of phage lambda (Pλ) as described by Herskowitz and Hagen, (1980) *Ann. Rev. Genet.*, 14:399-445. Vectors used for expressing foreign genes in bacterial hosts generally will contain a sequence for a promoter which functions in the host cell. Plasmids useful for transforming bacteria include pBR322 (Bolivar, et al, (1977) *Gene* 2:95-113), the pUC plasmids (Messing,(1983) *Meth. Enzymol.* 101:20-77, Vieira and Messing, (1982) *Gene* 19:259-268), pCQV2 (Queen, ibid.), and derivatives thereof. Plasmids can contain both viral and bacterial elements. Methods for the recovery of the proteins in biologically active form are discussed in U.S. Pat. Nos. 4,966,963 and 4,999,422, which are incorporated herein by reference. See Sambrook, et al (*In Molecular Cloning: A Laboratory Manual*, 2$^{nd}$ Ed., 1989, Cold Spring Harbor Laboratory Press, Cold Spring Harbor) for a description of other prokaryotic expression systems.

For expression in eukaryotes, host cells for use in practicing the present invention include mammalian, avian, plant, insect, and fungal cells. As an example, for plants, the choice of a promoter will depend in part upon whether constitutive or inducible expression is desired and whether it is desirable to produce the fusion oligopeptides at a particular stage of plant development and/or in a particular tissue. Expression can be targeted to a particular location within a host plant such as seed, leaves, fruits, flowers, and roots, by using specific regulatory sequences, such as those described in U.S. Pat. Nos. 5,463,174, 4,943,674, 5,106,739, 5,175,095, 5,420,034, 5,188,958, and 5,589,379.

Where the host cell is a yeast cell, transcription and translational regions functional in yeast cells are provided, particularly from the host species. The transcriptional initiation regulatory regions can be obtained, for example from genes in the glycolytic pathway, such as alcohol dehydrogenase, glyceraldehyde-3-phosphate dehydrogenase (GPD), phosphoglucoisomerase, phosphoglycerate kinase, etc. or regulatable genes such as acid phosphatase, lactase, metallothionein, glucoamylase, etc. Any one of a number of regulatory sequences can be used in a particular situation, depending upon whether constitutive or induced transcription is desired, the particular efficiency of the promoter in conjunction with the open-reading frame of interest, the ability to join a strong promoter with a control region from a different promoter which allows for inducible transcription, ease of construction, and the like. Of particular interest are promoters which are activated in the presence of galactose. Galactose-inducible promoters (GAL1, GAL7, and GAL10) have been extensively utilized for high level and regulated expression of protein in yeast (Lue et al, (1987) *Mol. Cell. Biol.* 7:3446; Johnston, (1987) *Microbiol. Rev.* 51:458).

The invention also provides for efficient methods of identifying functional fragment pairs of a marker protein of interest that involves preparing a multiplicity of fragment pair members with break-point termini within a solvent exposed loop or a flexible loop defined by tertiary or secondary structure analysis to obtain a fragment pair library. To identify fragment pair members of interest, populations of fragment pair members are expressed in a multiplicity of host cells, and the host cells exhibiting the directly detectable signal associated with the marker protein of interest are isolated as indicative of containing fragment pair members that functionally reconstitute the marker protein. Plasmids containing expression cassettes coding for the fragment pair members are then sequenced to identify functional fragment pairs. To aid in the identification of functional fragment pair members of a marker protein of interest, the fragment pair members can be expressed as fusion proteins with interactor domains known to bind to each other, such as the fos and jun transcription factors that associate through a leucine zipper interaction. The sequences encoding the hetero-dimerizing helices of the fos and jun transcription factors are sufficient to use as effective interactor domain for this purpose.

The interaction-dependent enzyme activation systems and methods of the subject invention find particular use in identifying epitopes recognized by immunoglobulin molecules, polypeptide sequences that bind to extracellular domains of a transmembrane protein, inhibitors of phosphorylation-regulated signal transducer proteins, and interaction between oligopeptides of two different proteomes. For the identification of epitopes, first and second fusion oligopeptides comprised of a fragment domain and an interactor domain are expressed in a host cell where the first fusion oligopeptide has an interactor domain comprised of a randomly encoded peptide inserted into the active site of a thioredoxin protein and the interactor domain of the second fusion oligopeptide is comprised of a single-chain variable region (scFv) or antibody light chain variable region (VL). A similar strategy is followed for identifying polypeptide sequences that interact with the extracellular domain of a transmembrane protein, where the first interactor domain is comprised of a randomly encoded peptide inserted into the active site of a thioredoxin protein and the second interactor domain is comprised of a transmembrane protein. Identification of inhibitors of a phosphorylation-regulated signal transduction protein involves expressing a first fusion oligopeptide with a first interactor domain comprised of a phosphorylation-regulated signal transduction protein, such as Her-2/neu, and a second fusion oligopeptide with a second interactor domain comprised of a scFv or antibody light chain variable region that only binds to the unphosphorylated signal transduction protein. Inhibitory compounds are identified from host cells that change color in the presence of a chromogenic β-lactamase substrate. For identifying or monitoring polypeptide-polypeptide interactions between the members of two different proteomes, members of a first and second cellular expression library comprise the first and second interactor domain, respectively, of a fusion oligopeptide. The expression library is preferably a cDNA library, but can also be constructed from synthetic nucleotides to screen randomly generated polypeptides. A library of particular application for the present invention should represent all the protein members of a proteome of interest. Libraries derived from nucleotide sequences that all members of a total protein population (i.e. a proteome) of interest can be isolated from a host cell such as a prokaryotic or a eukaryotic cell, or also from a viral host. Viral hosts that encode for oncogenes are of particular interest. Mammalian tumor cells, immune cells and endothelial cells also provide proteomes of particular interest for the subject invention.

The invention also finds use in selecting with a single marker protein the incorporation of multiple genetic traits in a host cell, where detectable expression of a functionally reassembled marker protein is indicative of co-expression of multiple genes that encode for individual traits in a host. Finally, the invention provides therapeutic utility in a method for specifically activating derivitized prodrugs in the vicinity of a target organ in a host, where each member of a marker protein fragment pair is expressed as a fusion protein with individual immunoglobulin molecules that recognize neighboring but non-overlapping epitopes on a target protein. Binding of both antibodies to the target protein allows functional reconstitution of the marker protein which then activates subsequently administered prodrug only in the vicinity of a target organ.

The invention is exemplified by the antibiotic resistance enzyme, TEM-1 β-lactamase, although fragment pairs of other enzymes that provide for antibiotic resistance are included in the present invention, including: aminoglycoside phosphotransferases, particularly neomycin phosphotransferase, chloramphenicol acetyl transferase, and the tetracycline resistance protein described by Backman and Boyer (*Gene* (1983) 26:197). Other proteins that can directly elicit a visible phenotypic change such as a color change or fluorescence emission also are applicable to the subject invention. Examples of such proteins include β-galactosidase and green fluorescent protein (GFP) or other related fluorescent proteins.

Figure 3:
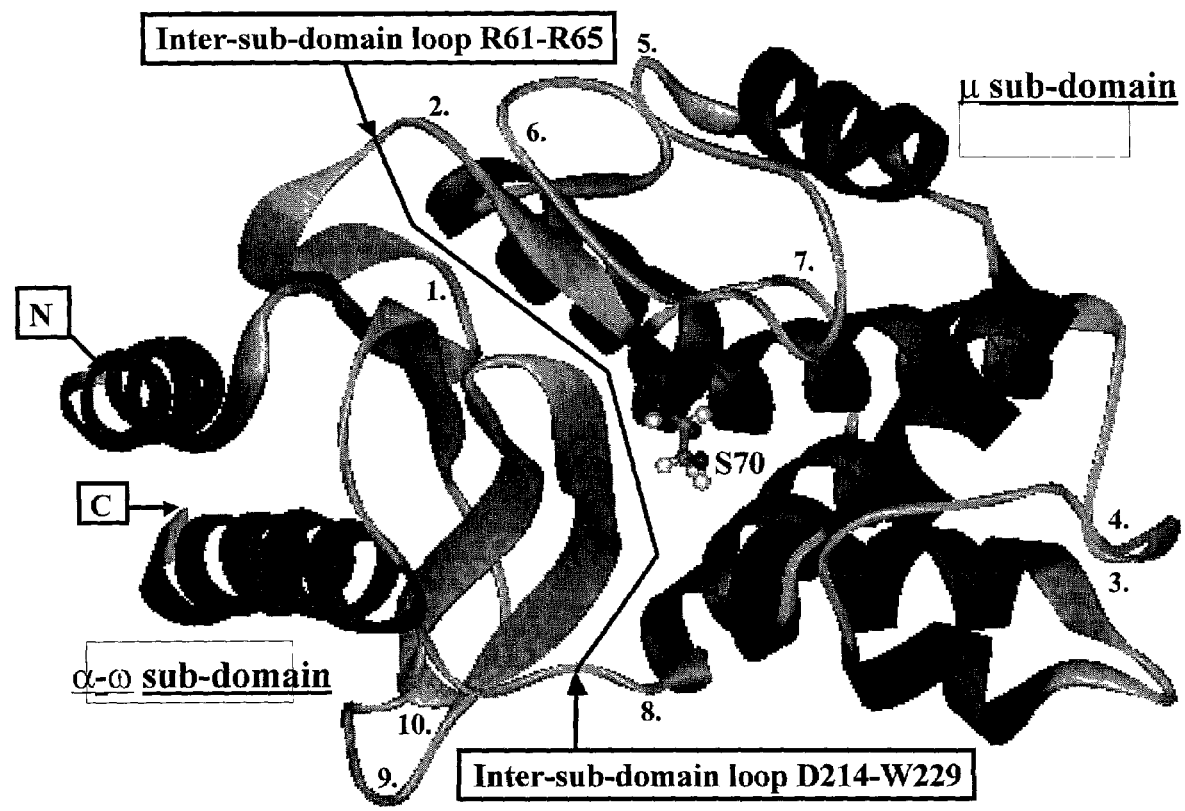
FIG. 3 shows the three-dimensional structure of mature TEM-1 β-lactamase. Rendering of the x-ray crystal structure of Jelsch et al. ($Proteins$ $Struct$ $Funct$ (1993) 16:364ff), using horizontally hatched and dotted ribbons to show α-helix and β-sheet, respectively. The molecule is oriented to emphasize the two-domain structure (α-ω and μ). The active site nucleophile, Ser70, is shown as a ball-and-stick model.

The TEM-1 β-lactamase of *E. coli* is the 264 amino acid product of the ampicillin resistance gene of plasmid pBR322 (Sutcliffe, 1978, supra), the nucleotide sequence of which is shown in FIG. 2 along with the encoded amino acid sequence. TEM-1 is the archetype member of the homologous Class A β-lactamases, or penicillinases. Its three-dimensional structure is shown in FIG. 3 (Jelsch et al., *Proteins Struct Funct* (1993) 16:364ff). The Class A β-lactamases are comprised of two domains. One domain, α-ω, is made up of N-terminal and C-terminal sequences, which form an anti-parallel two-helix bundle packed against a flat 5-stranded β-sheet. The inner face of the sheet packs against the other domain (μ), a seven helix bundle with two extended loops and two small β-structures. An outside strand of the β-sheet borders the substrate binding pocket, opposite the catalytic nucleophile, Ser70, and contributes substrate-binding residues. The remainder of the active site residues, including Ser70, are contributed by the μ domain. The two domains are connected by two loops: R61-R65 and D214-W229.

The subject invention also provides a method of identifying optimal break-points in a parent protein that provides for a directly detectable signal. A search of the "fragment space" of TEM-1 β-lactamase was conducted to identify fragment pairs which complement for activity only when the break-point termini of the fragments were genetically fused to hetero-dimerizing helixes from the c-fos and c-jun subunits of the AP-1 transcription factor (Karin et al., *Curr Opin Cell Biol* (1997) 9:240. To do this, libraries of all possible N- and C-terminal fragments of the enzyme were generated by progressive exonucleolytic digestion of the full coding sequence from both termini. Fragments of less than 25 amino acids were considered non-viable. When libraries were constructed with compatible vectors, the fragment sequences co-expressed in the same *E. coli* cells so that each cell expressed a single pair of N- and C-terminal fragments and every possible pair can be represented. For example, for a 100 kDa enzyme there are only $10^6$ possible N- and C-terminal fragment pairs, so an exhaustive search of the fragment space of most enzymes can be conducted with libraries of a manageable size.

Figure 4:
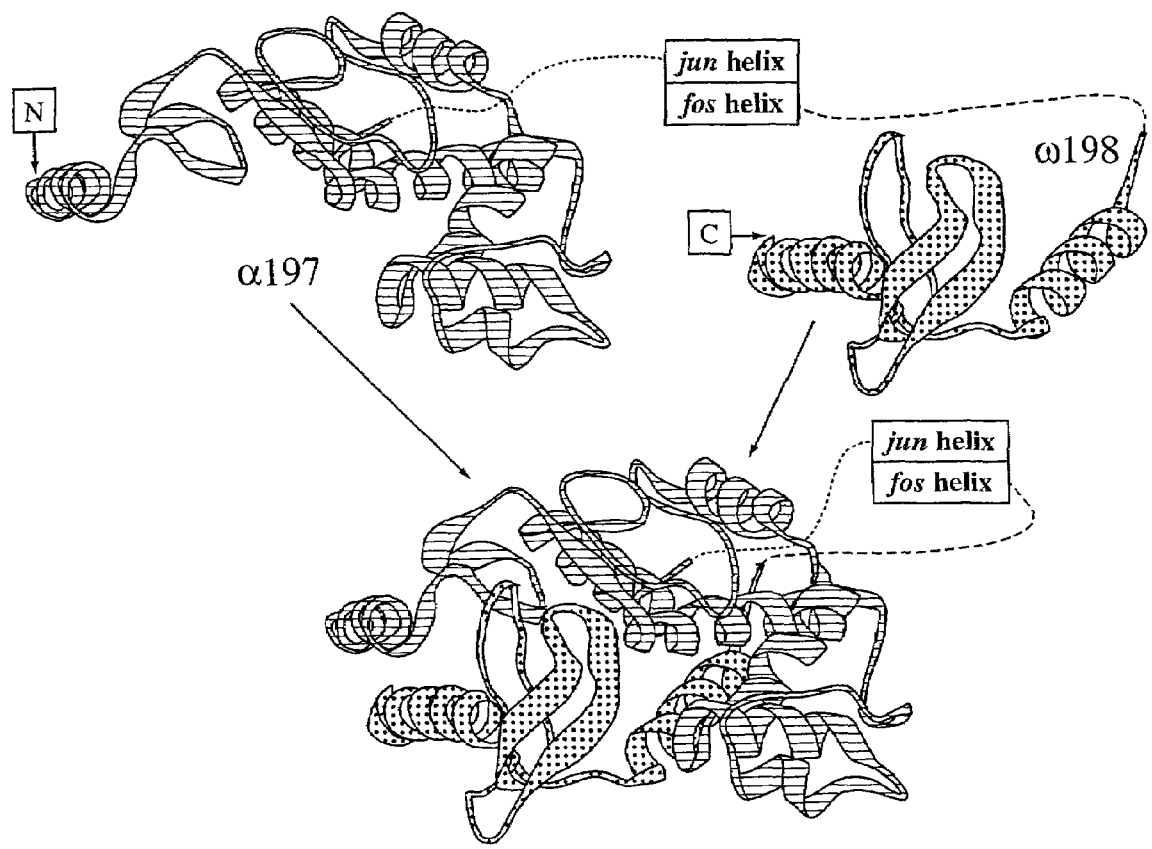
FIG. 4 shows the three-dimensional representation of interaction-dependent activation of β-lactamase by fragment complementation. Complementation of TEM-1 α197 and ω198 fragments by the interaction of the hetero-dimerizing helixes from the fos and jun subunits of the AP-1 transcription activator allows re-folding of the fragments into the active conformation of the enzyme (compare with FIG. 3). Activation can be enhanced by formation of a disulfide near the break-point.

An exposed loop was identified by this method between two (α-helixes of *E. coli* TEM-1 β-lactamase (approximately Thr195 to Ala202, between helixes 7 and 8) within which the chain can be broken to produce fragments which only complement for activity when fused to the fos and jun helixes. Representative fragments with contiguous break point termini at Glu197 and Leu198 were designated α197 (N-terminal fragment) and ω198 (C-terminal fragment), and subsequently shown to produce selectable activity in the *E. coli* periplasm with interactions between a variety of heterologous domains fused to the break-point termini, including single-chain antibody Fv fragments (scFv), antibody light chains (LC), thioredoxin with 12-mer peptides inserted into the active site (trxpeps), and the extra-cellular domain of the B-cell activation antigen CD40 (CD40ED). Activation by complementation of α197 and ω198 can also be driven by interaction of the heterologous domains with a third polypeptide, such as a receptor. Contiguous break-point termini of interest in *E. coli* TEM-1 β-lactamase in addition to E197/L198 include amide-bond junctions between amino acid residues N52/S53, E63/E64, Q99/N100, P174/N175, K215/V216, A227/G228, and G253/K254. The combined lengths of the N- and C-terminal segments can be discontinuous or overlapping, however, should comprise from 90% to 110% of the total length of the parent protein, and the actual break-point can be within ten amino acid residues in either direction from an identified functional contiguous break-point junction. The specific activity of the reconstituted enzyme can be enhanced to near wild-type levels by the interaction-driven formation of a disulfide at the break-point, which restores the integrity of the native polypeptide backbone (see FIG. 4). It is further shown that the α197 and ω198 fragments can be tethered together by a flexible linker between the native termini to produce a circular permutation, which is inactive except when an interaction occurs between heterologous domains fused to the break-point termini, or between these domains and a second polypeptide, such as a receptor. As with fragment complementation, the specific activity of the circular permutation can be enhanced to near wild-type levels by the interaction-driven formation of a disulfide at the break-point (see Table 6, below).

The β-lactamase α197 and ω198 fragments cooperatively produce selectable activity in the bacterial periplasm in a manner that is strictly dependent on specific interaction between heterologous domains fused to the break-point termini of the fragments is an example of an enzyme-based molecular interaction sensor that can undergo secretory translocation across a plasma membrane into an extra-cellular compartment, and therefore can reliably detect interactions between and among extra-cellular proteins.

The interaction-dependent enzyme association systems of the present invention find use in many applications in human therapeutics, diagnostics, and prognostics, as well as in high-throughput screening systems for the discovery and validation of pharmaceutical targets and drugs.

Figure 5:
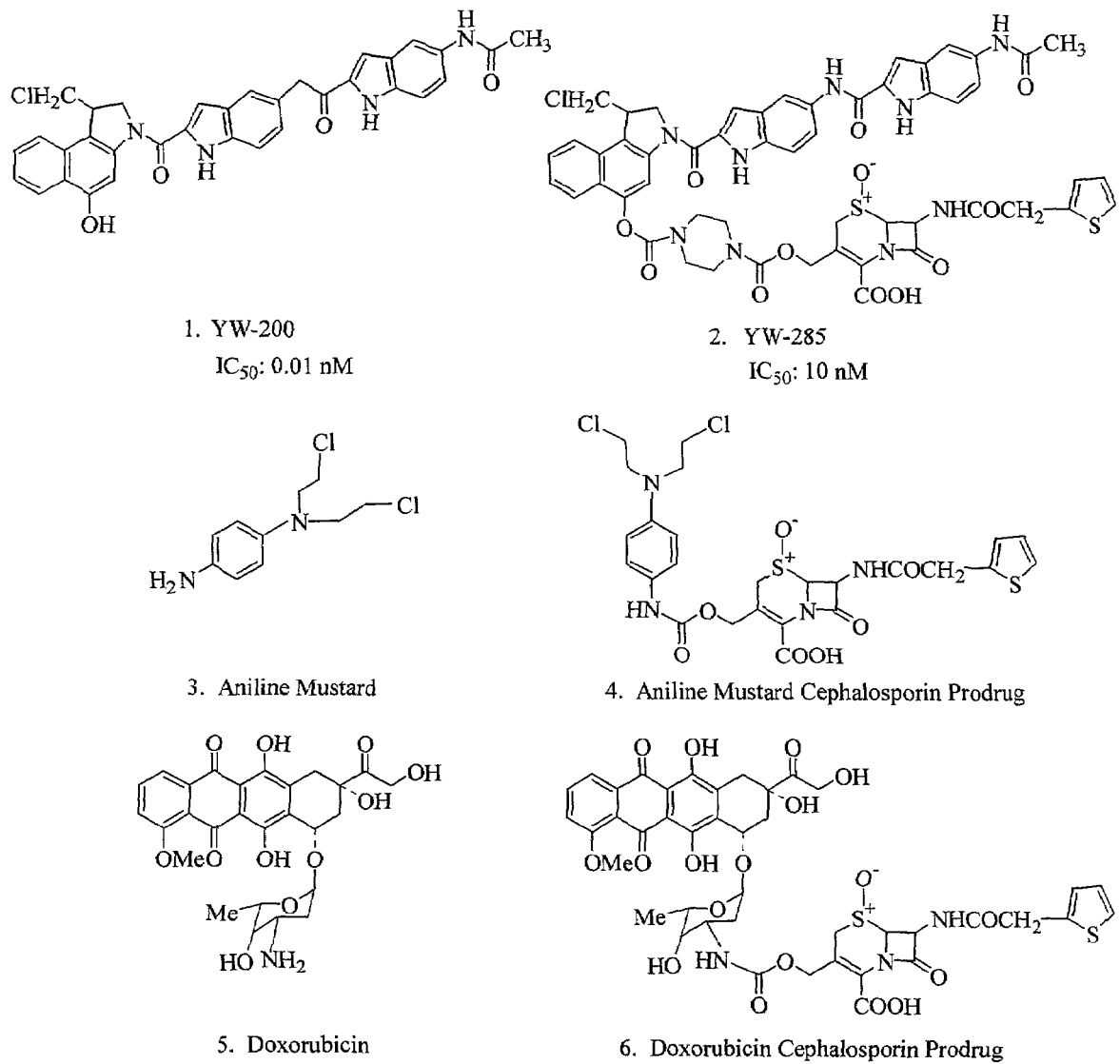
FIG. 5 shows the structures of some anti-cancer drugs and their cephalosporin prodrugs. YW-200 and YW-285 are a DNA-binding tri-indole and its cephalosporin prodrug (Wang et al., 1998, U.S. Pat. No. 5,843,937)

One particular application is concerned with the localized and controlled activation of inactive or weakly active compounds. For example, many useful compounds, such as drugs, chromophores, and fluorophores, can be inactivated by conjugation of an essential moiety on the compound, such as a hydroxyl or amino group, to a substrate for enzymatic hydrolysis, such as an ester, amide, carbamate, phosphate, glycoside, or glucuronide (Jungheim and Shepherd, *Chem Rev.* (1994) 94:1553). Such conjugates can then be activated by the appropriate hydrolytic enzymes such as esterases, carboxypeptidases, alkaline phosphatases, glycosidases, glucuronidases, β-lactamases, and Penicillin-amidases. In one particularly versatile system, cephalosporins can be conjugated at the 3' position via a variety of different leaving groups to a variety of anti-cancer drugs, such as nitrogen mustards, methotrexate, anthracyclines, and vinca alkaloids (Svensson et al., *J Med Chem* (1998) 41:1507; Vrudhula et at., *J Med Chem* (1995) 38:1380; Jungheim and Shepherd, 1994, supra; Alexander et al. *Tetrahedron Lett* (1991) 32:3269; see also FIG. 5). All of these are good substrates for broad spectrum β-lactamases, and most are much less active than their parent drugs. As a result, these prodrugs are promising candidates for use in Antibody-Directed Enzyme Prodrug Therapy (ADEPT; Bagshawe, *Drug Devel Res* (1995) 34:220). In addition to these compounds a vast array of antibiotics (Holbrook and Lowy, *Cancer Invest* (1998) 16:405), as well as a variety of chromogenic and fluorogenic substrates have been developed for β-lactamases (Jones et al., *J Clin Microbiol* (1982) 15:677; Jones et al., *J Clin Microbiol* (1982) 15:954; Zlokarnik et al., *Science* (1998) 279:84), making them one of the most versatile known classes of enzymes.

Nevertheless, the utility of such enzymes would be greatly enhanced if they were engineered so that their catalytic activities were positively controlled by allosteric interaction with ligands of choice. In this way the catalytic power of these enzymes can be harnessed to multiple new applications, including (1) rapid, ultra-sensitive detection of trace analytes and pathogens in biological specimens or in food, (2) targeted activation of therapeutic and diagnostic reagents at specific locations in the body, (3) rapid enrichment of expressed sequence libraries for autonomously folding domains (AFDs), (4) massive parallel mapping of pair-wise protein-protein interactions within and between the proteomes of cells, tissues, and pathogenic organisms, (5) rapid selection of antibody fragments or other binding proteins to whole proteomes, (6) rapid antigen identification for anti-cell and anti-tissue antibodies, (7) rapid epitope identification for antibodies, (8) high-throughput screens for inhibitors of any protein-protein interaction.

For example, enzymes which can be activated to hydrolyze chromogenic substrates only upon binding to target analytes could form the basis of assays for those analytes of unparalleled sensitivity and convenience. Such assays are homogeneous, requiring no manipulations other than the mixing of two components, namely the enzyme and substrate, with a biological specimen, in which the presence of the analyte is then quantitatively indicated by the rapid development of color. Current homogeneous enzymatic assays rely on inhibition of the enzyme by binding of anti-analyte antibody to the analyte, or mimic thereof, immobilized on the surface of the enzyme (Coty et al., *J Clin Immunoassay* (1994) 17:144; Legendre et al., *Nature Biotech* (1999) 1 7:67). Free analyte is estimated by its ability to competitively displace the antibody, thereby activating the enzyme. Such enzymes are thus activated competitively, not allosterically. For assays employing such enzymes the maximum signal increment occurs at equilibrium with roughly $K_d$ concentrations of reagents, so that typically only a fraction of analyte molecules participates in signal generation, and equilibration is often slow or does not even reach completion. However, an enzyme which is activated by direct allosteric interaction with analyte, can be used in excess, so that equilibration is rapid and independent of the analyte concentration, and the analyte can be saturated to produce signal from every molecule. In the case of microbial or viral pathogens, where unique surface markers can be present in hundreds to thousands of copies per cell or particle, such enzymes, which can be activated by binding to the marker, can allow rapid detection of as little as a single cell or particle, whereas the sensitivity of equilibrium assays for such analytes are typically much lower.

In another class of applications interaction-activated enzymes can be adapted for activation by binding to specific cell surface molecules. This allows the enzyme to become localized and activated at specific sites in the body for target-restricted activation of reagents for therapy or imaging. Antibody-Directed Enzyme Prodrug Therapy (ADEPT; Bagshawe, 1995, supra) is a promising chemotherapeutic strategy for the treatment of cancer, in which a prodrug-activating enzyme, such as a β-lactamase, is targeted to the tumor by a tumor-specific antibody to which it is chemically or genetically conjugated. After unbound conjugate has cleared the circulation, an inactive prodrug, such as an anthracycline cephalosporin, is administered, which is converted to a potent tumor-killing cytotoxin at the site of the tumor by the remaining tumor-bound enzyme. The main problem with ADEPT is that the unbound conjugate must clear the circulation before the prodrug can be administered in order to minimize systemic toxicity. However, by the time the conjugate has cleared the circulation >90% of the tumor bound enzyme has been lost (Bagshawe, 1995, supra; Springer and Niculescu-Duvaz, *Anti-Cancer Drug Design* (1995) 10:361). In spite of this, ADEPT has been able to achieve higher active drug concentrations in the tumor than any other procedure (Sedlacek et al., 1992 In *Contributions to Oncology*, Huber H and Queisser V, eds. pp. 208ff Karger, Basel), and has shown promise in the clinic (Bagshawe et al., *Dis Markers* (1991) 9:233; Springer and Niculescu-Duvaz, 1995, supra; Martin et al., *Cancer Chemother Pharmacol* (1997) 40:189). The unbound conjugate problem can be completely obviated by a prodrug-activating enzyme which is active only when bound to the tumor, so that the prodrug can be administered simultaneously with the enzyme or at the point of peak tumor loading without regard for unbound enzyme which is inactive.

In the same way, interaction-activated enzymes can be targeted for activation by surface markers on the cells of other types of diseased tissues, such as sites of inflammation or atherogenesis, or even healthy tissues. The target-localized and activated enzymes can then be used to activate not just cytotoxins, but other types of therapeutic agents such as small molecule agonists or antagonists of biological response modifiers, as well as imaging reagents for precise localization of tissue with disease or other phenotype of interest. For example, target-activatable enzymes can be used to deliver: (1) immune stimulants to tumors, (2) immuno-suppressants to sites of chronic inflammation or to organ transplants, (3) antibiotics to specific pathogens, (4) cytotoxins and anti-virals to virus-infected cells, (5) hormones and other pleiotropic agents to specific cells and/or tissues, or (6) neuro-transmitters and other neuro-modulators to specific nerves or tissues. In short, interaction-activated enzymes can be used to deliver to any tissue any small molecule cytotoxin, hormone, steroid, prostaglandin, neurotransmitter, or agonist/antagonist of peptide hormone, cytokine, or chemokine, etc., which can be inactivated by conjugation to the appropriate substrate.

In yet another class of applications, interaction-activated enzymes can be adapted for efficient simultaneous detection of multitudes of interactions among proteins within cells, including expressed sequence libraries, single-chain antibody fragment (scFv) libraries, and scaffolded peptide libraries. For example, enzyme-based interaction traps enable the comprehensive mapping of pairwise protein-protein interactions within and between the proteomes of human cells, tissues, and pathogens for the rapid identification and validation of new pharmaceutical targets. They also can be used for rapid selection of binding molecules from single-chain antibody fragment (scFv) libraries, or from scaffolded peptide libraries for use as reagents in functional genomics studies, or for identification of natural ligands and epitopes by homology. Target interactions identified using interaction-dependent β-lactamases can be used immediately to screen for inhibitors of the interaction by exploiting the great substrate diversity of these enzymes to reverse the polarity of selection. Whereas interaction-dependent activation of β-lactamase can be used to confer selective growth on host cells in the presence of β-lactam antibiotics, it also can be used to confer selective cytotoxicity on the cells in the presence of β-lactam pro-antibiotics. The latter substrates only become cytotoxic upon hydrolysis of the β-lactam moiety by the interaction-activated enzyme, and so can be used to select inhibitors of the interaction by their ability to confer selective growth on host cells.

Finally, enzyme-based interaction sensors can be used for rapid detection of the activation or inhibition of key molecular interactions in signal transduction pathways, enabling high-throughput cellular screens for inhibitors or activators of those pathways (i.e. kinases and phosphatases). For example, screening for agonists or antagonists of receptor tyrosine kinases usually requires coupling receptor ligation to a selectable phenotype which results from de novo gene expression. Such multi-step signal generating mechanisms are prone to high rates of false positive and false negative selection, like the yeast two-hybrid system, and are therefore poorly suited to high-throughput screening. However, interaction-dependent β-lactamases can be set up for activation by phospho-tyrosine sensitive interactions, so that a selectable phenotype is generated just downstream from receptor ligation. Interaction between the receptor tyrosine kinase substrate and a binder peptide can be designed to be either dependent on, or inhibited by phosphorylation, so that either receptor agonists or receptor antagonsists can be selected.

General Strategies for Making High-Performance Enzyme Fragment Complementation Systems The present invention provides for general strategies for the use of heterologous interactors, break-point disulfides, random tri-peptide libraries, and mutagenesis to obtain stable enzyme fragments which are capable of forming of catalytically robust complexes. It has been suggested that it might be possible to identify such fragment pairs for any enzyme simply by conducting thorough searches of all possible fragment pairs for the enzymes in question (Ostermeier et al., *Proc Natl Acad Sci* (1999) 96:3562). In practice, however, the success of such endeavors is strongly dependent on the stringency of selection, that is, how much functional enzyme must be produced by the expressed fragments to produce an efficiently selectable phenotype. An efficiently selectable phenotype is one in which the background frequency, or false positive rate, is not appreciably higher than the frequencies of the desired fragments in the fragment libraries.

In fact the most useful fragment complementation systems for a given enzyme are not necessarily those fragments of wild-type sequence which are most capable of unassisted complementation, but rather the most useful fragment complementation systems comprise those fragments which, when using the engineering techniques described, can be made to meet more specific performance requirements. For example, naturally evolved proteins are generally expected to exhibit a roughly inverse correlation between fragment stability and complex stability. This is due to the energy cost of inter-conversion. The more stable the fragments are, the more energy is required to form the complex and vice versa. As a result, those fragments capable of producing the highest specific activities might be missed or dismissed because fragment instability can prevent them from producing selectable levels of activity. To circumvent such pitfalls, libraries of fragment pairs can be simultaneously expressed with libraries of random tri-peptides to insure that every fragment pair has a chance to perform in the presence of fragment-stabilizing tri-peptides, thereby minimizing the dependence of the phenotype on fragment stability. This strategy is especially useful if dependence of activation on the interaction of heterologous domains fused to the fragments is desired. If constitutive activation is desired, the fragment libraries can also be amplified by error-prone PCR to introduce fold-accelerating mutations which can mitigate both fragment instability and complex instability, as was found for β-lactamase.

For in vitro applications such as homogeneous assays, biosensors, and target-activated reagents fragment stability is especially important, but the most stable fragments might not be selectable if they cannot produce stable complexes without assistance, as predicted by the inverse correlation of fragment stability and complex stability. Thus, fragment libraries can be expressed in the *E. Coli* periplasm with a disulfide at the break-points and heterologous interactors fused to the break-point termini. These tools provide mechanisms for docking the fragments, accelerating folding, and stabilizing the active complex. As was shown with β-lactamase, a substantial fraction of fragment pairs can be made to produce robust selectable activity in the bacterial periplasm with such molecular prostheses.

Each of the four tools described for enhancement of functional reconstitution of the parent protein of the fragment pairs, i.e., heterologous interaction, break-point disulfide, tri-peptide stabilizers, and mutagenesis, can be used alone or in combination to insure selection of the best fragments for the desired application, and also to improve and optimize the performance of selected fragment pairs for a desired application. As demonstrated, each tool enhances performance by a different mechanism, so that the effects of multiple tools are generally additive. Heterologous interactors bring and hold the fragments together to facilitate re-folding into the active complex. Break-point disulfides can stabilize the active fold by restoring the integrity of the polypeptide backbone at the break-point. Tethered or free tri-peptides can protect the fragments from aggregation without interfering with folding into the active complex. Mutagenesis can protect the fragments by accelerating folding into the active complex.

Figure 6:
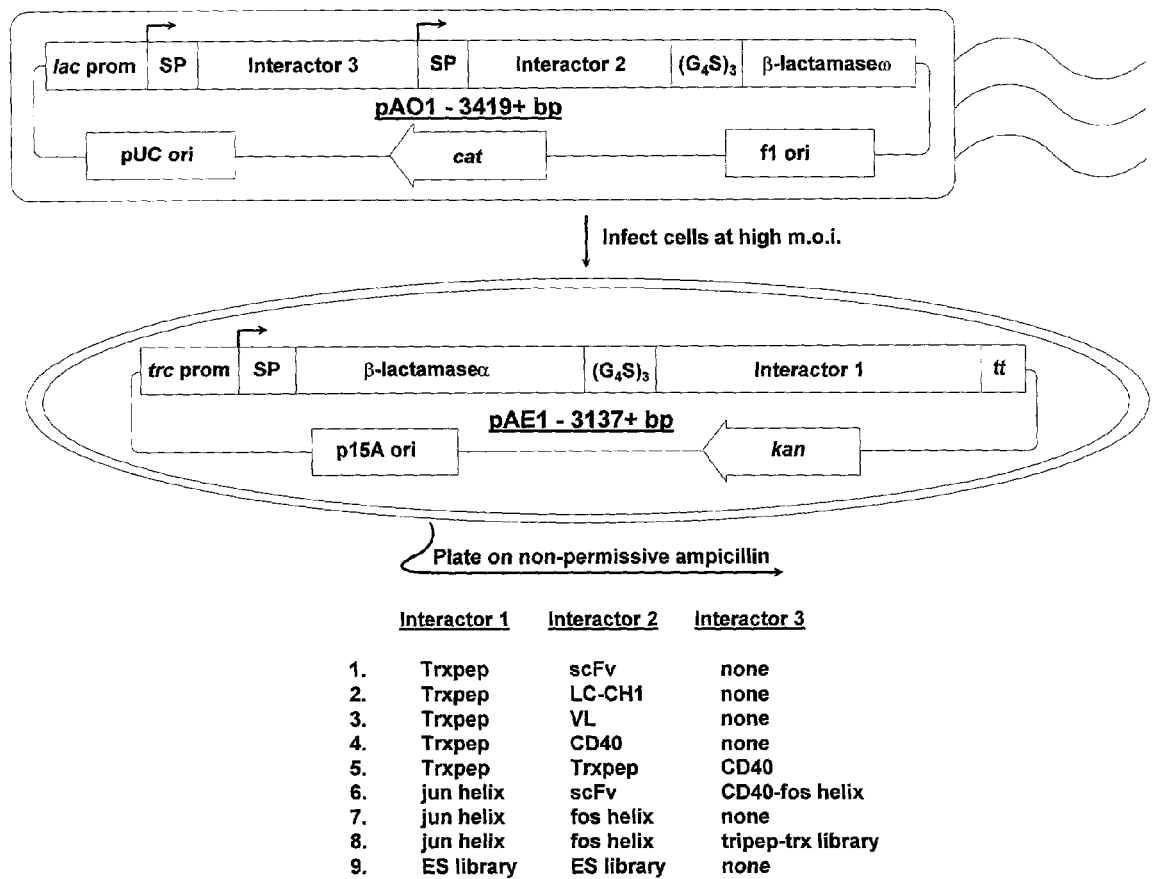
FIG. 6 shows vectors and strategy for the expression of heterologous proteins as fusions to the α197 and ω198 fragments of TEM-1 β-lactamase for interaction-dependent β-lactamase activation by fragment complementation. Vector pAO1 is a high-copy pUC119-based phagemid for expression of ω198 fusions and free ligands from dicistronic transcripts, which can be rescued as phage for quantitative introduction into host cells by high-multiplicity infection. Vector pAE1 is a low-copy p15A replicon with a strong promoter for expression of α197 fusions at comparable or higher levels than expression from the pAO1 vector. Trxpeps are 12-mer peptides inserted into the active site of thioredoxin. Tripep-trx libraries are random tri-peptides at the N-terninus of thioredoxin with an intervening Gly$_4$Ser (SEQ ID NO:3) linker. ScFv, single-chain antibody Fv fragment. LC-CH1, antibody fragment composed of light chain and first constant region of heavy chain. VL, antibody light chain variable region. lac prom, lactose operon promoter. SP, signal peptide. (Gly$_4$Ser)$_3$ (SEQ ID NO:4) flexible 15-mer linker. pUC ori, p15A ori, plasmid origins of replication. f1 ori, filamentous phage origin of replication. cat, chloramphenicol resistance gene. m.o.i., multiplicity of infection. trc prom, fusion promoter from tryptophan and lactose operons. tt, transcription termi

The first step in the development of high-performance enzyme fragment complementation systems is to construct vectors to express each fragment in the fragment pair library. A convenient system for selective fragment library expression can be derived from the expression system illustrated in FIG. 6. All fragment pairs regardless of the intended application can potentially benefit from and would not be impaired by the docking function provided by interactors such as the fos and jun helixes fused to the break-point termini. Thus, the C-terminal, or ω fragment library is expressed as N-terminal fusions via a flexible polypeptide linker such as a $(Gly_4Ser)_3$ (SEQ ID NO:4) linker to the fos helix (Interactor 2 in FIG. 6) from the lac promoter in the phagemid vector pAO1 (the upstream cistron can be removed if desired). The amino acid sequence of the flexible polypeptide linker is not critical, however, it must be of a sufficient length and flexibility such that the fragment domain and heterologous interactor domain fold independently and unhindered. The N-terminal, or α fragment library is expressed as C-terminal fusions via a flexible polypeptide linker such as a $(Gly_4Ser)_3$ (SEQ ID NO:4) linker to the jun helix (Interactor 1 in FIG. 6) from the trc promoter in the compatible pAE1 vector. Coding sequences for signal peptides are included if translocation to the periplasm is desired.

As discussed above, depending on whether the intended application(s) were in vitro or in vivo, or if in vivo, whether in the cytoplasm or secreted, one or more of the performance-enhancing tools can be incorporated into the expression vectors to maximize the probability of selecting the best fragment pair for the intended application(s). If periplasmic expression is desired, cysteines should be encoded at the break-point termini to allow disulfide formation. If the enzyme contains other cysteines, at least 1 mM and not more than 5 mM of a reducing agent such as GSH or DTT should be included in the growth medium to inhibit the formation of mixed disulfides. If fragment stabilization is desired to increase the importance of specific activity in selection, a random or VRK tri-peptide library can be encoded in frame with each fragment fusion between the break-point terminus and the flexible polypeptide linker. If VRK libraries were used for each fragment in a 50-fragment pair library, every possible tri-peptide-fragment combination can be contained in a combined library of $<10^8$. Alternatively, a single tri-peptide library can be used for each fragment pair in trans, as was described above. The tri-peptide library can be fused operably in frame via the flexible polypeptide linker to the N-terminus of thioredoxin and expressed from the upstream cistron in the pAO1 phagemid vector (see FIG. 6).

The second step in the development of high-performance enzyme fragment complementation systems is to construct an expression library of candidate enzyme fragment pairs. Methods for generating libraries of random fragment pairs have been described (Ostermeier et al., 1999, supra). However, such libraries are quite inefficient as the vast majority of fragment pairs will be dysfunctional. For combinatorial screening of fragment pair libraries with mutagenic or random tri-peptide libraries, much more efficient fragment pair libraries will be necessary. For a variety of reasons it can be assumed that the most functional fragment pairs will correspond to scission of the polypeptide chain in exposed regions between elements of secondary structure. Exposed break-points will be required for use of tethered heterologous interactors and tri-peptides, and scission within secondary structure elements can irreversibly destabilize such elements. If a 3-dimensional structure is available for the enzyme of interest, or for a homolog, it can be used to identify exposed loops as candidate sites for chain scission. Typical globular proteins will not have more than 20-25 such sites that are far enough from the ends so that the larger fragment is not independently active. This is a manageable number for construction of coding sequences for each fragment pair by PCR. Two end-specific primers are required, plus a head-to-head pair of primers for each break-point, which should be located more or less in the center of the exposed loop. If a 3-d structure is not available, reliable algorithms are available on the internet for computational prediction of secondary structure and hydropathy, such as the ProteinPredict program of Rost and Sander (*J Mol Biol* (1993) 232:584; *Proteins* (1994) 19:55; *Proteins* (1994) 20:216). With such programs, most of the exposed loops can be identified as hydrophilic regions between secondary structure elements. Again, it is not excessively burdensome to prepare coding sequences by PCR for up to 50 fragment pairs.

If fragment complementation does not need to be dependent on the direct or ligand-mediated interaction of heterologous domains fused to the break-point termini, then fold-accelerating mutations can also be selected by using error-prone PCR in the initial amplification of the fragment coding sequences. Under appropriate conditions of $Mg^{++}$, $Mn^{++}$, and nucleoside triphosphate concentrations, as well as cycle number, mutagenesis can be limited to 1-3 unbiased coding changes per molecule (Cadwell and Joyce, 1995, in *PCR Primer-A Laboratory Manual* C. Dieffenbach and G. Dveksler, Eds. Cold Spring Harbor Press, Cold Spring Harbor, N.Y., pp. 583-590). Since most mutations are non-phenotypic, this can easily be combined with the other performance-enhancing tools without compromising the selectability of optimal fragment-tri-peptide combinations. Once the fragment coding sequences have been amplified, gel-purified, and ligated into the vectors, the ligation products can be desalted and concentrated to allow efficient co-transformation of *E. coli* cells by high-voltage electroporation. If both the tri-peptide libraries and mutagenesis are used it is advisable to collect at least $10^8$ and preferably at least $10^9$ transformants to insure comprehensive representation of the full diversity of the library. The full library is then plated onto each of a range of non-permissive conditions, the least stringent being that on which the host cells plate with an efficiency not greater than ten times the inverse of the library size. This insures a manageable frequency of true positives among false positives. The maximum selection stringency is that above which nothing is recovered from the library.

If fragment complementation is to be dependent on the direct or ligand-mediated interaction of heterologous domains fused to the break-point termini, then mutagenesis should not be used because folding acceleration usually eliminates the need for docking assistance. In this case selected fragment pairs must be counter-screened for loss of activity in the absence of the fos-jun interaction and activation indexes must be determined as the ratio of interaction-dependent activity to interaction-independent activity. For interaction mapping within or between proteome libraries activation indexes of the order of at least $10^6$ are preferred since rare genes are expected to have frequencies in that range. For ligand-specific or interaction-specific biosensors lower activation indexes are usually acceptable. For example, to detect nanomolar concentrations of a ligand for which fragment-binder fusion affinities ($K_d$) are in the 10 nM range, the fragment binder fusions need only to be used at 100 nM concentrations to saturate the ligand. Under these conditions ~90% of the fragment-binder fusions will be unbound. If the activation index is >100, the background will be <10% of the signal.

Selected fragment pairs can be optimized for maximum activity and/or maximum activation index. In our experience break-point disulfides produce the highest specific activities because they allow the greatest amount of native structure in the fragment complex. However, they also may in the background so that activation indexes are often lower. To retain the specific activity benefit of the break-point disulfide and reduce the background one can retard the rate of disulfide formation so that it does not have sufficient time to occur during the abortive attempts of the unaided fragments to fold, but occurs efficiently when folding is catalyzed by the heterologous interaction. Two parameters can be adjusted to control the formation of break-point disulfides. (1) The proximity of the disulfide-forming cysteines to the break-point can be adjusted to place greater orientational stringency on disulfide formation. (2) The concentration of reducing agent in the medium can be increased to reduce the effective concentration of DsbA, the principle disulfide-forming oxidase in the periplasm.

It is possible to use TEM-1 β-lactamase fragment complementation to select fragment pairs of other proteins which do not produce selectable phenotypes in *E. Coli* for their ability to form stable complexes because such complexes will usually be in the native conformation and should be functionally active. It has been amply demonstrated that naturally evolved proteins have unique minimum energy conformations in which they are stable and active (Li et al., *Science* (1996) 273:666). All other conformations are unstable. Thus, if a fragment pair library of a non-phenotypic protein is expressed as fusions to the interaction-dependent TEM-1 β-lactamase fragments, it is expected that only those fragment pairs which associate and fold into the native conformation will provide sufficient docking function to facilitate selectable β-lactamase activation. In this case, the subject fragments serve the purpose of the heterologous interactors in facilitating complementation of β-lactamase fragments. However, additional modifications can be encoded into the fragment/heterologous interactor fusion sequences to enhance functional reassociation of the β-lactamase fragments, including a break-point disulfide, a randomly-encoded peptide of from 3-12 amino acids, and mutagenesis of several amino acids within the fragment domain. All of these tools specifically impact only complementation of the subject fragments by stabilizing the fragments, accelerating folding, and/or stabilizing the active fragment complex. Selected fragment pairs can then be tested individually for reconstitution of enzymatic activity or other function of the parental protein. In this way many useful fragment complementation systems can be developed for proteins which are active in eukaryotic cells, such as kinases or herbicide-resistance proteins.

The interaction-activated enzyme association systems of the subject invention, as exemplified by prokaryotic β-lactamase, find use in many applications as summarized below.

(1) Simplex and multiplex protein-protein interaction mapping. Simplex refers to the use of single bait proteins to fish natural interactors out of expressed sequence libraries. Multiplex refers to the combinatorial pair-wise interaction of two expressed sequence libraries for the purpose of simultaneously isolating as many natural interactions as possible. Individual interactors can be readily identified by nucleic acid hybridization.

(2) Interaction-dependent β-lactamase systems can also be used to enrich randomly-primed expressed sequence libraries for fragments which encode autonomously-folding domains (AFD). Interference with folding by the fusion partner is avoided by using epitope tags and hetero-dimerizing helixes only at the N- and C-termini of the expressed sequence, respectively. The CP or fragments can have N- and C-terminal anti-tag binder and the partner heterodimerizing helix. The disulfide switch can accommodate diverse interaction geometries.

(3) Simplex and multiplex selection of binding molecules such as single chain antibody fragments (scFv) and antibody light chain variable regions (VL). Non-immune human scFv repertoire libraries can be used with TEM-1 β-lactamase interaction-dependent activation systems to isolate scFv to single baits or simultaneously to expressed sequence libraries. In the latter case scFv specific for individual targets can be readily identified by nucleic acid hybridization.

(4) Interface mapping and ligand identification by mimotope homology. Constrained peptide libraries displayed on the surface of a carrier or "scaffold" protein can be used with β-lactamase interaction-dependent activation systems to isolate surrogate ligands for proteins or AFDs of interest. Consensus sequences from panels of such surrogate ligands for a given polypeptide can then be used to identify natural ligands of the polypeptide or interaction surfaces on natural ligands of the polypeptide. A common application of interface mapping is epitope mapping for antibodies, whereby the specific region to which an antibody binds on the surface of its antigen is identified.

(5) Bio-Action Sensors. The efficiencies of most screening systems for signal transduction agonists and antagonists are compromised by the need for multiple steps between receptor ligation and selectable phenotype generation, which usually requires de novo gene expression. Interaction-activated β-lactamases can be tailored for activation or inhibition by any component of a target signal transduction pathway to allow selection of agonists or antagonists of the pathway in any appropriate cell type without the need to wait for gene expression to generate a selectable phenotype.

(6) Homogeneous Assays. Interaction-dependent circular permutations or complementing fragments can be fused to two scFv or other binding molecules which bind non-overlapping epitopes on target molecules, so that β-lactamase activation becomes dependent on binding to the target ligand. The use of ligand-dependent β-lactamases in homogeneous assays for two-epitope analytes from proteins to pathogens affords unparalleled sensitivity because saturation kinetics can be used instead of the equilibrium kinetics required by most assays. The binding molecules can also be oligonucleotides which anneal to contiguous sequences in the genome of a target pathogen. Such sequence-activated β-lactamases can also be used for rapid quantitation of specific PCR products without the need for gel eletrophoresis.

(7) Target-Activated Enzyme Prodrug Therapy (TAcEPT) and Target-Activated Enzyme Imaging (TAcEI). Antibody-directed enzyme prodrug therapy is a promising chemo-therapeutic strategy in which patients are treated with prodrug-activating enzymes such as β-lactamase conjugated to tumor-targeting antibodies (Bagshawe, 1995, supra). When unbound antibody-enzyme conjugate has cleared the circulation, prodrugs can be administered which are preferentially activated at the site of the tumor. The efficacy of this therapy is severely limited by the need for unbound conjugate to clear the circulation before the prodrug can be administered in order to avoid excessive toxicity, during which time most of the bound enzyme is lost from the tumor. The use of tumor-activated β-lactamases allows the prodrug to be administered at peak tumor loading of the enzyme since the latter is inactive in the circulation, and can only activate the prodrug when bound to the tumor. The same strategy can be used for antibody-directed site-specific activation of reagents for imaging of tumors or other tissue pathologies, or for other therapeutic indications such as inflammation or transplant rejection.

The following examples are offered by way of illustration of the present invention, not limitation.

EXAMPLES

Figure 7:
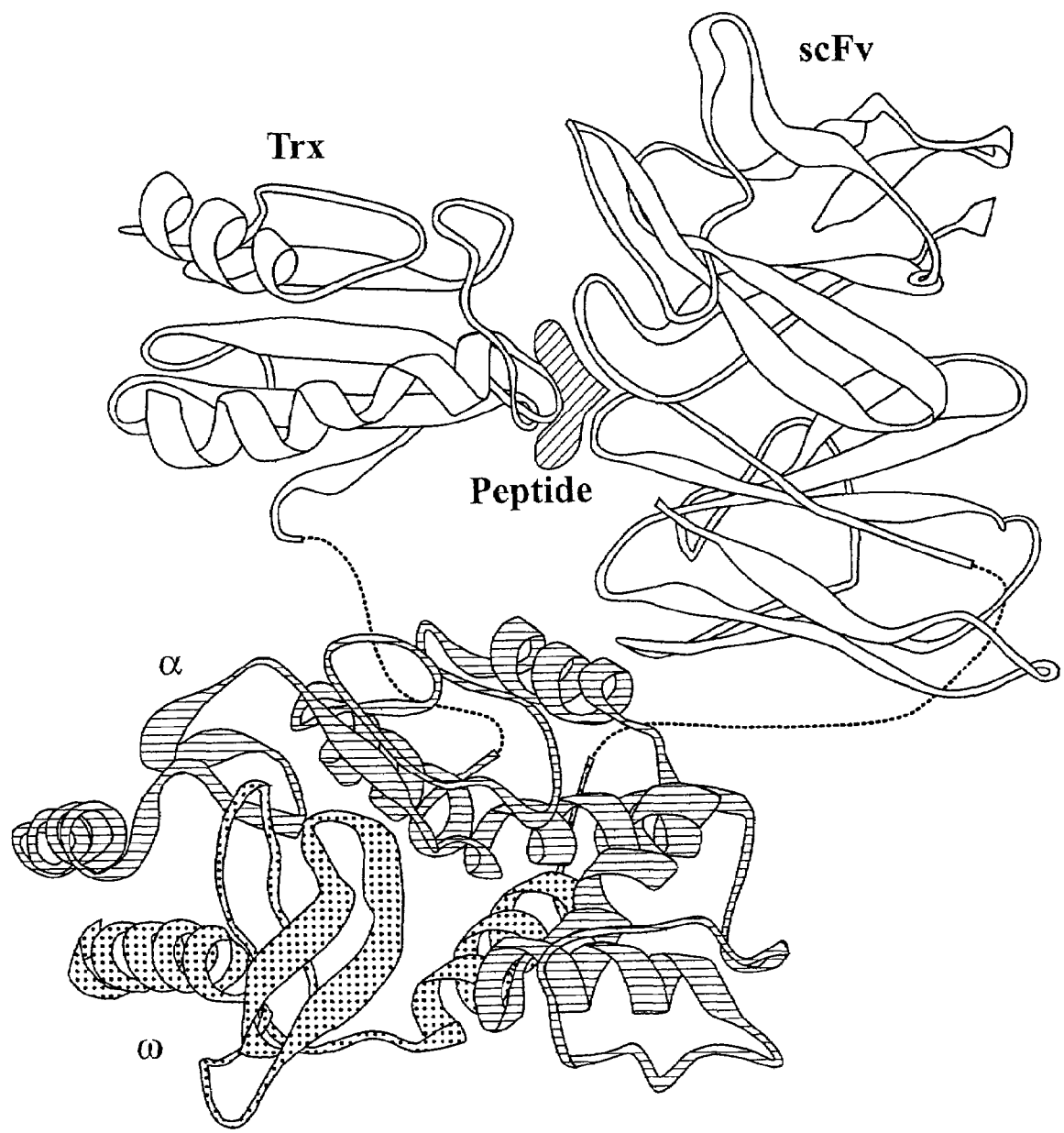

Example 1

β-lactamase Activation by Interaction-Mediated Complementation of α197 and ω198: Interactions between scFv and trxpeps This example demonstrates the ability of the system to detect and discriminate specific interactions between single-chain antibody Fv fragments (scFv) and 12-amino acid peptides inserted into the active site of *E. coli* thioredoxin (trxpeps, Colas et al., *Nature* (1996) 380:548). ScFv are comprised of antibody heavy chain and light chain variable regions (VH and VL) tethered into a continuous polypeptide by most commonly a $(Gly_4Ser)_3$ (SEQ ID NO:4) linker encoded between most commonly the C-terminus of VH and the N-terminus of VL.

scFv from a human non-immune antibody repertoire were amplified by PCR using a consensus primer mix (Marks et al., *Eur J Immunol* (1991) 21:985), and subcloned into a pUC 119-based phagemid vector (Sambrook et al., supra) for expression of the scFv as fusions to the N-terminus of the ω198 fragment with an intervening $(Gly_4Ser)_3$ (SEQ ID NO:4) linker (pAO1; see FIG. 6A). An N-terminal signal peptide was provided for translocation to the bacterial periplasm. A commercial trxpep library was obtained and amplified by PCR using primers specific for the N- and C-termini of *E. coli* thioredoxin (Genbank accession no. M54881). This product was subcloned into a p15A replicon (Rose, *Nuc Acids Res* (1988) 16:355) for expression as fusions to the C-terminus of the α197 fragment from the trp-lac fusion promoter (pAE1; see FIG. 6B). Again, an N-terminal signal peptide was provided for translocation to the periplasm. FIG. 7 illustrates the activation of TEM-1 by complementation of α197 and ω198, mediated by interaction between an scFv and a trxpep.

It was estimated that about 20% of the original scFv library clones produced soluble, full-length scFv as judged by immunoblot analysis (Harlow and Lane, (1988) *In Antibodies: A Laboratory Manual* Cold Spring Harbor Laboratory Press, Cold Spring Harbor) of periplasmic extracts obtained by osmotic shock (Neu and Heppel, *J Biol Chem* (1965) 240: 3685). Thus, approximately 60 clones had to be screened in this way to obtain twelve clones expressing functional scFv. Plasmid DNA representing these twelve clones of the scFv-ω198 construct was co-transformed with DNA representing approximately $5 \times 10^6$ clones of the α197-trxpep construct into *E. coli* strains DH5α and TG1 (Sambrook et al., 1989, supra), and plated onto solid LB medium containing kanamycin and chloramphenicol to determine the total number of co-transformants. Aliquots were also plated onto 25 μg/ml ampicillin (amp25). Out of approximately $1 \times 10^7$ total co-transformants, 40 ampicillin-resistant clones were recovered, 36 of which replated on amp25. A similar number of co-transformants of a single randomly selected α197-trxpep construct with the twenty scFv-ω198 constructs produced no colonies on amp25. All twelve scFv were represented in the 36 ampicillin-resistant clones with from one to five different trxpeps each. None of the 12 scFv cross-reacted with any trxpep originally selected by another scFv, as determined by co-transforming each scFv-ω198 construct with a pool of the α197-trxpep constructs selected by the other scFv. Thus, all 36 selected clones were bona fide positives, representing unique and specific scFv-trxpep interactions. No scFv bound thioredoxin in the absence of its peptide mimotope(s), and no selected trxpep bound common determinants on the scFvs. Selections were performed in the *E. coli* host strain TG1 without the gratuitous de-repressor of the lac promoter, isopropyl thiogalactoside (IPTG), so that transcription was minimal. When transcription was increased by the presence of 1 mM IPTG, many more colonies were obtained. Several of these were shown to be bona fide interactions which were too weak to confer selectable ampicillin resistance at lower levels of expression. Thus, the stringency of selection can be tuned by adjusting the expression levels of the interactors.

These results have several important implications. First, the false positive rate was exceedingly low, much lower than has been reported for other intra-cellular interaction sensors such as the yeast two-hybrid system (Bartel et al., 1993, supra; Bartel et al., 1996, supra). This property is essential for high-throughput applications. Secondly, the false negative rate with respect to the scFv was immeasurably low, as trxpeps were recovered for all functional scFv, and this too is essential for high-throughput applications. The fact that mimotopes were recovered for all scFv enables the system for high-throughput multiplex epitope mapping for scFv. Finally, the system is capable of efficient recovery of multiple interactions between two diverse populations of proteins simultaneously. Ultimately, given the high efficiency of the system, i.e., low rates of false positive and false negative selection, the throughput of the system should be limited only by the sizes of the interacting libraries, and/or the number of co-transformants which can be handled conveniently. For example, construction of recombinant protein libraries in the $10^9$-$10^{10}$ range is routinely possible for scFv, trxpeps, or cDNAs (Hoogenboom et al., *Immunotech* (1998) 4:1). Combinatorial pairwise interaction trapping for any two such libraries requires at least $10^{18}$-$10^{20}$ clones, but with quantitative phagemid infection methods (Sambrook et al., 1989, supra) and automated fermentation and plating methods, such throughput levels can be realistically achieved.

Example 2

β-lactamase Activation by Interaction-Mediated Complementation of α197 and ω198: Interactions between Antibody Light Chain V-Regions (VL) and Trxpeps This example demonstrates the ability of the system to work with larger antibody fragments, such as Fab, which are comprised of entire light chains disulfide-bonded to Fd fragments which contain VL plus the first heavy chain constant region. A subset of Fabs from a human repertoire library was subcloned for expression as C-terminal ω198 fusions from a dicistronic transcript from the lac promoter in the pAO1 vector (see FIG. 6A). The first cistron encoded the light chain with a signal peptide for translocation to the periplasm. The light chain termination codon was followed by a short spacer sequence and then a ribosome binding site approximately 10 bp upstream from the start of translation for the signal peptide of the Fd fragment, which was followed by ω198 with an intervening $(Gly_4Ser)_3$ (SEQ ID NO:4) linker. This construct was then co-expressed with the α197-trxpep library in the pAE1 vector in strains DH5α and TG1. Spontaneous association of the light chain with the Fd-ω198 fusion protein in the periplasm was expected to produce a functional Fab fragment. Binding of the latter to the peptide on a α197-trxpep fusion was then expected to facilitate assembly of the functional TEM-1 β-lactamase in amounts sufficient to confer selectable resistance to ampicillin on the host cells.

Many clones were in fact recovered on 25 μg/ml ampicillin. Some of these are listed in Table 1 below. Several were resistant to up to 100 μg/ml and one was resistant to up to 600 μg/ml. Unexpectedly, all recovered Fabs were missing the VH region. That is, they contained the full-length light chain (LC) with only the first heavy chain constant region (CH1). The reasons for this were as follows. The original Fab library was constructed by first inserting the VL repertoire into the vector which already contained the constant regions ready for expression. This intermediate construct was capable of expressing a complex of the light chain with the first heavy chain constant region fused to ω198. Plasmid DNA was then purified from this light chain library and used as the recipient for insertion of the VH repertoire to complete the Fab library. The resulting library was contaminated with approximately 15% of clones which contained the intermediate vector. Only these LC-CH1 complexes were capable of driving α97-ω198 complementation by binding of the VL combining site with the peptide on the appropriate trxpep. It is not known why full-length Fabs were not selected, however, the larger size and rigidity of the Fab-trxpep complex (~67 kDa) can have sterically inhibited fragment complementation, whereas the smaller size and flexibility of the LC-CH1 complex did not.

TABLE 1

Ampicillin-Resistance of TEM-1 β-lactamase α197/ω198 Fragment Complementation Driven by Interaction of Selected Pairs of Antibody Light Chain-CH1 Complexes and Trxpeps

| LC-CH1 | Trxpep | Amp[r] |
|---|---|---|
| P44-2-2B1 | P44-2-2A1 | [11]+++++ [a] |
| P44-2-3B1 | P44-2-3A1 | ++ |
| P44-1-6B1 | P44-2-6A1 | + |
| P64-17B1 | P64-17A1 | ++ |
| P65-1-10B1 | P65-1-10A1 | +++ |
| P66-3-2B1 | P66-3-2A1 | ++ |
| P66-3-10B1 | P66-3-10A1 | + |
| P66-3-14B1 | P66-3-14A1 | ++ |
| P75-7-7 | ? | ≧+ |
| P75-7-13 | ? | ≧+ |
| P75-7-30 | ? | ≧+ |

[a.] +, ++, +++, +++++, >10% plating efficiency on 25, 50, 100, 600 μg/ml ampicillin.

This result shows that light chain V-regions alone, which are only ~12 kDa in size, can make convenient high-affinity binding molecules for antigen-dependent activation of β-lactamase by fragment complementation. To test this, the VLs from several of the selected LC-CH 1 were subcloned for expression alone as C-terminal fusions to ω198. When each was co-expressed with its partner α197-trxpep, approximately one-third of the VL conferred selectable resistance to ampicillin comparable to the parent LC-CH1s.

Figure 8:
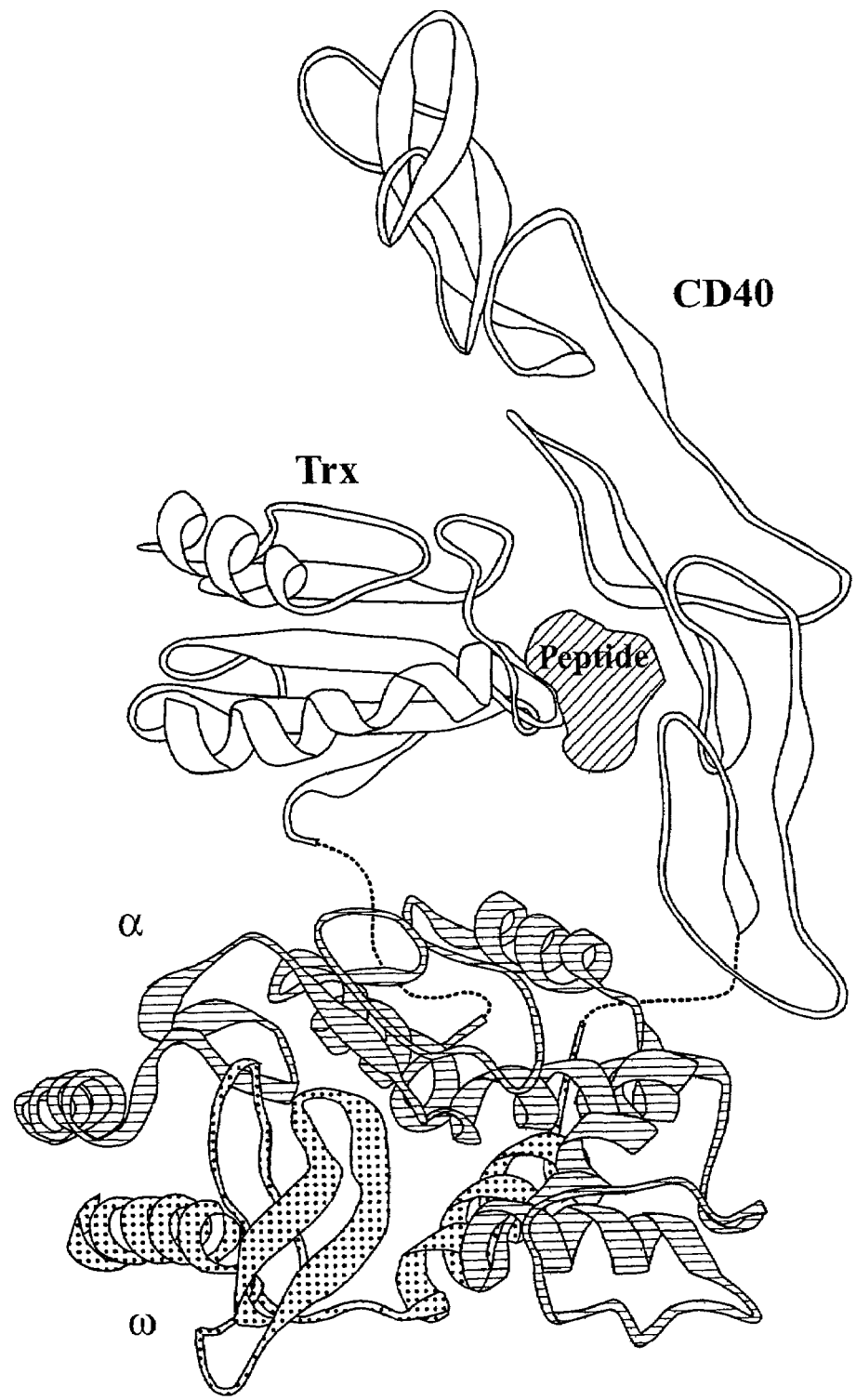

Example 3

β-lactamase Activation by Interaction-Mediated Complementation of α197 and ω198: Interactions between CD40 and trxpeps This example demonstrates the ability of the present system to isolate panels of trxpeps that bind to a given protein of interest, and which can be used to map interaction surfaces on the protein, and which also can assist in the identification of new ligands by homology. The extra-cellular domain of the human B-cell activation antigen CD40 is known to reliably express in the *E. coli* periplasm (Noelle et al., *Immunol Today* (1992) 13:431; Bajorath and Aruffo, *Proteins: Struct, Funct, Genet* (1997) 27:59). A T-cell surface molecule, CD40 ligand (CD40L), is known to co-activate B-cells by ligation to CD40, but there can be other ligands. Therefore, TEM-1 α197/ω198 fragment complementation was used to select a panel of CD40-binding trxpeps. The sequences of these peptides are then examined for homology to the known ligand and other potential ligands. The coding sequence for the mature form of the extra-cellular domain (CD40ED) was amplified by PCR using primers homologous to the N-terminus of the mature protein and to the C-terminus of the ~190-residue extra-cellular domain (Genbank accession no. X60592). The PCR product was then subcloned into the pAO1 phagemid vector (FIG. 6A) for expression from the lac promoter as a C-terminal fusion to the TEM-1 ω198 fragment with an intervening $(Gly_4Ser)_3$ (SEQ ID NO:4) linker. Expression of the correct product was confirmed by PAGE, and the CD40 fusion vector was then rescued as phage and transfected into TG-1 cells bearing the same trxpep library construct as described above. Approximately $10^7$ co-transformants were collected by double selection on kanamycin and chloramphenicol, and then plated onto 25 μg/ml ampicillin. Activation of TEM-1 by a trxpep-CD40 interaction-mediated complementation of α197 and ω198 is depicted in FIG. 8.

Ampicillin-resistant clones encoding thirteen unique trxpeps were recovered. In all cases amp resistance was strictly dependent on the presence of CD40ED and the peptide portion of the trxpep. No activity was seen if CD40ED was replaced with an irrelevant protein or if the trxpep was replaced by wild-type thioredoxin. The sequences of the selected CD40-binding peptides are shown in Table 2 below along with their homologies to each other and to CD40L. The thirteen peptides sort into eight homology groups: two groups with three each (1 and 2), one with two (3), and five with one each. Groups 1 and 2 are defined by homology of three peptides in each group to the same region of CD40L. Group 1 is homologous to the region of CD40L from Pro217 to Gly234, and Group 2 is homologous to the region from Gly158 to Leu168. Group 3 is defined only by interpeptide homology and has no detectable homology to CD40L. Group 4 is homologous to CD40L from Ser110 to Pro120, and Group 5 is homologous to CD40L from Pro244 to Gly257. Groups 6-8 have no discernable homologies. However, a number of the peptides had striking homology to other human extra-cellular proteins, including CTLA-2A, a matrix metalloproteinase, a receptor Tyr phosphatase, vascular endothelial cell growth inhibitor (VEGI), transferrin receptor, CD3ζ and bone morphogenetic protein 3B (BMP-3B). These can define an interaction motif or motifs, which have been used repeatedly for extra-cellular protein-protein interactions. They can also indicate multiple interaction sites on CD40.

Inter-trxpep competition was tested by expressing each of five selected CD40-binding trxpeps from a second cistron in the pAO1 phagemid vector, downstream from the CD40-ω198 fusion. Each of these constructs was then co-expressed with each of the same five plus three additional selected α197-trxpep fusion constructs in strain TG1 and scored for growth on 25 μg/ml ampicillin. The results are shown in Table 3 below. The eight trxpeps sorted into five groups. BW10-1 competes moderately with groups 2 and 3. p58-12-9A1, BW10-4, and BW10-8 compete strongly with each other and have similar competition profiles. They do not compete with group 3, except for BW10-8, which competes slightly with group 3 and BW10-9. All three compete with BW10-1, and p58-12-9A1 also competes slightly with BW10-9. p44-4-2A1 and p45-7-2A3 compete strongly and have similar competition profiles. They compete with BW10-1 and nothing else except BW10-8 slightly. BW10-9 competes slightly with BW10-8 and p58-12-9A1. p65-2-9A1 is inhibited by nothing.

TABLE 2

Homologies of Representative CD40-binding Trxpeps

| Group | TrxPep | Sequence[a] | SEQ ID NO: | Amp[r] |
|---|---|---|---|---|
| 1 | BW10-1 | CGPKELRIGGRPRRPGPC | 8 | +[b] |
|  | P58-12-9A1 | CGPEGQGGVAVGGVGGPC | 9 | + |
|  | P65-2-4A2 | CGPAKRADVEFSLEPG | 10 | + |
|  | CD40L | 215-AKPCGQQSIHLGGVFELQPGA-235 | 11 |  |
| 2 | BW10-9 | CGPKSAGKGRKDRRKGPC | 12 | ++ |
|  | P65-2-1A3 | CGPRTRVNHQGQKTRGPC | 13 | + |
|  | P65-2-2A5 | CGPAGAIRHEHRQGLGPC | 14 | + |
|  | CD40L | 152-LVTLENGKQLTVKRQGLYYTYAQ-174 | 15 |  |
| 3 | P44-4-2A1 | CGPDTGLETDAADASGPC | 16 | + |
|  | P45-7-2A3 | CGPRRVRETVAVESSGPC | 17 | + |
| 4 | BW10-4 | CGPPCATFEEAKSNQGPC | 18 | + |
|  | CD40L | 104-ETKKENSFEMQKGDQNPQ-121 | 19 |  |
| 5 | P65-2-8A3 | CGPGRESRGRCYTPSGPC | 20 | + |
|  | CD40L | 242-TDPSQVSHGTGFTSFGLL-259 | 21 |  |
| 6 | BW10-8 | CGPNTPDEEMAPQAPGPC | 22 | ++ |
| 7 | P65-2-5A4 | CGPVVHIKTNEQAAPGPC | 23 | + |
| 8 | P65-2-9A1 | CGPVAEEPAGGAGRPGPC | 24 | + |

[a] For sequence homologies, underlined denotes identity, bold denotes conservative substitution. For groups 1, 2, 4, and 5 homologies to CD40L only are depicted.
[b] Plating efficiencies when co-expressed with CD40-ω 198 fusion on 25 μg/ml ampicillin. +, >10%; ++, >50%.

TABLE 3

CD40 Trx-Peptide Competition

|  | B10-1 | B10-4 | B10-8 | B10-9 | P44-4-2A1 | P45-7-2A3 | P58-12-9A1 | P65-2-9A1 |
|---|---|---|---|---|---|---|---|---|
| B10-1 | + | +/+ | ±/+ | −/ | +/± | +/ | −/+ | −/ |
| B10-4 | +/+ | + | +/+ | −/ | −/± | −/ | +/+ | − |
| B10-8 | ±/+ | +/+ | + | ±/ | −/± | ±/ | +/+ | −/ |
| B10-9 | −/ | −/ | ±/ | (+) | −/ |  | +/ |  |
| P44-4-2A1 | +/± | −/± | −/± | −/ | + | +/ | −/ | −/ |
| P45-7-2A3 | +/ | −/ | ±/ |  | +/ | + |  |  |
| P58-12-9A1 | −/+ | +/+ | +/+ | +/ | −/ |  | + | −/ |
| P65-2-9A1 | −/ | −/ | −/ | −/ |  |  | −/ | (+) |

Group 1: B10-1
Group 2: P58-12-9A1, B10-8, B10-4
Group 3: P44-4-2A1, P45-7-2A3
Group 4: B10-9
Group 5: P65-2-9A1
1. "+" = inhibited, "−" = not inhibited. Read down/across
2. For all cells right of "+" diagonal, read down = free/across = α-fusion.
3. For all cells left of "+" diagonal, read down = α-fusion/across = free
4. (+) self control was not actually done.

In general, the competition data is consistent with the homology data with the caveat that simultaneous binding to non-overlapping epitopes is sometimes not tolerated. This allows unrelated sequences like p58-12-9A1 and BW10-8 to compete strongly with one another and have similar competition profiles. This is probably due to steric interference with enzyme reassembly, and can account for the discordance between homology and competition data for BW10-1 and p58-12-9A1 in particular. These two probably bind near the same CD40 interaction epitope, which can sterically inhibit fragment complementation for many (but not all) other trxpeps.

For some applications it will be useful for β-lactamase activation to be mediated by simultaneous binding of both α197 and ω198 to non-overlapping epitopes on a separate molecule, either a free ligand or cell surface receptor. Two CD40-binding trxpeps, which had been identified as non-competing by the competition tests, were used to test this utility. One of the two trxpeps was subcloned for expression as the C-terminal ω198 fusion from the pAO1 vector (see FIG. 6). The other trxpep was expressed as the α197 fusion from the pAE1 vector as before. Co-expression of these two constructs was used as the negative control. To test for CD40-mediated activation, the CD40ED coding sequence (including signal peptide) was subcloned into the trxpep-ω198 expression cassette between the promoter and the trxpep-ω9 198 sequence. An additional 20 bp containing a ribosome binding site was included downstream from the CD40 stop codon to allow expression of both CD40 and trxpep-ω198 from the same dicistronic transcript, as was described above for the Fab. As shown in Table 4 below, CD40 expression induced resistance to 50 μg/ml ampicillin, whereas without CD40 the cells expressing the control constructs produced fewer than $10^{-6}$ colonies per cell on 25 μg/ml ampicillin. Thus, β-lactamase fragment complementation can be efficiently induced by a tri-molecular protein-protein-protein interaction.

Example 4

β-lactamase Activation by Interaction-Mediated Complementation of α197 and ω0198: Interaction between a CD40-specific scFv and CD40

Since β-lactamase activation by α197-ω198 fragment complementation can be driven efficiently by interaction between scFv and trxpeps, it was important to show that it can also be driven by interaction between scFv and a bona fide protein antigen, preferably a cell surface receptor. This was especially important because the ligand-binding domains for type 1 trans-membrane receptors are N-terminal, therefore their expression as C-terminal fusions is preferred. However, the preferred orientation for scFv expression is also N-terminal. To allow expression of both scFv and antigen as C-terminal fusions, β-lactamase activation by a tri-molecular interaction was tested, including the C-terminal fusion of the scFv with ω198, a C-terminal fusion of CD40 with the fos helix, and a C-terminal fusion of α197 with the jun helix. The expression constructs were analogous to those used for CD40 ligation of the trxpep-fragment fusions. The CD40-fos fusion and the scFvω198 fusion were expressed from a dicistronic transcript in the pAO1 vector, and α197-jun fusion was expressed from the pAE1 vector. The fos-jun interaction has a $K_d$ in the $10^{-8}$M range, so it should quantitatively ligate CD40 with α197, which are much more abundant than this in the periplasm. Binding of the scFv to CD40 should then dock ω198 with the complex to facilitate fragment complementation. As shown in Table 4, CD40-fos expression induced resistance to up to 100 μg/ml ampicillin, whereas cells expressing only the control constructs without CD40-fos again produced fewer than $10^{-6}$ colonies per cell on 25 μg/ml ampicillin. Thus, β-lactamase fragment complementation can be efficiently induced by a tri-molecular interaction of two extra-cellular proteins in preferred C-terminal fusions.

TABLE 4

Ligand activation of TEM-1cpL198-197 or TEM-1 fragments α197 and ω198 by interaction of CD40 with non-competing CD40-binding peptides and interactions of the c-fox and c-jun leucine zipper helixes.

| Molecule#1 | Molecule#2 | Molecule#3 | $Amp^r$ |
|---|---|---|---|
| BW10-1-CP-p44-4-2 [b.] | – | – | +/– [a.] |
| BW10-1-CP-p44-4-2 | Vector control | – | +/– |
| BW10-1-CP-p44-4-2 | CD40 | – | +++ |
| BW10-1-CP-p44-4-2 | CD40-ω | – | +++ |
| BW10-1-CP | CD40 | – | – |
| BW10-1-CP | CD40-ω | – | – |
| CP-p44-4-2 | CD40 | – | – |
| CP-p44-4-2 | CD40-ω | – | – |
| CP-p44-4-2 | CD40 | BW10-1-CP | – |
| BW10-1-CP-fos [c.] | CD40-jun | – | +++ |
| fos-CP-p44-4-2 | jun-CD40 | – | +++ |
| α-p44-4-2 | CD40-ω | – | ++ |

TABLE 4-continued

Ligand activation of TEM-1cpL198-197 or TEM-1 fragments α197 and ω198 by interaction of CD40 with non-competing CD40-binding peptides and interactions of the c-fox and c-jun leucine zipper helixes.

| Molecule#1 | Molecule#2 | Molecule#3 | $Amp^r$ |
|---|---|---|---|
| α-p44-4-2 | CD40 | BW10-1-ω | ++ |
| α-p44-4-2 | – | BW10-1-ω | – |

[a.] plating efficiencies on 25 μg/ml ampicillin in colonies per cell. –, $<10^{-4}$; +/–, $10^{-4}$-0.01; +, 0.01-0.10 ++, 0.10-0.05; +++, >50%.
[b.] BW10-1 and p44-4-2 are 12-mer peptides in the active site of thioredoxin which were selected for binding to non-competing epitopes on the extra-cellular domain of the human B-cell antigen CD40.
[c.] fos and jun are the leucine zipper helixes from the c-fos and c-jun subunits of the AP-1 transcription factor.

Example 5

Disulfide-Enhanced Fragment Complementation

The β-lactamase activity produced by interaction-dependent complementation of the α197 and ω0198 fragments is substantially less than that of the wild-type enzyme under the same expression conditions. This loss of activity could be due to a tendency of the fragments to aggregate or turnover when they are not folded into the native conformation, and it could also reflect a loss of specific activity due to the reduced ability of the loosely tethered heterologous interaction to stabilize the native conformation. It was reasoned that both folding kinetics and stability could be enhanced by the introduction of a disulfide at the break-point, and this could lead to a substantial increase in interaction-dependent activity. The expectation was that when the fragments were docked by the heterologous interaction, the integrity of the polypeptide backbone is restored at some point in the folding pathway by the formation of a disulfide linkage between cysteines added at the break-point, and this accelerates folding and/or stabilize the active conformation. The disulfide forms very rapidly in the highly oxidizing environment of the bacterial periplasm. However, if the fragments were unstable until they were docked and folded, but once folded the activity was stable, then the break-point disulfide might have little effect on activity if it did not form until late in the folding pathway.

Cysteines were added to the sequences of α197 and ω198, between the break-point termini and the linkers leading to the heterologous interactors. With the fos and jun helices as the interactors, quantitative ampicillin resistance (>10% plating efficiency) increased from 50 μg/ml to more than 100 μg/ml, and the plating efficiency on 25 μg/ml ampicillin increased at least 2-fold. Thus, disulfide formation must be accelerating folding and/or stabilizing the active comformation. However, the disulfide produced nearly as much activity without the interactors. This contrasts sharply with the activity of the fragments in the absence of either the disulfide or interactors, for which plating efficiencies are less than $10^{-6}$ on 25 μg/ml ampicillin. This result suggests that the fragments probably associate and refold readily on their own at these intra-cellular concentrations, but that without a heterologous interaction or disulfide at the break-point, either folding cannot progress to the active conformation, or the latter is not stable enough to produce selectable activity. There must be a finite window of opportunity for disulfide formation when the thiols are proximal during unassisted folding. This window should be much wider during interaction-assisted folding. Thus, it should be possible to retard disulfide formation and thereby make it more dependent on the heterologous interaction.

Disulfide formation was made to be more dependent on the heterologous interaction by two modifications. First, disulfide formation can be inhibited by inclusion of a reducing agent in the growth medium. Dithiothreitol (DTT) at 10 mM reduced the plating efficiency of the disulfide-assisted fragments on 100 μg/ml ampicillin to $<10^{-4}$ colonies per cell in the absence of and interaction, whereas with the fos-jun interaction the activity of the same fragments was little affected by DTT, so that the activation index was increased to >1000-fold. Secondly, the cysteines were shifted by one residue each away form the break-point and into the β-lactamase sequence, so that they became separated in the native fold by an additional ~8 Å. This reduced activity to a plating efficiency of $<10^{-6}$ on 50 μg/ml ampicillin without the interaction, whereas with the fos-jun interaction the plating efficiency was reduced to ~10% on 50 μg/ml ampicillin for an activation index of $>10^5$. Thus, a combination of reducing agent and thiol separation can be expected to increase the increment of interaction-dependent activation over background even further, perhaps to $>10^6$. In any case the 8 Å increase in thiol separation alone increased the activation increment substantially over that of the fos-jun interaction without disulfide. The enhancement of interaction-dependent specific activity provided by the disulfide should allow weak interactions and/or poor expressors to produce selectable β-lactamase activity with fewer than 10 molecules per cell of the activated enzyme.

The ability of the break-point disulfide to enhance activation of TEM-1 α197/ω198 fragment complementation, suggests that break-point disulfides might be able to activate many enzyme fragment pairs which produce weak or no selectable activity with a heterologous interaction alone. The heterologous interaction can be essential for fragment docking, but since it is tethered with ~60 Å linkers it cannot restore the tight junction of the polypeptide backbone at the break-point. However, formation of a disulfide across the break-point should restore the integrity of the backbone, and should thereby help stabilize the active site of the complex. This idea was tested by screening nine additional pairs of TEM-1 β-lactamase fragments, corresponding to scission in nine exposed loops of the polypeptide chain. The nine fragment pairs were screened for selectable activity with the break-point disulfide alone, the fos-jun interaction alone, and with both together. The results are summarized in Table 5.

Addition of the break-point disulfide to the fos-jun interaction strongly increased the activity of seven of the nine fragment pairs, which makes eight out of ten pairs when α197/ω198 is included. The ten fragment pairs can be sorted into three groups. One group comprises the two negative pairs. The second group comprises three pairs which can only be activated by disulfide and fos-jun interaction together. In each case, the plating efficiency is at least 10% on 25 μg/ml ampicillin, with an activation index of at least 1000. The third group comprises five pairs, all from break-points in the C-terminal third of the molecule, which produce modest-to-robust activity with fos-jun alone, but potent activity with both fos-jun and the disulfide together. Most importantly, four of the five produce no selectable activity with the disulfide alone, so they have very large activation indexes. P174/N175 had the highest activation index, ~$10^7$ on 100 μg/ml ampicillin. G253/K254 had the highest activity with a plating efficiency of >25% on 400 μg/ml ampicillin. Interestingly, the first fragment pair identified to exhibit interaction-dependent activation, α197/ω198, remains the only pair to produce robust selectable activity with the break-point disulfide alone. It is possible that activation of some pairs is inhibited by the formation of mixed disulfides between the break-point cysteines and the internal cysteines, and it is also possible that such inhibition can be alleviated with exogenous reducing agent. However, it is at least as likely that in these cases unassisted refolding could not proceed far enough to allow efficient formation of the break-point disulfide before aborting.

The fact that the fragment pairs which produced the highest activities are not the same as those with the highest activation indexes and vice versa, indicates that different fragment pairs can be optimally suited for different applications. For example, the activation index is more important than maximum activity for intra-cellular interaction mapping, where natural interactions must be identified against backgrounds of $10^6$ or more non-interacting pairs. Thus, P174/N175 may be the best fragment pair for intra-cellular interaction mapping. On the other hand, maximum activity is more important than the activation index for in vitro applications because the activating target ligands will always be limiting in such applications. Since for maximum activation the fragments need only be used in ten-fold excess over their $K_d$s for the ligand, the activation index need only be 1000 for a signal-to-noise ratio of 100. Thus, G253/K254 may be the best fragment pair for in vitro applications such as biosensors or homogeneous assays.

The break-point disulfide overcomes a significant shortcoming of interaction-dependent enzyme fragment complementation systems. It is essential for high-throughput applications that such systems be capable of efficient activation by a wide range of heterologous protein-protein interactions. In other words, to minimize the false negative rate, the system must be activatable by any interaction between two proteins or fragments within the size range of single, naturally evolved protein domains, i.e., between ~100 and 300 amino acids in length. Globular proteins in this size range have radii in the range ~30-50 Å. This means that the points of attachment for the linkers could be up to 100 Å apart, and this distance must be spanned by the linkers in order for the break-points of the fragments to be able to come together. For this reason, the $(Gly_4Ser)_3$ (SEQ ID NO:4) linker was selected, which is expected to be fully extended and flexible, and to have a length of ~60 Å, thereby providing a combined length of up to 120 Å to allow close approach of the break-point termini during folding. Nevertheless, it is reasonable to expect the stability of the active conformation to be quite sensitive, and generally inversely proportional to the dimensions of the heterologous interaction. Thus, for all such systems described to date it can be assumed that the longer the linkers, the larger the proportion of possible interactions that can accommodate refolding, but the less the interaction can contribute to stabilization of the active conformation.

TABLE 5

Activation of TEM-1 β-lactamase Fragment Complementation by Disulfide-Assisted Fos-Jun Interaction [a]

| Break-point | +S-S, +Fos/Jun | | +S-S | | +Fos/Jun | | Background | |
|---|---|---|---|---|---|---|---|---|
| | Amp25 [b] | Hi Amp | Amp25 | Hi Amp | Amp25 | Hi Amp | Amp25 | Hi Amp |
| N52/S53 | + | 25 | − | − | − | − | − | − |
| E63/E64 | + | 25 | − | − | − | − | − | − |
| L91/G92 | − | − | − | − | − | − | − | − |
| Q99/N100 | + | 25 | − | − | − | − | − | − |
| H158/V159 | − | − | − | − | − | − | − | − |
| P174/N175 | ++++ | 200 | − | − | +++ | 50 | − | − |
| E197/L198 | ++++ | 100 | +++ | 50 | +++ | 50 | − | − |
| K215/V216 | ++++ | 100 | − | − | ++ | 25 | − | − |
| A227/G228 | ++++ | 200 | − | − | +++ | 50 | − | − |
| G253/K254 | ++++ | 400 | − | − | +++ | 50 | − | − |

[a] Fragment pairs were expressed in TG1 cells and plated onto ampicillin in the presence of 1 mM IPTG. Fragments were expressed with or without break-point terminal thiols (S-S) and with or without break-point terminal fos (ω) or jun (α) helixes.
[b] Activities are expressed as plating efficiencies (colonies per cell) on 25 μg/ml ampicillin (amp25). −, <$10^{-4}$; +/−, 0.01; +, 0.10; ++, 0.25; +++, 0.50; ++++, >0.90.
[c] HiAmp refers to the maximum ampicillin concentration in μg/ml on which fragment-expressing cells plate with >10% efficiency.

The break-point disulfide overcomes this limitation because, if the linkers are long enough, it will form readily during re-folding, and once the break-point disulfide is formed the specific activity of the reconstituted enzyme should be independent of the dimensions of the heterologous interaction, and in fact should not even require the continued integrity of the interaction. Thus, the break-point disulfide acts as a one-way switch, with an activation energy which can be supplied by a broad range of heterologous interactions, limited only by the ability of the interactors to fold properly, and by the length of the linkers to allow close approach of the break-point cysteines. This has two important consequences which allow a larger proportion of natural interactions to produce selectable activity. Longer linkers can be used, and interactions which are too weak to sustain selectable enzyme activity by themselves should still be able to "throw the disulfide switch" to produce selectable activity.

Example 6

Peptide-Enhanced Fragment Complementation

Another way to enhance interaction-dependent enzyme fragment complementation is to introduce short, random peptide sequences at the break-points, and then to select for increased activity with a model interaction. Such peptide-dependent enhancements can occur by any of several mechanisms. For example, the peptides can stabilize the active conformation of the reconstituted enzyme by interacting with each other or with the enzyme itself, or the peptides can stabilize one or both of the fragments, thereby increasing steady-state activity by increasing fragment concentration.

Synthetic oligonucleotides were used to add three randomized residues to each fragment between the break-point residue and the linker for the heterologous domain. As the model interaction, the c-fos helix at the N-terminus of ω198 and the c-jun helix at the C-terminus of α197 was used. For each randomized position, a degenerate codon was used, which encoded a subset of amino acids which was biased toward charged residues to favor charge-charge interactions, which are the strongest. The VRK codon places c, a, or g in the first position, a or g in the second position, and t or g in the third position. The encoded amino acids are His, Gln, Arg, Asn, Lys, Ser, Asp, Glu, and Gly. For three randomized positions in both fragments there are a total of $12^6=3\times10^6$ possible codon combinations, and $9^6=5.3\times10^5$ possible different amino acid sequences. Initially, ten thousand clones of the library were plated onto successively higher concentrations of ampicillin until no colonies were recovered. Six clones in the DH5α strain were recovered from 800 μg/ml ampicillin, and all six showed strict dependence on the fos-jun interaction for growth. In fact, the jun helix was removed from α197 in the same starting $10^4$ clones of the library, and when these clones were plated onto the same concentrations of to ampicillin, only a few colonies grew on 200 μg/ml ampicillin, and no colonies appeared on higher concentrations. This level of ampicillin resistance is comparable to that produced by the fos-jun interaction alone.

Unexpectedly, all six selected clones recovered from DH5α had the same α tri-peptide, Gly-Arg-Glu (GRE), and each had a different ω tri-peptide. When the ω tri-peptides were removed, there was no significant reduction in activity, suggesting that the ability of the GRE sequence to enhance fragment complementation did not depend on the presence of the ω tri-peptide. Thus, the GRE α tri-peptide produced a profound enhancement of the interaction-dependent activity, but it cannot substitute for the interaction. In fact, without the interaction the GRE tri-peptide does not seem to increase the background at all, thus it does not either accelerate refolding or stabilize the folded complex. The most likely effect of the GRE tri-peptide is to stabilize the α197 fragment by interfering with loss of the fragment by amorphous aggregation. Since the ω198 fragment is quite stable, but the α197 fragment is somewhat less so, the latter is expected to be limiting for fragment complementation, and any stabilization of α197 leading to an increase in its concentration increases the steady state activity of the interaction-activated enzyme accordingly. Though the GRE tri-peptide could inhibit aggregation of α197, it apparently did not interfere with re-folding of the fragment complex. Since aggregate formation proceeds exponentially, it is exquisitely sensitive to small shifts in the inter-molecular association rate constants (Dobson, *Trends Biochem Sci* (1999) 24:329). Thus, even weak binding of the tethered tri-peptide to the interacting surfaces can effectively defeat inter-molecular aggregation. As the complementary fragments fold cooperatively into the active complex, however, the weakly bound tri-peptide is readily stripped from its binding site by steric strain as the two become separated in the emerging native conformation. In this way the general ability of tethered small peptides to stabilize larger proteins without interfering with protein folding can be understood.

When the same random tri-peptide libraries were screened for fos/jun-mediated ampicillin resistance in the TG1 strain, five clones were recovered on 400 μg/ml ampicillin. With the fos-jun interaction alone TG1 cells will not plate above 50 μg/ml ampicillin. Thus, as before, tri-peptides were selected which substantially increased the level of ampicillin resistance produced by the fos-jun interaction alone. This time four different α tri-peptides were recovered, each with a different co tri-peptide.

| Pairs | α | ω |
|---|---|---|
| FHT400-1A1, -1B1 | HSE (cat agt gag) | REQ (cgg gag cag) |
| FHT400-2A1, -2B1 | NGR (aat ggg cgg) | QGN (cag ggt aat) |
| FHT400-4A1, -4B1 | GRE (ggt cgg gag) | DGR (gat ggg agg) |
| FHT400-9A1, -9B1 | EKR (gag aag cgt) | GRR (ggt agg agg) |
| FHT400-10A2, -10B1 | NGR (aat ggg cgg) | GNS (ggt aat agt) |

GRE was selected again from the α tri-peptide library. NGR was selected twice from the α tri-peptide library, with two different ωtri-peptides. In all cases, activation continued to be dependent on the fos-jun interaction. However, in contrast to the original GRE tri-peptide, activity was enhanced in all cases by the presence of the both the α and ω tri-peptides. Even the activity of the GRE tri-peptide was enhanced by the DGR tri-peptide on the ω fragment. Also, the fragments were interchangeable to some extent. Different α tri-peptides can be paired with different ω tri-peptides. The fact that enhanced activity was still fully dependent on the heterologous interaction suggests that the primary effect of the peptides was protection of the fragments to which they were attached from aggregation, rather than stabilization of the final fragment complex. The latter is expected to confer constitutive activity, independent of the heterologous interaction.

The GRE tri-peptide was also found to stabilize α197 in trans. When the α197-fos and jun-ω198 fusions were co-expressed in the *E. coli* periplasm with the GRE tri-peptide fused to the N-terminus of thioredoxin via a Gly$_4$Ser (SEQ ID NO:3) linker, the cells plated with 100% efficiency on 50 μg/ml ampicillin, whereas cells expressing the α197-fos and jun-ω198 fusions either alone, without the GRE-trxA fusion, or with a different tri-peptide-trxA fusion, plated with only ~1% efficiency on 50 μg/ml ampicillin. The GRE-trxA fusion conferred no resistance to ampicillin in the absence of the interacting helixes, thus it does not stabilize the re-folded fragment complex, but rather it must stabilize the α197 fragment since activity is limited by the amount of soluble α197. Since the GRE tri-peptide had the same stabilizing effect on α197 fragment when a different carrier was used, its activity must be context independent. Thus, an 18 kDa enzyme fragment can be stabilized at least 100-fold by a tri-peptide selected from a random sequence library. As with the tethered tri-peptide, the free GRE tri-peptide can inhibit aggregation of α197 without apparently interfering with re-folding of the fragment complex. In this case, however, displacement of the tri-peptide is greatly assisted by the fact that the effective intra-molecular concentrations of structural elements relative to one another are much higher than the tri-peptide concentration. In this way the general ability of small peptides to stabilize large proteins in trans without interfering with protein folding can be understood. This phenomenon is not widely appreciated, and in fact this may be the first demonstration that a functional protein can be deliberately stabilized by something as small as a tri-peptide.

Example 7

Mutationally-Enhanced Fragment Complementation

The ability of tri-peptides to stabilize β-lactamase fragments and thereby to increase both the interaction-dependent activity and activation index of the TEM-1 α197/ω198 complex should be of great benefit for in vitro applications of β-lactamase fragment complementation, where utility is most limited by fragment instability. Thus, it was of interest to determine if a comparable stabilization of the α197 fragment could be achieved by random mutagenesis and selection. To test this, the α197 coding sequence was mutagenized by error-prone PCR (Cadwell and Joyce, 1995, supra). The PCR conditions of Cadwell and Joyce mis-incorporate nucleotides in an unbiased fashion at a rate of one mutation every ~150 nucleotides. Since the α197 coding sequence is actually about 520 nucleotides in length, and ~75% of mutations change the encoded amino acids, less than three coding changes per molecule should be produced. About $10^8$ clones of the α197 mutant library were collected and co-expressed as the jun helix fusion with the fos helix fusion of wild-type ω198. The mutagenized α197jun fusion was expressed from the pAE1 vector and the fos-ω198 fusion was expressed from the pAO1 phagemid vector (see FIG. 6). When both constructs were co-expressed in strain DH5α colonies were recovered in the presence of 600 μg/ml ampicillin. Upon sequencing, two of three clones recovered (FI600-1 and -3) had the same sequence with two coding mutations, K55E (aag→gag) and M182T (atg→acg). The third clone (FI600-4) also had two coding mutations, one of which was shared with the other two (M182T), and the other of which, P62S (ccc→tcc), was proximal to the other mutation of the other clones.

Cells expressing either mutant consistently plated at >30% efficiency on 100 μg/ml ampicillin, whereas cells expressing the wild-type α197 plated at <$10^{-6}$ colonies per cell on 100 μg/ml ampicillin, and ~30% on 25 μg/ml ampicillin. However, for both mutants, plating efficiencies were just as high or higher in the absence of the heterologous interaction, i.e., with the jun helix removed. An exhaustive search for more mutations did not turn up any mutants with interaction-dependent activity. Thus, in contrast to the results obtained with random tri-peptides, where activation remained interaction-dependent, adaptive mutations of α197 invariably eliminated interaction dependence. This can be understood as follows. The tri-peptides stabilized the fragments by reversibly interfering with aggregation. Reversibility allows them to inhibit aggregation without interfering with folding. However, mutations are not reversible in this sense. If aggregation is caused primarily by the inter-molecular formation of native folding contacts, disruption of these by mutation might be expected to interfere with folding. In fact, it may be thermodynamically impossible to stabilize the fragments by mutation without inhibiting the re-folding process required to form the active fragment complex. This is because the native folds of the fragments have too much exposed hydrophobic surface to be stable. Thus, mutations can only stabilize the fragments by stabilizing alternative folds, which minimize exposed hydrophobic surface. However, these alternative folds must be unfolded before the native folding pathway can proceed to the active complex, and the energy required for this process can be prohibitive.

Since most aggregation is driven by aggregation-prone intermediates in the folding pathway, the rate of aggregation is proportional to the lifetimes of such species. The effects of the break-point disulfide described above indicated that the fragments are capable of association and initiation of folding in the absence of the heterologous interaction, but that the folding process is aborted when the fragments are not held together in some way, such as by the heterologous interaction or by the formation of a disulfide at the break-point. In the absence of either of these the probability that the fragments will dissociate before folding is complete is proportional to the folding rate, which in turn is proportional to the lifetimes of the folding intermediates. Thus, if the most likely mechanism for mutational inhibition of aggregation is to destabilize folding intermediates, this also accelerates folding and thereby reduces the probability that fragment dissociation occurs before folding were complete. In this way it can be understood why mutations which stabilize the folded complex are more likely to be selected than mutations which stabilize the fragments, and why the former, but not the latter give rise to constitutive, interaction-independent activity.

Example 8

Construction of a Human Peripheral Blood Lymphocyte Proteome Interaction Library.

The large number of functional interactions among both membrane-bound and secreted proteins of circulating immune cells include many which are yet to be discovered. For example, among the 150 or so CD antigens discovered so far, functions and ligands remain unknown for a substantial fraction (Ager et al., in *Immunology Today Immune Receptor Supplement*, 2$^{nd}$ Ed. (1997). In addition, the highly combinatorial mechanisms by which signalling specificity is generated imply that many signalling proteins participate in multiple functional interactions, and that even the best known of these proteins may have ligands and functions which remain to be discovered. Thus, the functional interactions of the extra-cellular proteome of the circulating cells of the immune system represent a potentially rich reservoir of pharmacological targets which are not readily accessible by currently available interaction mapping technologies. This proteome presents a unique opportunity to demonstrate the power of interaction-dependent β-lactamase fragment complementation systems for interaction mapping in that, while many important interactions remain to be discovered, many are already known by which the efficiency of the system can be gauged.

As discussed above, the activation index is the most important parameter of the interaction-dependent fragment complementation system for cleanly discriminating bona fide interactions from large pools of non-interacting protein pairs. Thus, for this application one uses the P174/N175 fragment pair of TEM-1 β-lactamase (α174 and ω175) because with the break-point disulfide this pair has the largest activation index, ~$10^7$. It also has a robust specific activity, but this can probably be improved even further with some fragment-stabilizing tri-peptides, so one can first insert the VRK or NNK tri-peptide library into the expression vectors between the break-point cysteines and the linkers (see FIG. 6), and select for growth on 300-800 μg/ml ampicillin. So long as the activation index is not compromised, higher specific activity conferred by fragment-stabilizing tri-peptides should allow weaker bona fide interactions in the expressed sequence libraries to confer selectable activity. In order to maximize the quality of the expressed sequence library, one might wish to subject the full-length cDNA library first to a normalization protocol to normalize the frequencies of rare and abundant sequences. From this normalized cDNA one then prepares random primed cDNA by PCR, and size-select fragments >200 base-pairs to enrich the library for sequences which encode fragments which are at least the size of single protein domains. Finally the library can be run through a fold-selection protocol to enrich for coding sequences which are expressed in the correct reading frame and in register with autonomously-folding protein domains (AFD).

Figure 9:
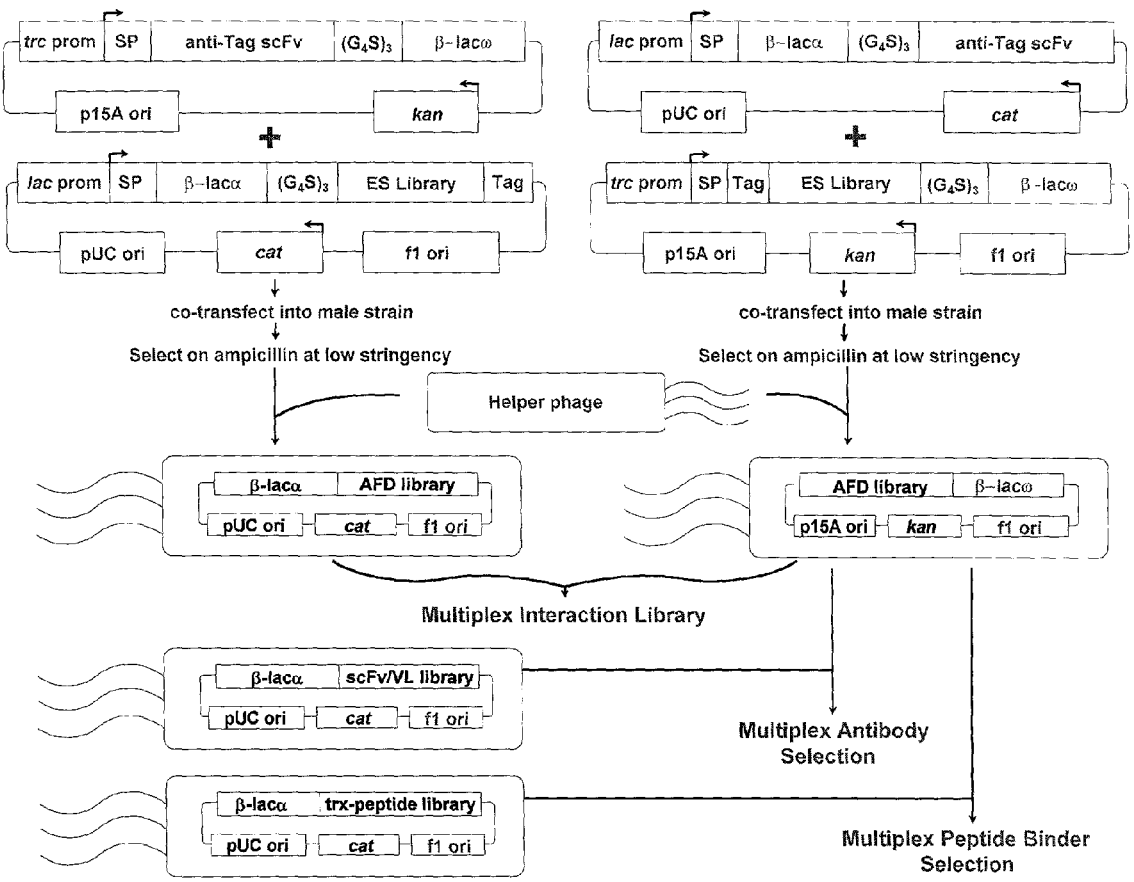
FIG. 9 shows vectors and protocol for construction of a multiplex protein-protein interaction library using interaction-dependent β-lactamase fragment complementation systems. Expressed sequence (ES), i.e., random-primed cDNA libraries, are subcloned into phagemid vectors for expression as fusions to the β-lactamase α and ω fragments, via the flexible linker (Gly$_4$Ser)$_3$ (SEQ ID NO:4). The vectors encode a peptide epitope tag, such as the 12-residue Myc tag, at the C-terminus of the ES. When co-expressed with anti-Tag scFv, such as anti-myc 9E10, fused to the other fragment, the ES libraries can be selected for β-lactamase activity driven by the Tag-anti-Tag interaction, which will require stable expression of the ES fragment. The resultant libraries, enriched for stable expressors of autonomously folding domains (AFD), can then be rescued as phage and co-infected into male cells for selection of interacting AFD pairs (Multiplex Interaction Library). The AFD libraries can also be co-infected with scFv libraries, antibody light chain variable region libraries (VL), or peptide libraries displayed on thioredoxin (trx-peptide) for simultaneous selection of binding proteins for each AFD (Multiplex Antibody/Peptide Binder Selection). See legends to FIGS. 6 and 10 for identification of other abbreviations.

Rough microsomes, which are derived from membranes of rough ER and are therefore enriched in mRNA for secreted and membrane proteins, can be isolated from unfractionated lymphocytes from pooled human blood by sedimentation velocity in sucrose density gradients (Gaetani et al., *Methods in Enzymology* (1983) 96:3; Natzle et al., *J Biol Chem* (1986) 261:5575; Kopczynski et al., *Proc Natl Acad Sci* (1998) 95:9973). Messenger RNA can then be purified from the rough microsomes using a commercially available kit (e.g., Poly(A) Select, Promega, Inc., Madison, Wis.). A randomly-primed cDNA library is then made from the RNA template and cloned directionally. First-strand cDNA is made with AMV reverse transcriptase (RT) and random hexamer primers (Sambrook et al., 1989, pp. 8.11-8.21). The primers contain a unique 5' extension with convenient restriction sites for ligation into the β-lactamase α and ω fusion expression vectors. The template is destroyed by the RNAseH activity of AMV RT and the unused primers are removed using a spun column. The second strand is then made with the Klenow fragment of DNA polymerase I and random hexamer primers containing a different unique 5' extension with a different restriction site for insertion into the expression vectors. After removal of unused primers, the cDNA is PCR-amplified with primers corresponding to only the unique sequence on each original primer (Dieffenbach and Dveksler, in *PCR Primer: A Laboratory Manual*, Cold Spring Harbor Press, cold Spring Harbor, N.Y., 1995), so that the majority of amplified fragments have the correct orientation for expression in *E. coli*. The product is then normalized by exhaustive hybridization to a limiting amount of human genomic DNA immobilized on magnetic beads (Kopczynski et al., 998, supra). Since coding sequences are naturally normalized in genomic DNA, cDNA recovered from the genomic DNA hybrids should be normalized. After a final amplification, the PCR product is size selected by centrifugal gel filtration on Sephacryl S-400 spun columns for fragments >~200 bp. The cDNA is then digested with appropriate restriction enzymes and ligated into the interaction-dependent β-lactamase α174 and ω175 fusion expression vectors, which are essentially the same as those shown in FIG. 6, except for some modifications required for fold selection. The vectors and protocol for fold selection and interaction mapping of the cDNA library are illustrated in FIG. 9.

For convenient fold selection, both vectors for expression of the library as α and ω fusions are compatible phagemids. In addition, a peptide epitope tag, such as the well-known 12-mer derived from the c-myc oncogene (Hoogenboom et al., 1998, supra) is encoded at the C-terminus of the cDNA, or expressed sequence (ES) library in the α-fusion vector, and at the N-terminus of the ES library in the ω-fusion vector. When co-expressed with an anti-tag scFv, such as the anti-myc 9E10 scFv (Hoogenboom et al., 1998, supra) fused to the other β-lactamase fragment, each fusion library can be enriched for clones which express autonomously folding domains (AFD) in the correct reading frame. The principle of the selection is that only fragments which can fold into their native conformations will be stable enough to support selectable levels of β-lactamase fragment complementation driven by the tag-anti-tag interaction.

The normalized cDNA library-vector ligation products are transduced into $E.\ coli$ strain TG-1 by high-voltage electroporation (Dower et al., Nucleic Acids Res (1988) 16:6127), and plated onto the minimum ampicillin concentration on which non-interactors are known to plate with efficiencies of $\leq 10^{-3}$ since at least a 100-fold excess of non-AFD-encoding fragments is expected in the libraries. For the α174/ω175 system, the recommended ampicillin concentration is ~25 μg/ml. Since there is not likely to be more than $10^4$ secreted or membrane protein genes expressed in PBLs, and the frequencies of expressible AFDs can be in the range of $10^{-2}$ per gene, one should collect at least $10^7$ clones of each library to insure representation of all expressible extra-cellular AFDs.

Once the normalized ES libraries have been enriched for AFD-encoding clones, the libraries can be rescued as filamentous phage by high-multiplicity super-infection of at least $10^8$ cells of each library with the helper phage M13K07 (Sambrook et al., 1989, pp. 4.17-4.19). After overnight growth in suspension the library phage are recovered from the culture supernatant by precipitation with polyethylene glycol, and reconstituted in phosphate-buffered saline. The library phage stocks can be stored frozen in 15% glycerol. Fresh $E.\ coli$ TG-1 cells can then be co-infected with a high-multiplicity of each phage library and plated onto a concentration of ampicillin on which the activation index of the system is known to be maximal. For the α174/ω175 system, 100 μg/ml ampicillin is optimal, since the activation index is at least $10^7$ and the fos-jun interaction-mediated plating efficiency is at least 50%. At least $10^{14}$ transforming units of each fusion library phage should be used to infect at least $10^{12}$ log phase TG-1 cells to insure that most of the possible pair-wise combinations of $10^6$ clones of each AFD library are present in the doubly infected cell population before selection. After a one-hour adsorption at $10^9$ cells per ml, the cells are washed, resuspended in fresh medium, and incubated for another hour with gentle shaking to allow the phagemid genes to express. The cells are then concentrated and plated on 100 large petri dishes (150 mm dia.) containing solid LB medium containing 1 mM IPTG and 100 μg/ml ampicillin. A small aliquot is plated on chloramphenicol and kanamycin to determine the number of co-transformants.

Since ~$10^{10}$ cells are being seeded onto each plate, it is possible that the interaction frequency might be high enough for the plates to overgrow. This takes at least $10^4$ clones per plate. In this case, all of the selected clones have to be recovered by scraping and replated at lower densities. If a large number of clones is recovered, at least 100 are replated anyway to determine the background frequency due to ampicillin escapes. From those that breed true, each candidate interactor are recovered and tested for interaction with an unselected partner. Selected pairs are sequenced and BLAST-searched for homology to known genes (Altschul et al., J Mol Biol (1990) 215:403; Altschul et al., Nucleic Acids Res (1997) 25:3389). A large number of interactions among secreted and membrane proteins of immune cells are already known, such as the B-cell co-activation antigen, CD40 and its T-cell ligand, CD40L, and the T-cell activation antigens B7.1 and B7.2 and their ligands CD28 and CTLA4. Labeled oligo-nucleotide hybridization probes are prepared for these known interactions, and colony lifts of the entire interaction library are probed to see what fraction of expected interactors are actually represented in the library. Interaction partner sequences from positive clones are recovered, and homology searched to determine if known or new interactors have been identified. Colonies expressing bona fide interactions are grown up and stored indefinitely in 15% glycerol at −70° C., pending further characterization or use for e.g., drug screening.

Example 9

Construction of An Intra-Cellular Signal Transduction Biosensor

Interaction-dependent β-lactamase fragment complementation systems can be adapted for activation or inactivation by virtually any post-translational modification that occurs naturally in cells. As a result they can be deployed intra-cellularly as biosensors to monitor the activity of any process which is regulated by post-translational modification. A major class of such processes is phosphorylation-regulated signal transduction pathways. Phosphorylation-regulated intermediates are obligatory components of most processes by which cells respond to extra-cellular conditions or messenger molecules by altering gene expression. Cellular responses to extra-cellular signals fall into three general categories: growth, survival, and differentiation. A ubiquitous component of neo-plastic transformation is the deregulation of growth control signaling, often accompanied by the deregulation of survival signalling as well. This often occurs by over-expression of phosphorylation-regulated signal transducers, or by mutational disabling of phosphorylation-mediated regulation. Thus, most so-called oncogenes are phosphorylation-regulated growth signal transducers, which become over-expressed or mutated to constitutive activity in cancer cells.

The Her-2/neu oncogene is a 185 kDa Type I transmembrane receptor tyrosine kinase, which is a member of the epidermal growth factor receptor (EGFR) family. This growth factor receptor is over-expressed in particularly aggressive adenocarcinomas of epithelial origin in a number of tissues, notably breast. When normally expressed, Her-2/neu hetero-dimerizes with other EGF-family receptors when they are ligated by growth factor. This leads to cross phosphorylation of multiple tyrosines on the cytoplasmic domains of the receptors. Phosphorylation of tyrosine 1068 (Tyr1068) on Her-2/neu leads via phospho-tyrosine-binding accessory proteins and guanosine nucleotide exchange factors to activation of $p21^{ras}$, and thence to activation of cell division via the MAP kinase cascade. When Her-2/neu is sufficiently over-expressed, the background level of ligand-independent EGFR hetero-dimerization rises to a level which is in turn sufficient to maintain constitutive mitogenic signaling even in the absence of growth factor, leading to the characteristically uncontrolled growth of tumor cells. Thus, there is much interest in finding drugs which can block the activation of Her-2/neu, particularly in a manner which can prevent constitutive signaling in tumor cells without blocking EGF signalling in normal cells.

A cell-based biosensor, which produces a readily detectable and quantifiable signal when Her-2/neu activation is blocked, is particularly useful for high-throughput screening of chemical libraries for compounds with anti-breast tumor potential. Such a biosensor can be set up with a β-lactamase fragment complementation system as follows. The ω fragment is fused via flexible linker to the C-terminus of Her-2/neu, which is proximal to the Tyr1068 substrate of the receptor kinase. The α fragment then is fused to a binding protein, such as a scFv or VL, which binds to the Tyr1068 region of the receptor only when Tyr1068 is unphosphorylated. Since Tyr1068 is mostly phosphorylated in Her-2/neu over-expressing cells, especially in the presence of EGF, β-lactamase activation is minimal. However, in the presence of an inhibitor of Her-2/neu activation, the proportion of unphosphorylated Tyr1068 rises, recruiting the α-Tyr1068 binder fusion to the receptor where α-ω complementation increases β-lactamase activity in the cells. In the presence of a fluorogenic β-lactamase substrate, inhibitors of Her-2/neu activation are readily identified by increasing fluorescence in a matter of minutes, since dephosphorylation of Tyr1068 occurs rapidly upon inhibition of the Her-2/neu kinase activity.

For intra-cellular biosensors both maximum activity and the activation index is important. However, for all five of the best TEM-1 fragment pairs the activation index is expected to depend almost entirely on the difference in the affinity of the binder for Tyr vs phospho-Tyr. Thus, the fragment pair with the highest activity, i.e., G253/K254 (α253 and ω254), is preferred, especially since for intra-cellular applications the break-point disulfide cannot be used. It is possible to increase the intra-cellular activity of α253/ω254, if desired, by selecting one or two fragment stabilizing tri-peptides, as described above.

The first step in developing the Her-2/neu inactivation biosensor is to obtain a Tyr1068-binding protein. This is accomplished by inserting the coding sequence for the substrate peptide, PVPEYINQS (SEQ ID NO:25), into the active site of thioredoxin, between G33 and P34, flanked by short flexible linkers such as PGSGG (SEQ ID NO:26) to minimize structural constraints on the peptide, which does not require a rigid structure for binding to its natural ligand, the Grb2 SH2 domain. This Tyr1068 trxpep then is fused via a $(Gly_4Ser)_3$ (SEQ ID NO:4) linker to the N-terminus of ω254, and co-expressed in *E. coli* TG-1 cells with a scFv library of at least $10^8$ clones, or a VL library of at least $10^6$ clones fused to the C-terminus of α253 via the $(Gly_4Ser)_3$ (SEQ ID NO:4) linker. Since the Tyr1068-binder is being selected for deployment in the mammalian cell cytoplasm, it might be prudent to perform the selections in the *E. coli* cytoplasm. For this purpose the vectors in FIG. 6 can be used with the signal peptides removed. Then a chromogenic substrate such as nitrocefin (λmax=485 nm; ξ=17,420 $M^{-1}$ $cm^{-1}$; McManus-Munoz and Crowder, *Biochemistry* (1999) 38:1547) is used to select Tyr1068-binders by color. By plating at least $10^6$-$10^8$ transformants at moderate to high stringency, i.e., on decreasing concentrations of the substrate, it should be possible to identify binders with sub-micromolar affinities since Tyr is the most common amino acid in high-affinity protein-protein interfaces. Such affinities will be desirable for maximum discrimination between Tyr and phospho-Tyr. Selected Tyr1068-binders must be tested for inhibition by phosphorylation of the Tyr. This can easily be accomplished by expressing the vectors in isogenic cells which over-express a broad spectrum Tyrosine kinase (TKX1 cells, Stratagene, Inc., La Jolla, Calif.).

Once a suitable phosphate-sensitive Tyr1068-binder has been identified, the entire coding sequence for the α253-Tyr1068-binder fusion is subcloned into a mammalian expression vector, such as the pCMV-Tag vectors (TKX1 cells, Stratagene, Inc., La Jolla, Calif.) for expression in mammalian cells from the cytomegalovirus promoter. The ω254 fragment is expressed as a fusion to the C-terminus of the Her-2/neu cytoplasmic domain, which contains Tyr1068. The coding sequence of the 1210-residue EGF receptor (Genbank accession no. X00588; Ullrich et al., *Nature* (1984) 309:418) can be used as it is operationally identical to Her-2/neu, and its Tyr1068 will become phosphorylated under the same conditions of over-expression and/or growth factor ligation in tumor cells. When fused to the C-terminus of EGFR via the $(Gly_4Ser)_3$ (SEQ ID NO:4) linker, the 35-residue ω254 β-lactamase fragments will be only 152 residues away from Tyr1068. Both the EGFR-ω254 fusion and the α253-Tyr1068-binder fusion are expressed from the same vector from a dicistronic mRNA. This is accomplished by inserting an internal ribosome entry site (IRES; Martinez-Salas, *Curr Opin Biotechnol* (1999) 10:458) between the termination codon of the upstream cistron and the initiation codon of the downstream cistron. This allows both proteins to be made simultaneously from the same mRNA. The vector is introduced into the tumor cell line by cationic liposome-mediated transfection, using e.g., lipofectamine (Gibco-BRL, Gaithersburg, Md.) according to the protocol in the product literature. Operation of the biosensor is tested in transiently transfected cells, and if operational, stable transformants are then isolated by selection for long term antibiotic resistance. Multiple free-diffusible chromogenic and fluorogenic substrates are available for continuous monitoring of β-lactamase activity. Operationally, the ω254 fragment is anchored to the plasma membrane at the C-terminus of the cytoplasmic domain of the receptor near Tyr1068, and the α253 fragment is free in the cytoplasm as the Tyr1068-binder fusion. ATP-analog tyrosine kinase inhibitors are available commercially and can be used as positive controls for inhibitor selection, and to determine the signal increment from fully-activated to fully-inhibited EGFR.

Example 10

Target-Activated Enzyme Prodrug Therapy.

Antibody-directed enzyme prodrug therapy (ADEPT) is a promising anti-cancer chemotherapeutic strategy which takes advantage of the catalytic power of enzymes to amplify the cytotoxicity-targeting power of tumor-specific antibodies. Enzymes are concentrated at the tumor site when administered as conjugates of tumor-specific antibodies. After unbound conjugate has cleared from the circulation, prodrugs can be administered which are relatively non-toxic until activated by the tumor-bound enzyme, whereupon the cytotoxic product can accumulate at the tumor site to concentrations which are unattainable by parenteral administration of the drug without excessive toxicity. Enzymes such as β-lactamase have been chemically or genetically conjugated to tumor-targeting antibodies and used with β-lactam derivatives of anti-tumor drugs such as cephalosporin mustards and anthracyclines to achieve promising anti-tumor effects in animals. The efficacy of ADEPT is limited, however, by the need for unbound conjugate to clear the circulation before the prodrug can be administered. By the time the circulating conjugate is depleted to the threshold below which systemic activation of the prodrug produces acceptable levels of toxicity, so much of the conjugate has been lost from the tumor that efficacy is often seriously compromised.

This problem can be overcome by using an interaction-dependent β-lactamase fragment complementation system with tumor targeting antibodies. When fused to single-chain antibody fragments (scFv) which recognize non-overlapping epitopes on tumor markers, the β-lactamase fragments can localize to the tumor and reconstitute sufficient β-lactamase activity on the tumor cell surface to produce high levels of tumor-localized cytotoxicity from β-lactam prodrugs. The great advantage of such a system is that prodrug activation cannot occur in the general circulation or anywhere the tumor marker is not encountered, so that the prodrug can be administered either simultaneously with high doses of the scFv-fragment fusions, or at the point of highest tumor load of the fragments, without regard for the circulating levels of the fragments which are completely inactive.

As an example, the construction and purification of fusions of interaction-dependent β-lactamase fragments with scFv which bind non-overlapping epitopes on the human breast tumor marker Her-2/neu is described. One can then determine the kinetics of reconstitution of β-lactamase activity on the surface of Her-2/neu—expressing SKOV3 human ovarian cancer cells. Under conditions of optimum loading, killing of the cells can then be assessed for different cephalosporin prodrugs as a function of concentrations known to be limiting in vivo. The resulting Tumor-Activated Enzyme Prodrug Therapy (TAcEPT) system can then be tested for its ability to ablate SKOV3 and other Her-2/neu-expressing human tumors in severe combined immuno-deficient (scid) mice. Once the efficacy and safety of the system has been demonstrated in animal models, toxicity and efficacy trials can be initiated in human breast cancer subjects.

The requirements for therapeutic use of β-lactamase fragment complementation systems are similar to those for in vitro use in general. The most important parameters are specific activity and fragment stability, while activation indexes above 1000 confer little additional efficacy. Thus, the α253/ω254 is the recommended fragment pair for this application because it has the highest interaction-dependent specific activity, the fragments are moderately stable, and its activation index is more than adequate. However, the stability of the α253 fragment can probably be improved by a custom fragment-stabilizing tri-peptide. Thus, before setting up the tumor-activated system, one might first subclone a degenerate sequence encoding the VRK or NNK tri-peptide library into the α253 expression construct between the break-point cysteine and the linker (see pAE1 in FIG. 6). α253-stabilizing tri-peptides are then selected by plating at least $10^4$ library transformants on increasing ampicillin from 400 to 1000 µg/ml, since α253/ω254 plates quantitatively on 400 µg/ml even without a stabilizing peptide, and wild-type TEM-1 β-lactamase does not plate on more than 1000 µg/ml when expressed under these conditions.

10a. Expression of TEM-1 β-lactamase H25-G253 (α253) and K254-W288 ((ω254) Fragments as Fusions to scFv Against Non-overlapping Epitopes on the Her-2/neu Human Breast Tumor Marker.

Figure 10:
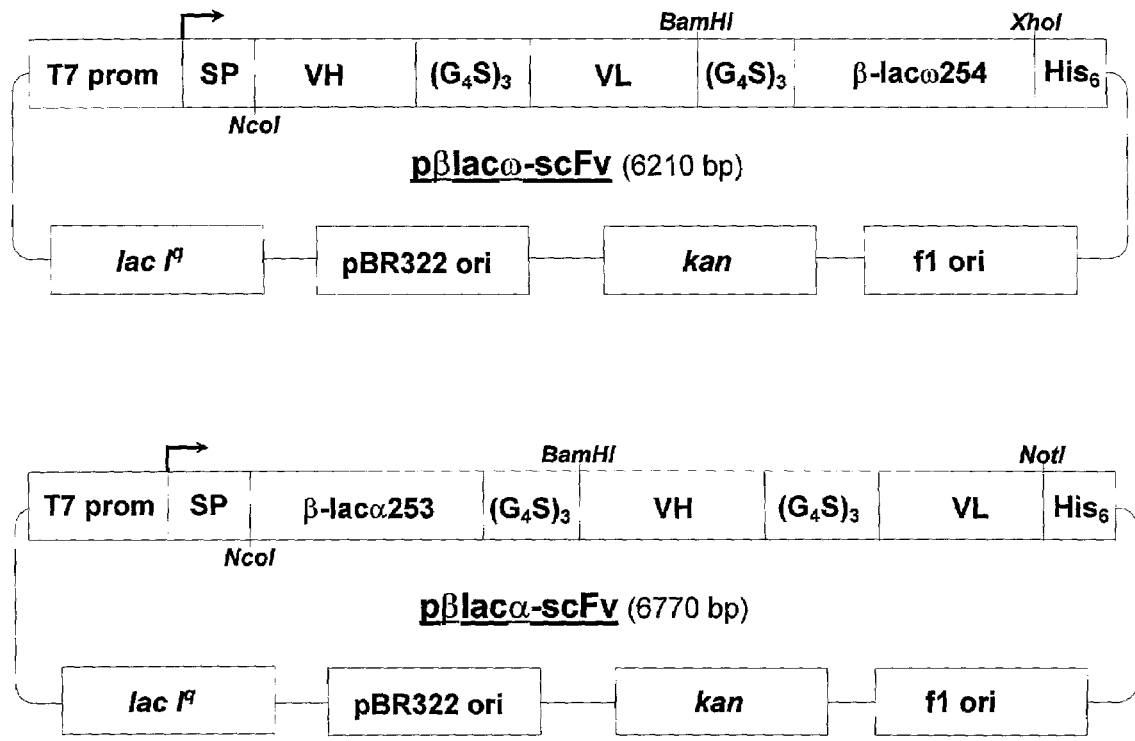
FIG. 10 shows expression vectors for production of β-lacα253 and β-lacω254 fusion proteins with scFv. Arrows denote translation start sites. T7 prom, bacteriophage T7 promoter; SP, pelB signal peptide; scFv is comprised of VH (antibody heavy chain variable region), (Gly$_4$Ser)$_3$ (SEQ ID NO:4) (15-mer flexible linker), and VL (antibody light chain variable region); kan, kanamycin resistance; His$_6$ (SEQ ID NO:5), hexa-histidine tag for metal ion affinity purification; lacI$^q$, high-affinity lac operon repressor mutant; f1 ori, phage origin of replication.

The tumor activation mechanism for these fragments can employ two scFvs such as those described by Schier et al. (*Gene* (1996) 169: 147), which were derived from a phage display library of a human non-immune repertoire (Marks et al., 1991) by panning against a recombinant fragment comprising the extra-cellular domain (ED) of Her-2/neu. These two scFv appear to recognize non-overlapping epitopes, since they do not compete for binding to the Her-2/neuED by ELISA. The affinity of one of these scFv was improved to sub-nM Kd in vitro (Schier et al., 1996, supra), and similar improvements in the other can be made using the same methods (Balint and Larrick, *Gene* (1993) 137:109). The coding sequences for the scFv can be subcloned into the β-lactamase α and ωfusion production vectors, pβlacα: and pβlacω, shown in FIG. 10. These vectors are derived from pET26b (Novagen), and have convenient restriction sites for insertion of both scFv and β-lactamase fragment sequences. Each fusion protein is inducibly expressed (IPTG) from the strong phage T7 promoter under the control of the lac repressor. Each primary translation product contains a pelB signal peptide for secretion into the bacterial periplasm and a C-terminal $His_6$ (SEQ ID NO:5)tag for one-step purification from osmotic shock extracts by immobilized metal ion affinity chromatography (IMAC, Janknecht et al., *Proc Natl Acad Sci* (1991) 88:8972). The yield of each fusion protein can be optimized primarily by manipulation of the inducer concentration and the growth temperature.

Each scFv can be expressed as both α and ω fusions to determine which arrangement(s) (1) support the highest binding activity, (2) support the highest enzymatic activity, and (3) support the highest yields. Initially, expression can be optimized by the criterion of silver-stained PAGE. Then fusion proteins should be purified from osmotic shock extracts (Neu and Heppel, 1965, supra) by IMAC. The purified fusion proteins can be tested for binding to an immobilized recombinant fusion of the Her-2/neu extra-cellular domain (ED) to a stabilizing immunoglobulin domain (Ig) by ELISA using an anti-$His_6$ (SEQ ID NO:5)tag antibody (Qiagen). The purified fusion proteins can then be tested for reconstitution of β-lactamase activity on immobilized rc- Her-2/neu ED-Ig using a chromogenic substrate, nitrocefin (λmax=485 nm; ε=17,420 $M^{-1}$ $cm^{-1}$; McManus-Munoz and Crowder, 1999, supra). Immobilized BSA can be used as the negative control.

10b. Determination of the Kinetics of Specific β-lactamase Activation by Binding of β-lacα/ω-scFv Fusions to Immobilized Recombinant Antigen.

One can determine β-lactamase activity quantitatively as a function of binding of the fusion proteins to the immobilized antigen. This rate can then be compared to that obtainable with intact β-lactamase fused to the same scFv as an indication of how much activity can be localized on a tumor compared to an established vehicle, for example, an antibody-β-lactamase conjugate.

First, conditions are established for saturating the antigen with one of the scFv-β-lac fragment fusion proteins. The wells of microtiter plates are coated with antigen, and exposed to increasing amounts of the first scFv-fragment fusion until the ELISA signal plateaus. At this level, i.e., saturating amounts of the first fusion protein, increasing amounts of the second fusion is added. After binding and washing, β-lactamase activity is determined spectrophotometrically after a 30' incubation with excess nitrocefin. If the assay is performed in triplicate, $V_{max}$ should be a more or less linear function of the concentration of the second fusion. As the amount of second fusion is increased, at some point $V_{max}$ should plateau. The amount of the second fusion bound can be determined by ELISA, and a relative specific activity ($k_{cat}^{rel}$) can be computed for the fragment-reconstituted β-lactamase. The $K_M$ can be estimated in solution with saturating antigen and saturating first fusion and limiting amounts of the second fusion. A range of nitrocefin concentrations is added and the initial rates of change of absorbance at 485 nm is measured as a function of second fusion concentration. The $K_M$ is then computed from standard regression analysis.

To compare with intact β-lactamase, a fusion of intact β-lactamase to the second scFv is prepared. This is then added in increasing amounts to antigen-coated wells which have been saturated with the first fusion as had been done before. Again, $V_{max}$ should be a more or less a linear function of the amount of intact β-lactamase fusion and should plateau at saturation. At each point, the amount of intact β-lactamase fusion bound, as determined by ELISA, should be comparable to the amount of the second fragment fusion bound, and the ratio of $V_{max}$ should reflect the ratio of specific activities of the intact and fragment-reconstituted β-lactamases. For comparison, the $K_M$ is estimated as described above for the fragment-reconstituted enzyme. The TEM-1 α253/ω254 fragment complex is expected to have a maximum activity ($k_{cat}$) near that of the intact enzyme. If the $K_M$ are also comparable, activities on a tumor up to 100-fold higher at the peak of prodrug activation than with the conventional antibody-β-lactamase fusion might be expected, which can have 1% or less of its peak activity left when the unbound fusion has cleared the circulation enough to allow prodrug administration.

10c. Determination of Killing Kinetics of Her-2/Neu-Expressing SKOV3 Ovarian Carcinoma Cells by scFv-mediated β-lacα/ω Activation of Cephalosporin Prodrugs.

The arrangement(s) of scFv-β-lactamase fragment coupling which produce(s) the highest specific β-lactamase activities on immobilized antigen then are tested for activation of β-lactamase activity in the presence of human tumor cells expressing the Her-2/neu antigen. Cell killing can be assayed using any of the three cephalosporin prodrugs shown in FIG. 5. The fragment-reconstituted activity again is compared with the intact β-lactamase activity, this time with respect to tumor cell killing. Such results should indicate the dose range which can be required to show a significant anti-tumor effect in animals, which will be the next step in preclinical evaluation of the tumor-targeted β-lactamase.

The SK-OV-3 line of human ovarian adenocarcinoma cells (ATCC) are seeded in 6-well tissue culture plates at $3 \times 10^5$ cells per well in Dulbecco's Minimum Essential Medium (DMEM) supplemented with 10% fetal calf serum (FCS), and allowed to grow to confluency at 37° C. in 10% $CO_2$. The saturability of both Her-2/neu epitopes on the cells is determined with increasing amounts of intact β-lactamase fused to each scFv, as determined spectrophotometrically after nitrocefin hydrolysis. The $V_{max}$ of the fragment-reconstituted enzyme can then be determined on the cells with saturating concentrations of both fusions and nitrocefin. It is expected to conform to the predicted activity based on the maximum intact β-lactamase activity and the ratio of $V_{max}$ observed on the immobilized recombinant antigen. The sensitivity of the cells to any of the three prodrugs shown in FIG. 5 can be determined essentially as described by Marais et al. (*Cancer Research* (1996) 56:4735) with and without the intact β-lactamase-scFv fusions and the α/ω fragment-scFv fusions under saturating conditions. The prodrugs are dissolved in DMSO and diluted into DMEM/FCS to a range of concentrations immediately prior to use. One ml is added to each well and the cells are incubated overnight. The cells are then washed, trypsinized, and viability is determined by dye exclusion. Aliquots are then seeded into fresh dishes. After four days of growth, cell viability is assessed by incorporation of [$^3$H] thymidine as determined by liquid scintillation counting of acid insoluble material. The results are expressed as percentage of untreated control cells. Again, the relative cytotoxicities of the prodrugs with the β-lactamase fragment system are compared to those of the intact β-lactamase fusions, particularly those at the lower prodrug concentrations where second order rate constants ($k_{cat}K_M$) can be important, to give an indication of the potential increase in efficacy of TAcEPT over conventional ADEPT in vivo.

Example 11

Ligand-Dependent Activation of Circular Permutations of β-Lactamase

The utility of the β-lactamase interaction-dependent fragment complementation system for in vitro applications such as homogeneous assays or in vivo applications such as target-activated prodrug activation can be hampered by the requirement for tri-molecular activation kinetics. Kinetics can be substantially improved if the reaction order can be reduced, for example, from bimolecular to unimolecular or from tri-molecular to bimolecular. One approach is to develop a circular permutation (CP) of β-lactamase which can be activated only by ligand-mediated interaction of heterologous domains fused to the break-point termini of the CP. The present invention demonstrates the development of such interaction-dependent CPs.

In principle, any enzyme can be circularly permuted by inserting a flexible, hydrophilic linker between the C- and N-termini, whose length is roughly commensurate with the half-circumference subtended by the straight-line distance between the two termini in the native conformation. For example, a globular protein of 50 kDa can have a linear distance between termini of no more than ~50 Å. This requires a linker of 25/7π or ~80 Å, which is equivalent to ~20 residues of extended sequence. New N- and C-termini can then be introduced at any other point in the polypeptide chain. For most enzymes in which the native termini occupy proximal positions in the native conformation, and particularly if they reside in directly interacting elements of structure such as a β-sheet or coiled coil, it has been possible to find circular permutations of the sequence which retain substantial activity and stability. Functional circular permutations have been described for green fluorescent protein (Baird, et al, *Proc Natl Acad Sci* (1999) 96:11241 and Topell, et al, *FEBS* Lett (1999) 457:283), disulfide oxidoreductase (Hennecke et al., *J Mol Biol* (1999) 286:1197), dihydrofolate reductase (Iwakura, *Biosci Biotechnol Biochem* (1998) 63:778), beta-glucosidase (Garcia-Vallve et al., *Proteins* (1998 31:214), beta-glucanase (Ay et al, *Proteins* (1997) 30:155), aspartate transcarbamoylase (Graf and Schachman, *Proc Natl Acad Sci* (1996) 93:11591), dihydrofolate reductase (Uversky et al., *Protein Sci* (1996) 5:1844), and phosphoglycerate kinase (Ritco-Vonsovici et al. *Biochemistry* (1995) 34:16543). In fact, active circular permutations occur naturally and may be common (Lindqvist and Schneider, *Curr Opin Struct Biol* (1997) 7:422; Jia et al., *Structure* (1996) 4:715). Two general criteria must be met for a permutation to have constitutive activity. These two criteria relate to the extent to which the stability of the native conformation and the native folding pathway are perturbed by the permutation. The former is minimized when the polypeptide chain is broken in regions where it makes relatively little contribution to the stability of the native fold, so that breaking the chain does not lead to spontaneous cooperative unfolding of the enzyme.

The effects of permutation on folding pathways are more complex. Proteins are generally hierarchical in structure. As a result, folding is generally believed to proceed hierarchically (Baldwin and Rose, *Trends Biochem* (1999) 24:26 and 24:77). That is, folding pathways are believed to initiate with local interactions at one or more points along the chain. As elements of secondary structure accumulate, local interactions among these lead to the progressive formation of higher order structures through increasingly distal interactions until the native conformation is achieved. By this scenario, permutation may perturb the folding pathway in two ways: (1) by favoring the early association of structures which normally interact late, such as the native termini, and (2) by retarding the interaction of local structures which may normally associate early, such as those proximal to the break point. The premature formation of one or more tertiary associations may be favored in permutations, and such associations can sterically inhibit the rearrangement of non-native associations subtended by them. This can cause fatal delays in folding. Such folding perturbations, rather than a loss of stability, can be the most common reason that most circular permutations fail to fold rapidly enough to avoid aggregation or proteolysis.

However, it is reasonable to expect that most proteins will have one or more exposed loops whose integrity is essential for stability. This is supported by observations that cleavage of protease recognition sites inserted into exposed loops of β-galactosidase (Baum et al., *Proc Natl Acad Sci* (1990) 87:10023) or the tetracycline resistance protein (Block and Grafstrom, *Antimicrobial Agents and Chemotherapy* (1990) 34:2337) in many cases lead to inactivation of the enzymes. Thus, circular permutation of the polypeptide chain within such loops should produce unstable proteins. This is the first of three requirements for an interaction-dependent CP. The second requirement is that the CP must not be sterically blocked from reaching the active conformation. The third requirement is that in the equilibrium ensemble of inactive conformations of the CP the break-point termini are separated by an average distance which exceeds that allowed by interactions of heterologous domains fused to the break-point termini. Even if the active conformation is only a minor component of the ensemble, this can be enough to allow a stable complex of the interactors to form upon transient approach of the break-point termini. Once the interaction complex has formed, the CP can become "trapped" in a more active conformation. That is, a substantial proportion of the equilibrium ensemble becomes sterically excluded, and the equilibrium is shifted toward the active conformation. Structural effects on enzymatic activity tend to be highly non-linear, such that even a modest increase in the active conformation can increase enzymatic activity by several orders of magnitude.

Thus, in principle, useful interaction-dependent circular permutations should be possible if foldable, but unstable CPs can be found in which the average separation of the break-point termini is large. The proposed mechanism by which such CPs are activated is roughly the opposite of that by which interaction-dependent fragment complementation is believed to occur. In the latter, the heterologous interaction docks the fragments long enough to allow them to refold into the active conformation. However, in the case of the CP, it is transient folding of the CP which allows the interactors to make contact, and the latter then traps the CP in an active conformation. To identify such CPs of TEM-1 β-lactamase, we inserted a sequence encoding the flexible $(Gly_4Ser)_3$ (SEQ ID NO:4) linker between the C- and N-termini of two tandem copies of the TEM-1 sequence. CPs of the TEM-1 sequence were then amplified by PCR using primers which terminated within each of ten different exposed loops in the structure of the enzyme (see FIG. 3). Rather than use a model interaction which can bias the screen, we chose to screen first for activation by the formation of a disulfide bond at the break-point. Oxidation of proximal thiols to disulfides is extremely rapid and promiscuous in the bacterial periplasm (Rietsch and Beckwith, *Ann Rev Genet* (1998) 32:163). Thus, we reasoned that any CPs which were foldable but unstable should allow the transient approach of cysteines placed at the break-point termini long enough for the disulfide to form. The results of this screen are summarized in Table 6.

The TEM-1 CPs were expressed with and without break-point cysteines from the pAO1 vector (see FIG. 11) in the TG1 strain of *E. coli* with 5 mM IPTG for induction of transcription from the lac promoter. Each CP was plated on 25 μg/ml ampicillin at $10^3$, $10^4$, $10^5$, and $10^6$ cells per plate, and plating efficiencies were determined as the number of colonies produced per cell, 1.0 being the maximum. The only previously known constitutively active CPs of Class A β-lactamases are terminated in the loops before the C-terminal helix and before the C-terminal strand in the β-sheet of the α-ω domain (Pieper et al., *Biochemistry* (1997) 36:8767; see FIG. 2). The latter is represented here by G253/K254, and it plates with greater than 90% efficiency on 25 μg/ml ampicillin without the assistance of the break-point disulfide. All other CPs were inactive without the break-point disulfide. However, when cysteines were added to the N- and C-termini four of these inactive CPs produced selectable activity on 25 μg/ml ampicillin, though one (K215/V216) had a plating efficiency of only ~0.01. Three of these CPs, like the constitutive CPs, had break-points in the α-ω domain. Only E197/L198 of the μ domain break-points, hereinafter referred to as CP198-197, was active. CP198-197 was by far the most active of all disulfide-dependent CPs. Coincidentally, the fragments corresponding to the same break-point were the only fragments which could be activated by the disulfide alone, and that observation could only be accounted for by assuming that the fragments could refold without assistance, but the complex was unstable.

Since four of the nine inactive CPs can be activated by the break-point disulfide, it was of interest to determine if constitutive break-point disulfide formation could be manipulated by inclusion of a disulfide reducing agent in the medium. If so, one could then constrain formation of the break-point disulfide to dependence on a ligand-dependent interaction of heterologous domains fused to the break-point termini via flexible linkers. All ten CPs were tested for plating efficiency on 25 μg/ml ampicillin in the presence of reduced

TABLE 6

Activation of Circular Permutations of TEM-1 β-lactamase by Break-Point Disulfide Formation [a]

| | GSH (mM) | | | | | | | 10.0 | |
|---|---|---|---|---|---|---|---|---|---|
| Break-Point | 0 | 0.1 | 0.5 | 1.0 | 2.0 | 5.0 | Amp25 | $Amp_{max}$ [c] | Bkgd. [d] |
| N52/S53 | +[b] | ++ | +/− | ++ | ++ | ++ | +++ | 50 | − |
| E63/E64 | − | − | − | − | − | − | − | − | − |
| L91/G92 | − | + | +/− | − | + | + | + | 25 | − |

TABLE 6-continued

Activation of Circular Permutations of TEM-1 β-lactamase
by Break-Point Disulfide Formation [a]

| | GSH (mM) | | | | | | | | |
|---|---|---|---|---|---|---|---|---|---|
| | | | | | | | | 10.0 | |
| Break-Point | 0 | 0.1 | 0.5 | 1.0 | 2.0 | 5.0 | Amp25 | $Amp_{max}$ [c] | Bkgd. [d] |
| Q99/N100 | − | + | +++ | ++ | +++ | +++ | +++ | 50 | − |
| H158/V159 | − | − | − | − | − | − | − | − | − |
| P174/N175 | − | − | − | − | − | ++ | − | 25 | − |
| E197/L198 | ++++ | ++++ | ++++ | ++++ | ++++ | ++++ | ++++ | 200 | +/− |
| K215/V216 | +/− | ++ | +++ | ++ | +++ | +++ | ++++ | 50 | − |
| A227/G228 | +++ | +++ | ++++ | ++++ | ++++ | ++++ | ++++ | 100 | − |
| G253/K254 | +++ | +++ | ++++ | ++++ | ++++ | ++++ | ++++ | 400 | ++++ |

[a] Circular permutations (CPs) were expressed with or without cysteines at the break-point termini in TG1 cells and plated onto 25 µg/ml ampicillin with 5 mM IPTG and reduced glutathione (GSH) from 0 to 10 mM.
[b] Activities are expressed as plating efficiencies (colonies per cell). −, <$10^{-4}$; +/−, $10^{-4}$-0.01; +, 0.01-0.10; ++, 0.10-0.30; +++, 0.30-0.90; ++++, >0.90.
[c] Maximum ampicillin concentration in µg/ml on which plating efficiency of disulfide-activated CP is >10% in the presence of 10 mM GSH.
[d] Bkgd, background activity on 25 µg/ml ampicillin without cysteines at the break-point termini.

glutathione (GSH) in amounts ranging up to 10.0 mM. Surprisingly, the activities of most CPs actually increased between 0 and 0.1-0.5 mM GSH, and then decreased between 0.5 and 1.0 mM before increasing again up to 10.0 mM. Remarkably, eight out of ten CPs produced selectable activity on 25 µg/ml ampicillin in the presence of 10 mM GSH.

The two-phase response of β-lactamase activity to GSH could be explained as follows. TEM-1 β-lactamase has a natural disulfide buried in the interior of the protein. Normally, this disulfide is formed rapidly by the DsbA oxidase in the bacterial periplasm before folding is completed. However, if the disulfide fails to form before folding is completed, TEM-1 is still active, though its specific activity and/or stability can be reduced to, (Walker and Gilbert, *J Biol Chem* (1994 269:28487). For those CPs which show the bi-phasic response, it is likely that initially one or two mixed disulfides may form between the native thiols and the break-point thiols, and that these are inhibitory to folding. In the presence of low amounts of GSH, formation of these mixed disulfides can be inhibited, thereby increasing activity by removing the inhibition to folding. At higher concentrations of GSH, the premature formation of the break-point disulfide can predominate, and this can again become inhibitory to folding. The reason for this is that in accordance with the hierarchical nature of protein folding, premature constraining of the termini can sterically hinder the conformational search for native structure. At still higher GSH concentrations, formation of the break-point disulfides is retarded but not prevented, thereby relieving the steric constraint on folding and stabilizing the final fold to increase activity still further.

Three CPs did not exhibit this bi-phasic response to GSH. Of these only CP198-197 plated at nearly 100% efficiency at all GSH concentrations. Thus, it appeared to be the only CP which was unaffected by mixed disulfide formation or premature break-point disulfide formation. The α-ω CPs, A227/G228 (CP228-227) and the constitutively active G253/K254 (CP254-253), seemed to be slightly inhibited at the lower GSH concentrations, implying that they may have had some tendency to form inhibitory mixed disulfides or to form the break-point disulfide prematurely. Even at 10.0 mM neither GSH nor DTT retards disulfide formation enough to begin to reduce the plating efficiencies of the CPs on 25 µg/ml ampicillin. Above 10.0 mM GSH or DTT, plating efficiencies begin to decline due to general toxicity. This suggests that formation of break-point disulfides in CPs is nearly as robust as formation of native disulfides, perhaps because the former are perpetually exposed to oxidation, whereas native disulfides, which are mostly buried, must form rapidly before folding sequesters the free thiols from oxidation. Thus, it may be difficult to control break-point disulfide formation without also impairing native disulfide formation, with toxic consequences. However, when the ampicillin concentration is raised in the presence of 10 mM GSH/DTT plating efficiencies fall precipitously, as expected. Table 6 also shows the maximum ampicillin concentrations on which the disulfide-activated CPs plate with efficiencies of >10% in the presence of 10 mM GSH. As expected, maximum ampicillin resistance correlated with plating efficiency on 25 µg/ml ampicillin.

The next step in assessing the power of the break-point disulfide to identify CPs which can be developed into molecular interaction biosensors was to determine if the break-point disulfides in the seven disulfide-dependent TEM-1 CPs could be functionally replaced by a ligand-dependent interaction between heterologous domains fused to the break-point termini. Initially, the break-point cysteines in all ten CPs were replaced by the leucine zipper helixes from the c-fos and c-jun subunits of the AP-1 transcription factor (Karin et al., *Curr Opin Cell Biol* (1997) 9:240) with intervening $(G_4S)_3$ (SEQ ID NO:4) linkers. Surprisingly, none of the CPs produced selectable activity, including the constitutively-active CP254-253 and CP198-197. The latter had the same break-point as the α197/ω198 fragment complementation, which was strongly activated by the same c-fos and c-jun helix fusions. Furthermore, the c-fos/c-jun interaction was found to inhibit disulfide activation of CP198-197. These observations plus the expected rapid folding of the c-fos and c-jun helixes and their high affinity for one another ($K_d \sim 10^{-8}$ M) strongly suggest that the c-fos/c-jun interaction inhibits CP activation by prematurely constraining the termini, which are expected to hinder the hierarchical search for the active conformation.

11a. Activation of β-lactamase CP198-197 by a Model 3-component Interaction.

CP198-197 was tested for activation by a model ligand-dependent interaction. Such interactions are not expected to occur early in the folding pathway because they require the folding of three different components and a bi-molecular interaction. The model interaction was comprised of two proteins which bind separate epitopes on the extra-cellular domain (ED) of the human B-cell activation antigen, CD40. The CD40-binding proteins were comprised of thioredoxin with 12-mer peptides inserted into the active site, which peptides had been selected for their ability to bind CD40 non-competitively. Such thioredoxin-scaffolded peptides were termed trxpeps, and these particular CD40-binding trxpeps are designated BW10-1 and p44-4-2. The coding sequences for these trxpeps were inserted into the pAO1 expression vector shown in FIG. 11 as Interactor 1 and Interactor 2. The coding sequence for CD40ED was inserted into the pAE1 vector shown in FIG. 11 as the Ligand.

When these two constructs were co-expressed in the periplasm of *E. coli* strain TG-1, the results shown in Table 4 (above) were obtained. Since thioredoxin itself dimerizes weakly, CP198-197 was slightly activated even in the absence of free CD40ED. However, when CD40ED was present the cells plated quantitatively on 25 µg/ml ampicillin, whereas in the absence of CD40ED fewer than 10 colonies had been obtained from 10,000 cells plated. Thus, the signal-to-noise ratio for activation by CD40ED was greater than 1000.

Various control interactions were also tested. For example, fusion of CD40 to the ω198 β-lactamase fragment neither interfered with nor enhanced its ability to activate the trxpep-CP fusion. However, both trxpeps were required for activation of the CP by CD40. When fused to each trxpep singly the CP could not act like the fragments and complement intermolecularly in the presence of CD40. The CP could, however, be activated by combinations of CD40-trxpep interactions and c-fos/c-jun helix interactions to about the same extent as by both CD40-trxpep interactions together. Finally, when CD40 and the same trxpeps were used to activate complementation of the α197 and ω198 fragments of TEM-1, the resulting activity was up to 10-fold lower with respect to plating efficiency than that of the CP. Thus, when fused to binders of modest affinity β-lactamase CP198-197 appears to be capable of highly specific and robust activation by, as well as highly sensitive detection of a model cell surface receptor.

11b. Activation of β-lactamase CP198-197 by an Antibody-antigen Interaction.

Figure 11:
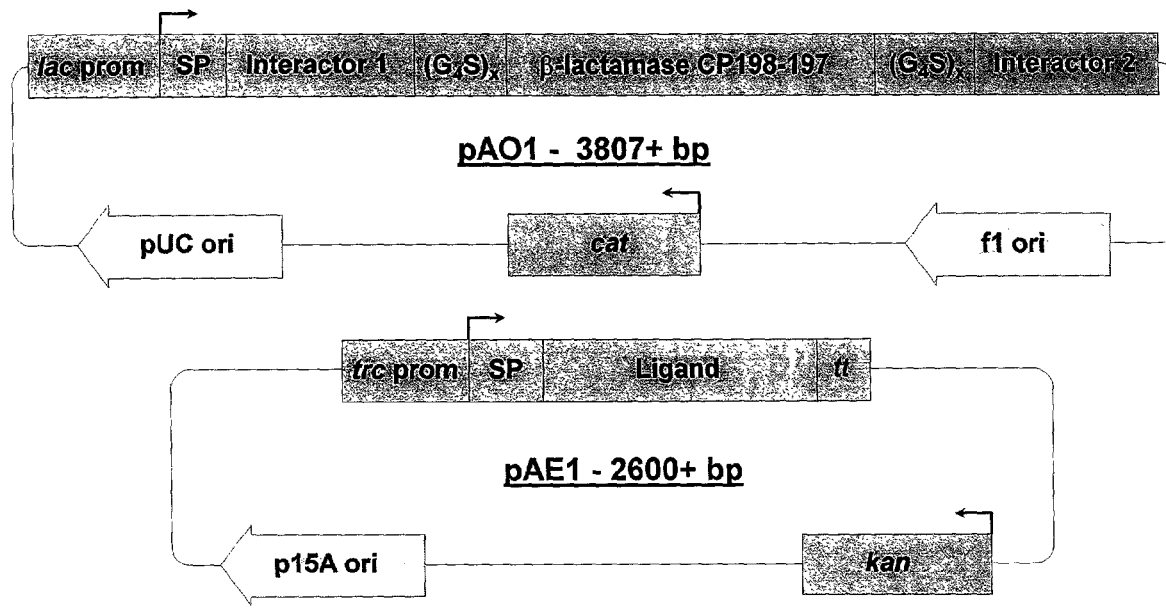
FIG. 11 shows vectors for the expression of heterologous proteins as fusions to the break-point termini of β-lactamase circular permutation L198-E197 (CP198-197). Also shown are data for the activation of the CP by CD40 and a CD40-specific single-chain antibody (scFv) assisted by the c-fos/c-jun leucine zipper helix interaction. Three different arrangements of the interactors were tested. In each case one of the leucine zipper helixes was fused to the ligand and the other served as one of the interactors. Max. amp$^r$, maximum ampicillin concentration on which on which the ligand-interactor combination will plate with at least 10% efficiency. S/N (amp25), signal-to-noise ration, i.e., the ratio of plating efficiencies on 25 μg/ml ampicillin with and without the ligand or interactors. lac prom; SP, signal peptide for secretion; (G$_4$S)$_x$ (SEQ ID NO:4), flexible linker of variable length, tt, transcription terminator; f1 ori, f1 phage origin of replication; pUC ori, p15A ori, plasmid origins of replication; cat, chloramphenicol resistance; kan, kanamycin resistance.

We also tested the ability of interactions between CD40 and a CD40-specific single-chain antibody Fv fragment (scFv) to activate CP198-197 with the assistance of the c-fos/c-jun leucine zipper helix interaction. This is relevant to the utility of the β-lactamase CP system for the selection of antigen-specific antibodies from antibody libraries. The scFv was derived by standard methods (Larrick and Balint, *Antibody Techniques* (1994) Academic Press, pp. 103-113) from a murine hybridoma. The interactors were tested in four orientations. These are depicted in FIG. 11. When both the interactor-expressing vector (pAO1) and the ligand-expressing vector (pAEL) for each orientation were co-expressed in the periplasm of *E. coli* strain TG-1, all four orientations produced robust ligand-dependent activation of the CP as indicated by quantitative plating on 25 µg/ml ampicillin, and signal-to-noise ratios of >1000 when compared to the plating efficiency of the interactors alone without the ligand. It is of interest to note that the ability of a high affinity antigen-antibody interaction did not produce greater activation of the CP than did a much lower affinity interaction between the same antigen and a trxpep. This was due primarily to the fact that the scFv was much less stable than the trxpep, and so its steady-state concentration in the bacterial periplasm can be presumed to have been much lower.

The preferred orientation for scFv in fusions is always N-terminal, whether fused to the CP as an interactor or to a leucine zipper helix as a ligand. It was of particular interest to test the antigen in multiple orientations, i.e., as both N-terminal and C-terminal fusions to both the CP and the leucine zipper helixes. There are several reasons for this. First of all, access of antibodies or other interactors to some epitopes on the ligand can be restricted in any given orientation by the size of the ligand and the lengths of the linkers between interactors and CP. Also, when expressed in fusions many proteins or protein domains can have distinct orientation preferences with regard to folding efficiency and stability. Finally, insofar as the specific activity of the activated CP will be sensitive to the dimensions of the ligand-interactor complex, the available orientations can also differ with respect to the ligand-dependent increment in the enzymatic activity of the CP.

The fact that robust activation occurred in all four orientations indicates that optimal orientations are available for any interactor or ligand with respect to all of these parameters, i.e., epitope accessibility, folding efficiency, stability, and specific activity. An orientation preference is indicated in the present experiment by the fact that the activity was higher with respect to maximum ampicillin resistance when CD40 was fused to the C-terminus of the CP. This was apparently due to a chaperone effect of CD40 on the stability of the CP in this orientation. We have observed that CD40 has a similar effect on the β-lactamase α197 fragment when it is fused to the same break-point. In practice, when attempting to use the system to select antibodies to antigens or to trap protein-protein interactions from expressed sequence libraries it will be prudent to express the antigens or expressed sequence libraries in as many of these orientations as possible to ensure maximum efficiency of recovery of desired ligands and interactors.

Example 12

A Fragment Complementation System for Neomycin Phosphotransferase.

Enzyme fragment complementation systems can also be useful for selection for the simultaneous incorporation of multiple genetic elements into the same cell or organism. For example, the production of secretory IgA antibodies in plants requires the introduction of four different genes into the same plant. For practical reasons this requires the introduction of at least two and preferably three different DNA molecules. For the production of genetically stable transgenic plants, each DNA molecule must carry its own selectable marker. The use of multiple antibiotic selection systems on the same transformants is cumbersome and inefficient, as the overall false positive and false negative rates tend to scale as the product of the rates for the individual antibiotics. Thus, two- or three-piece fragment complementation systems for a single antibiotic offer a distinct advantage over multiple antibiotic selection.

For a two fragment system, dependence of activation on the interaction of heterologous domains is not necessary. However, for simultaneous selection of triple transgenics, complementation of the enzyme fragment pair must be dependent on a heterologous interaction mediated by a free ligand, analogous to the activation of β-lactamase by the tri-molecular interaction of α197-jun, scFv-ω198, and CD40-fos, as described above. For these applications, the most important parameter is the maximum activity of the reconstituted enzyme, which is a function of both the specific activity and the efficiency of complementation. The activation index is not relevant because each fragment alone will have essentially no detectable activity, providing a background of zero. Thus, to insure recovery of the most competent fragment pairs for intra-cellular activity, the fos and jun interactors should be used with tri-peptide libraries between the break-points and the $(Gly_4Ser)_3$ (SEQ ID NO:4) linkers. The tri-peptide libraries will provide stabilizers for each fragment so that the selection will be biased toward the fragments producing the highest specific activities. For two-trait selection applications, i.e., bi-molecular selections, where a heterologous interaction is not required, specific activity can be increased further by mutagenesis and selection for fold accelerating mutations. For three-trait selection applications, selected fragment pairs will have to be tested for dependence on the heterologous interaction. In this case, the activation index will be of some importance, but as with in vitro applications a modest index of 1000 will be more than adequate for clean selections.

Neomycin phosphotransferase II (NPTII; Genbank accession no. M77786) is a 267-amino acid enzyme from $E.\ coli$ which inactivates aminoglycoside antibiotics such as neomycin and kanamycin by phosphorylation from ATP. NPTII is widely used as a selectable marker for plant and animal cell transformation. Thus, fragment complementation systems for NPTII are particularly useful for facile generation of multiple-trait plant and animal transgenics. The three-dimensional structure of NPTII is not known, and its homology to known structures is too low for reliable prediction. However, as described above, empirically-derived neural net algorithms are available which allow fairly accurate prediction of secondary structure and solvent exposure for any protein sequence. The best of these algorithms is the PredictProtein program of Rost and Sander (1993, 1994, supra). Application of this program to the protein sequence of NPTII produced the result shown in FIG. 12. Ten regions of the sequence have been predicted to have little secondary structure and to be exposed to solvent, and therefore to be potential sites for productive fragmentation. Fragment pairs corresponding to breakage in the center of each of these ten regions, or at two equally-spaced sites in the longer regions, can be generated by PCR with appropriate primers, and subcloned into vectors like those illustrated in FIG. 6 for expression as the fos and jun helix fusions with intervening linkers. The vectors differ from those in FIG. 6 in not encoding signal peptides, and the pAO1 vector has kanamycin resistance instead of ampicillin resistance. Also, the vectors contain VRK or NNK random tri-peptide-encoding sequences between the cloning sites for the enzyme fragments and the $(Gly_4Ser)_3$ (SEQ ID NO:4) linkers.

The PCR product for each fragment is restriction digested and ligated into the appropriate vector, α fragments into the pAE1-type vector and ω fragments into the pAO1-type vector. The ligation products are then introduced into TG-1 cells by high-voltage electroporation, and plated onto chloramphenicol or ampicillin. At least $10^4$ transformants are collected for each fragment. Also, kanamycin sensitivity is determined for each fragment library, both to prevent false positives and to determine the minimum quantitatively selective kanamycin concentration. This should be the concentration on which single fragment plating efficiencies are $<10^{-6}$, since the frequencies of the fragment-stabilizing peptides could be this low. Since $\sim 10^{-8}$ co-transformants will be needed for each fragment pair for complete coverage of the tri-peptide libraries, quantitative phage infection should be used to combine the two libraries for each fragment pair. This is accomplished by rescuing the ω-fragment libraries (in the pAO1-type phagemid vector) as phage using M13K07 helper phage as described above. For facile quantitative infection at least $10^9$ cells bearing each α fragment library should be inoculated with at least $10^{11}$ phage bearing the corresponding ω fragment library. After one-two hours in suspension culture with gentle shaking to allow phage adsorption, penetration, and initiation of gene expression, the cells of each fragment pair are centrifuged, washed, and plated onto ten 150-mm dishes containing solid LB medium with the minimum quantitatively selective concentration of kanamycin.

After overnight growth at 37° C., all kanamycin-resistant colonies can be pooled and re-plated onto increasing concentrations of kanamycin to identify those tri-peptide/fragment pair combinations producing the highest levels of kanamycin resistance. As many of the most active clones as necessary should be tested for dependence of activity on the fos-jun interaction. This can most easily be accomplished by removing one of the helixes by restriction digestion at sites in the gene construct included for this purpose. The digestion products are then re-ligated, re-transformed into TG-1 cells, and replated on kanamycin. As explained above, activation indexes of 1000 are more than adequate, so the most active pairs with indexes of at least 1000 are optimal. For tri-molecular activation in the cytoplasm, two hetero-dimerizing helix pairs can conveniently be used, such as the parallel-binding helixes from fos and jun as described above, and the anti-parallel-binding helixes from yeast DNA topoisomerase II (TopII; Berger et al., Nature (1996) 379:225). One of each helix pair is fused to an NPTII fragment, and the other two helixes are fused to each other, so that the NPTII fragments only come together when the 2-helix fusion was present to form the tri-molecular complex. For example, an α-TopIIN fusion and a fos-ω fusion were only brought together and activated by a jun-TopIIC fusion. Genes encoding each of the three fusions can then be distributed among three different DNA constructs which also encode genes of interest. In this way eukaryotic cells can be transformed with a mixture of the three different constructs and selected for the simultaneous presence of all three genes in the same cell simply by selection for growth on a single antibiotic.

For the TEM-1 β-lactamase of $E.\ coli$, the type member of the Class A penicillinases, fragments have been identified which can complement to form active enzyme when and only when the "break-point" termini of the fragments are fused to proteins or other molecules which interact with each other directly or preferably through a second molecule. Furthermore, the subject invention presents new methods whereby enzyme fragments capable of interaction-dependent complementation can be identified and modified specifically to confer dependence of their activity on the interaction of heterologous domains fused to the break-point termini. Ligand-activated or interaction-activated β-lactamases can be activated in multiple locations, including the bacterial periplasm, bacterial cytoplasm, eukaryotic cell cytoplasm, or in vitro. They are highly active against a wide variety of substrates, including antibiotics, chromogens, and fluorogens, as well as β-lactam pro-drugs, pro-antibiotics, and pro-nutrients, which can thus be used for both positive and negative viability selection and color selection. The utility of β-lactamase fragment complementation systems has been demonstrated for monitoring interactions between and among cell-surface receptors, antibodies, and random peptide libraries displayed on the surface of a natural protein.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporate by reference.

The invention now having been fully described, it will be apparent to one of ordinary skill in the art that many changes and modifications can be made thereto without departing from the spirit or scope of the appended claims.

What is claimed is:

1. A polypeptide consisting essentially of:

a circularly permutated TEM-1 β-lactamase protein, joined at the original amino and carboxy termini, having an N-terminal portion with a new C-terminus and a C-terminal portion with a new N-terminus, a first interactor domain, and a second interactor domain;

wherein the first interactor domain is fused through the new N-terminus of the C-terminal portion, and the second interactor domain is fused through the new C-terminus of the N-terminal portion; and wherein the new N-terminus and the new C-terminus are located within a solvent exposed loop between amino acid residues Thr 195 and Ala 202 (residues 170-177 of SEQ ID NO:2); and wherein the first interactor domain is selected from the group consisting of an antibody, an antigen, a first monomer of a hetero-dimerizing helix, a second monomer of a hetero-dimerizing helix, a receptor, a member of an expressed sequence library, and a member of a constrained peptide library; and wherein the second interactor domain is selected from the group consisting of an antibody, an antigen, a first monomer of a hetero-dimerizing helix, a second monomer of a hetero-dimerizing helix, a receptor, a member of an expressed sequence library, and a member of a constrained peptide library;

wherein the circularly permutated TEM-1 β-lactamase protein is functionally reconstituted only upon binding of said first interactor domain to said second interactor domain, optionally through a ligand.

2. The polypeptide of claim 1, wherein the new C-terminus of the N-terminal portion is Glu 197 (residue 172 of SEQ ID NO:2) and the new N-terminus of the C-terminal portion is Leu 198 (residue 173 of SEQ ID NO:2).

3. The polypeptide of claim 1, wherein said first interactor domain and said second interactor domain bind to a single ligand, and
   wherein said circularly permutated TEM-1 β-lactamase protein is functionally reconstituted only upon binding of said first interactor domain and said second interactor domain to said ligand.

4. The polypeptide of claim 3, wherein said ligand is comprised of an antigen fused to a second monomer of a hetero-dimerizing helix protein, said first interactor domain is an antibody, and said second interactor domain is a first monomer of a hetero-dimerizing helix, or
   wherein said ligand is comprised of an antibody fused to a second monomer of a hetero-dimerizing helix protein, said first interactor domain is an antigen and said second interactor domain is a first monomer of a hetero-dimerizing helix and
   wherein the first monomer of the hetero-dimerizing helix specifically binds to the second monomer of the hetero-dimerizing helix protein and the antibody specifically binds to the antigen.

5. The polypeptide of claim 4, wherein the antibody of the first interactor domain, or the antibody of the ligand comprising an antibody fused to a second monomer of the hetero-dimerizing helix protein, is a single chain antibody fragment (scFv).

6. The polypeptide of claim 1, wherein the first interactor domain is fused through a first flexible polypeptide linker to the circularly permutated β-lactamase protein through the N-terminal break-point, and the second interactor domain is fused through a second flexible polypeptide linker to the circularly permutated β-lactamase protein through the C-terminal break-point.

7. The polypeptide of claim 6, wherein said first polypeptide linker is 3-30 amino acids in length; and wherein said second polypeptide linker is 3-30 amino acids in length.

* * * * *

```
                        SEQUENCE LISTING

<160> NUMBER OF SEQ ID NOS:  13

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence:  library
      generated random peptide

<400> SEQUENCE: 1

Cys Gly Pro Lys Glu Leu Arg Ile Gly Gly Arg Pro Arg Arg Pro Gly
 1               5                  10                  15

Pro Cys

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence:  library
      generated random peptide

<400> SEQUENCE: 2

Cys Gly Pro Glu Gly Gln Gly Gly Val Ala Val Gly Gly Val Gly Gly
 1               5                  10                  15

Pro Cys

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence:  library
      generated random peptide

<400> SEQUENCE: 3

Cys Gly Pro Ala Lys Arg Ala Asp Val Glu Phe Ser Leu Glu Pro Gly
 1               5                  10                  15

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence:  library
      generated random peptide

<400> SEQUENCE: 4

Cys Gly Pro Lys Ser Ala Gly Lys Gly Arg Lys Asp Arg Arg Lys Gly
 1               5                  10                  15

Pro Cys

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence:  library
```

-continued generated random peptide

<400> SEQUENCE: 5

Cys Gly Pro Arg Thr Arg Val Asn His Gln Gly Gln Lys Thr Arg Gly
 1               5                  10                  15
Pro Cys

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: library
      generated random peptide

<400> SEQUENCE: 6

Cys Gly Pro Ala Gly Ala Ile Arg His Glu His Arg Gln Gly Leu Gly
 1               5                  10                  15
Pro Cys

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: library
      generated random peptide

<400> SEQUENCE: 7

Cys Gly Pro Asp Thr Gly Leu Glu Thr Asp Ala Ala Asp Ala Ser Gly
 1               5                  10                  15
Pro Cys

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: library
      generated random peptide

<400> SEQUENCE: 8

Cys Gly Pro Arg Arg Val Arg Glu Thr Val Ala Val Glu Ser Ser Gly
 1               5                  10                  15
Pro Cys

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: library
      generated random peptide

<400> SEQUENCE: 9

Cys Gly Pro Pro Cys Ala Thr Phe Glu Glu Ala Lys Ser Asn Gln Gly
 1               5                  10                  15
Pro Cys

<210> SEQ ID NO 10
<211> LENGTH: 18
<212> TYPE: PRT
<213> ORGANISM: Artificial Sequence
<220> FEATURE:

```
<223> OTHER INFORMATION: Description of Artificial Sequence:  library
      generated random peptide

<400> SEQUENCE: 10

Cys Gly Pro Gly Arg Glu Ser Arg Gly Arg Cys Tyr Thr Pro Ser Gly
 1               5                  10                  15

Pro Cys

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence:  library
      generated random peptide

<400> SEQUENCE: 11

Cys Gly Pro Asn Thr Pro Asp Glu Glu Met Ala Pro Gln Ala Pro Gly
 1               5                  10                  15

Pro Cys

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence:  library
      generated random peptide

<400> SEQUENCE: 12

Cys Gly Pro Val Val His Ile Lys Thr Asn Glu Gln Ala Ala Pro Gly
 1               5                  10                  15

Pro Cys

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence:  library
      generated random peptide

<400> SEQUENCE: 13

Cys Gly Pro Val Ala Glu Glu Pro Ala Gly Gly Ala Gly Arg Pro Gly
 1               5                  10                  15

Pro Cys
```